(12) United States Patent
Macdonald et al.

(10) Patent No.: US 9,226,484 B2
(45) Date of Patent: *Jan. 5, 2016

(54) HUMAN LAMBDA LIGHT CHAIN MICE

(71) Applicant: Regeneron Pharmaceuticals, Inc., Tarrytown, NY (US)

(72) Inventors: Lynn Macdonald, White Plains, NY (US); Sean Stevens, San Diego, CA (US); Cagan Gurer, Valhalla, NY (US); Andrew J. Murphy, Croton-On-Hudson, NY (US); Karolina A. Meagher, Tarrytown, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/800,263

(22) Filed: Jul. 15, 2015

(65) Prior Publication Data

US 2015/0320023 A1    Nov. 12, 2015

Related U.S. Application Data

(60) Continuation of application No. 14/638,429, filed on Mar. 4, 2015, which is a continuation of application No. 13/945,582, filed on Jul. 18, 2013, now Pat. No. 9,006,511, which is a division of application No. 13/166,171, filed on Jun. 22, 2011, now Pat. No. 9,012,717.

(60) Provisional application No. 61/357,314, filed on Jun. 22, 2010, provisional application No. 61/357,317, filed on Jun. 22, 2010.

(51) Int. Cl.
*A01K 67/027* (2006.01)

(52) U.S. Cl.
CPC ......... *A01K 67/0278* (2013.01); *A01K 2207/15* (2013.01); *A01K 2217/052* (2013.01); *A01K 2217/15* (2013.01); *A01K 2227/105* (2013.01)

(58) Field of Classification Search
USPC ........................................................ 800/18
See application file for complete search history.

(56) References Cited

U.S. PATENT DOCUMENTS

| 5,658,727 | A | 8/1997 | Barbas et al. |
| 6,162,963 | A | 12/2000 | Kucherlapati et al. |
| 6,596,541 | B2 | 7/2003 | Murphy et al. |
| 6,632,976 | B1 | 10/2003 | Tomizuka et al. |
| 6,998,514 | B2 | 2/2006 | Bruggemann |
| 7,435,871 | B2 | 10/2008 | Green et al. |
| 8,502,018 | B2 | 8/2013 | Murphy et al. |
| 2002/0026036 | A1 | 2/2002 | Shitara et al. |
| 2002/0088016 | A1 | 7/2002 | Bruggemann |
| 2003/0217373 | A1 | 11/2003 | Green et al. |
| 2005/0060763 | A1 | 3/2005 | Bruggeman et al. |
| 2006/0015957 | A1 | 1/2006 | Lonberg et al. |
| 2006/0026696 | A1 | 2/2006 | Buelow et al. |
| 2009/0258392 | A1 | 10/2009 | Gallo et al. |
| 2011/0138489 | A1 | 6/2011 | Tanamachi |
| 2011/0236378 | A1 | 9/2011 | Green et al. |
| 2012/0070861 | A1 | 3/2012 | Macdonald et al. |

FOREIGN PATENT DOCUMENTS

| WO | WO-00/26373 | A1 | 5/2000 |
| WO | WO-03/047336 | A2 | 6/2003 |
| WO | WO-2008/054606 | A2 | 5/2008 |
| WO | WO-2009/143472 | A2 | 11/2009 |
| WO | WO-2010/039900 | A2 | 4/2010 |
| WO | WO-2011/004192 | A1 | 1/2011 |
| WO | WO-2011/158009 | A1 | 12/2011 |

OTHER PUBLICATIONS

Butler, J.E., "Immunoglobulin diversity, B-cell and antibody repertoire development in large farm animals," Rev. Sci. Tech. Off. Int. Epiz., 17(1):43-70 (1998).
Cavelier et al., "B lineage-restricted rearrangement of a human Igκ transgene," Eur. J. Immunol, 27: 1626-1631; 1997.
Cocea, L. et al., "A targeted deletion of a region upstream from the Jk cluster impairs k chain rearrangement in cis in mice and the 103/bcl2 cell line," Journal of Experimental Medicine, 189:1443-1450(1999).
Combriato et al., "Regulation of Human IgA. Light Chain Gene Expression," The Journal of Immunology, 168: 1259-1266, (2002).
Dudley, D. et al., "Mechanism and Control of V(D)J Recombination versus Class Switch Recombination: Similarities and Differences," Adv. in Immol., vol. 86:43-112 (2005).
European Search Report for EP12195716, 15 pages (Jan. 29, 2013).
Gallo et al., US 20090258392 A1, Oct. 15, 2009, SEQ ID No. 112 alignment with SEQ ID No. 100 of 13166200.
Gorman, J.R. et al., "The Igk 3' Enhancer Influences the Ratio of Igk versus Igλ B Lymphocytes." Immunity 5(3):241-252 (1996).
Grawunder, U., Rolink, A., Melchers, F. 1995. Induction of sterile transcription from the kL chain gene locus in V(D)J recombinase-deficient progenitor B cells. International Immunology 7(12):1915-1925. (1995).
International search report for PCT application No. PCT/US2011/041370, dated Sep. 22, 2011.
Leclercq, L., Betkeraitis, P., Reth, M. 1989. A novel germline Jk transcript starting immediately upstream of Jk1. Nucleic Acids Research 17(17):6809-6819.
Lefranc, M.P., "Nomeclature of the human immunoglobulin lambda (IgL) genes," Current Protocol in Immunology, No. supplement 40, 2000, pp. A.1 P.1-A.1 p. 37.

(Continued)

*Primary Examiner* — Michael Wilson
(74) *Attorney, Agent, or Firm* — Brendan T. Jones; Neil Miyamoto; Foley Hoag LLP

(57) ABSTRACT

Genetically modified mice are provided that express human λ variable (hVλ) sequences, including mice that express hVλ sequences from an endogenous mouse λ light chain locus, mice that express hVλ sequences from an endogenous mouse κ light chain locus, and mice that express hVλ sequences from a transgene or an episome wherein the hVλ sequence is linked to a mouse constant sequence. Mice are provided that are a source of somatically mutated human λ variable sequences useful for making antigen-binding proteins. Compositions and methods for making antigen-binding proteins that comprise human λ variable sequences, including human antibodies, are provided.

7 Claims, 24 Drawing Sheets

(56) References Cited

OTHER PUBLICATIONS

Lefranc, M.P., "Nomeclature of the human immunoglobulin lambda (IgL) genes," Experimental and Clinical Immunogenetics, 18(4): 242-254, 2001.

Lefranc, Marie-Paule & Lefranc, Gerard. "Immunoglobulin Lambda (IgL) Genes of Human and Mouse," Molecular Biology of B Cells. London: Elsevier Academic Press, 2004. Ed. Honjo, Tasuku; All, Frederick W.; Neuberger, Michal. Chapter 4, pp. 37-59.

Martin, D.J., and Van Ness, B.G. 1990. Initiation and Processing of Two Kappa Immunoglobulin Germ Line Transcripts in Mouse B cells. Molecular and Cellular Biology 10(5):1950-1958.

Martin, D.J., and Van Ness, B.G., Identification of a Germ Line Transcript from the Unrearranged Kappa Gene in Human B Cells. Molecular and Cellular Biology, 9(10): 4560-4562 (1989).

Montaño, et al., "Influence of the Isotype of the Light Chain on the Properties of IgG", Journal of Immunology, 168:224-231 (2002).

Moran, Nuala, "Mouse platforms jostle for slice of humanized antibody market," Nature Biotechnology, vol. 31(4): 267-268,2013.

Murphy, K., "The Generation of Lymphocyte Antigen Receptors," Janeway's Immunobiology 8th Edition. New York: Garland Science, 2012. Printed in USA. Chapter 5, Sections 5-1 to 5-4, pp. 158-162.

Nicholson, I.C., Zhou, X., Popov, A.V., Cook, G.P., Corps, E.M., Humphries, S., Ayling, C., D Goyenechea, B., Xian, J., Taussig, M.J., Neuberger, M.S., Bruggemann, M. 1999. Antibody Repertoires of Four- and Five-Feature Translocus Mice Carrying Human Immunoglobulin Heavy Chain and k and l light chain Yeast Artificial Chromosomes. J of Immunology 163:6898-6906.

Popov et al., "A Human Immunoglobulin λ Locus is Similarly Well Expressed in Mice and Humans," The Journal of Experimental Medicine, 189(10): 1611-1619 (1999).

Schlissel, M.S., and Baltimore, D. 1989. Activation of Immunoglobulin Kappa Gene Rearrangement Correlates with Induction of Germline Kappa Gene Transcription. Cell 58:1001-1007.

Third Party Observation for EP11728508.0, 6 pgs, (Dec. 3, 2012).

Third Party Observations in EP11728509, dated Dec. 4, 2012.

Van Ness, B.G., Weigert, M., Coleclough, C, Mather, E.L., Kelley, D.E., Perry, R.P., "Transcription of the Unrearranged Mouse Ck locus: Sequence of the Initation Region and Comparison of Activity with a Rearranged Vk-Ck Gene," Cell, 27(3 part 2): 593-602 (1981).

Williams, S.C., Frippiat, J., Tomlinson, I.M., Ignatovich, 0., Lefranc, M., Winter, G. 1996. Sequence Evolution of the Human Germline Vlambda Repertoire. J. Mol. Biol. 264:220-232.

Zachau, Hans G. "Immunoglobulin k Genes of Human and Mouse," Molecular Biology of B Cells. London: Elsevier Academic Press, 2004. Ed. Honjo, Tasuku; All, Frederick W.; Neuberger, Michal. Chapter 3, pp. 27-36.

| | 3' Human Vλ | Human Jλ1 | 5' Mouse Cκ |
|---|---|---|---|
| A6 | GCAACAATT | tcGTCTCTTCGGAACTGGGACCAAGGTCACCGTCCTAG | GGGCTGATGCTGCACCAACTGTATCCATCTTC |
| B6 | GCAACAATT | ATGTCTTCGGAACTGGGACCAAGGTCACCGTCCTAG | GGGCTGATGCTGCACCAACTGTATCCATCTTC |
| F6 | GCAACAATT | ATGTCTTCGGAACTGGGACCAAGGTCACCGTCCTAG | GGGCTGATGCTGCACCAACTGTATCCATCTTC |
| B7 | GCAACAATT | ATGTCTTCGGAACTGGGACCAAGGTCACCGTCCTAG | GGGCTGATGCTGCACCAACTGTATCCATCTTC |
| E7 | GCAACAAT | GTCTTCGGAACTGGGACCAAGGTCACCGTCCTAG | GGGCTGATGCTGCACCAACTGTATCCATCTTC |
| F7 | GCAACAATT | ATGTCTTCGGAACTGGGACCAAGGTCACCGTCCTAG | GGGCTGATGCTGCACCAACTGTATCCATCTTC |
| C8 | GCAACAATTT | ATGTCTTCGGAACTGGGACCAAGGTCACCGTCCTAG | GGGCTGATGCTGCACCAACTGTATCCATCTTC |
| E12 | CAAGTCGGTT | gTGTCTTCGGAACTGGGACCAAGGTCACCGTCCTAG | GGGCTGATGCTGCACCAACTGTATCCATCTTC |
| 1-4 | TGAGTGCT | TATGTCTTCGGAACTGGGACCAAGGTCACCGTCCTAG | GGGCTGATGCTGCACCAACTGTATCCATCTTC |
| 1-20 | TGAGTGCg | gctttttTTtGGAACTGGGACCAAGGTCACCGTCCTAG | GGGCTGATGCTGCACCAACTGTATCCATCTTC |
| 3B43 | CTGAATGGT | TATGTCTTCGGAACTGGGACCAAGGTCACCGTCCTAG | GGGCTGATGCTGCACCAACTGTATCCATCTTC |
| 5-8 | AGTGGTAAT | CATGTCTTCGGAACTGGGACCAAGGTCACCGTCCTAG | GGGCTGATGCTGCACCAACTGTATCCATCTTC |
| 5-19 | AGTGGTGCT | TATGTCTTCGGAACTGGGACCAAGGTCACCGTCCTAG | GGGCTGATGCTGCACCAACTGTATCCATCTTC |
| 1010 | AGCAGCACT | TATGTCTTCGGAACTGGGACCAAGGTCACCGTCCTAG | GGGCTGATGCTGCACCAACTGTATCCATCTTC |
| 11A1 | AGCAGCGCT | TATGTCTTCGGAACTGGGACCAAGGTCACCGTCCTAG | GGGCTGATGCTGCACCAACTGTA |
| 7A8 | GGTGGTGCT | TATGTCTTCGGAACTGGGACCAAGGTCACCGTCCTAG | GGGCTGATGCTGCACCAACTGTATCC |
| 3A3 | AGTAGCACT | TATGTCTTCGGAACTGGGACCAAGGTCACCGTCCTAG | GGGCTGATGCTGCACCAACTGTATCCATC |
| 2-7 | AGCAGCACT | TATGTCTTCGGAACTGGGACCAAGGTCACCGTCACCgCCTgG | GGGCTGATGCTGCACCA |
| FWR4 | | F G T K V T V L G | A D A A P T V S I F |

FIG. 11

| | 3' Human Vλ | Human Jλ | 5' Mouse Cκ |
|---|---|---|---|
| 5-2 | CAGCCTGAGTGGTTC | TGTGTTCGGAGGAGGCACCCGGCTGACCGCCCCTCG | GGGCTGATGCTGCACCAACTGTATCCATC |
| 2-5 | CAGCCTGAGTGGTT | ATGTCTTCGGAACTGGGACCAAGGTCACCGTCCTAG | GGGCTGATGCTGCACCAACTGTATCCATC |
| 1-3 | CAGCCTGAATGGT | GCTGTGTTCGGAGGAGGCACCCAGCTGACCGCCCTCG | GGGCTGATGCTGCACCAACTGTATCCATC |
| 4B-1 | CAGCCTGAGTGGTC | GGGTGTTCGGCGGAGGGACCAAGCTGACCGTCCTAG | GGGCTGATGCTGCACCAACTGTATCCATC |
| 3B-5 | CAGCAGCACTGC | TGTGTTCGGAGGAGGCACCCAGCTGACCGCCCTCG | GGGCTGATGCTGCACCAACTGTATCCATC |
| 7A-1 | CAGCAGTGGTAAT | GCTGTGTTCGGCGGAGGGACCAAGCTGACCGTCCTAG | GGGCTGATGCTGCACCAACTGTATCCATC |
| 5-1 | CAGCAGTGGTAATCATAG | GGTGTTCGGCGGAGGGACCAAGGTCACCGTCCTAG | GGGCTGATGCTGCACCAACTGTATCCATC |
| 4A-1 | CAGCCTGAGTGGTT | ATGTCTTCGGAACTGGGACCAAGGTCACCGTCCTAG | GGGCTGATGCTGCACCAACTGTATCCATC |
| 11A-1 | CAGCAGCGCT | GTGGTATTCGGCGGAGGGACCAAGCTGACCGTCCTAG | GGGCTGATGCTGCACCAACTGTATCCATC |
| 5-7 | CTACTATGGTGGTGCTC | GGGTGTTCGGCGGAGGGACCAAGCTGACCGTCCTAG | GGGCTGATGCTGCACCAACTGTATCCATC |
| 5-4 | CTCCTATAGTGGTGCTCGa | GTATTCGGCGGAGGGACCAAGCTGACCGTCCTAG | GGGCTGATGCTGCACCAACTGTATCCATC |
| 2-3 | GAGCAACTTCGTGT | CTGTGTTCGGAGGAGGCACCCAGCTGACCGCCCTCG | GGGCTGATGCTGCACCAACTGTATCCATC |
| FWR4 | | F  G  G  G  T  K  L  T  V  L  G | A  D  A  A  P  T  V  S  I |

FIG. 12

|  | 3' Human Vλ | Human Jλ1 | 5' Mouse Cλ2 |
|---|---|---|---|
| 2D1 | GCAGGCAGCAACAATTTa | aGTCTTCGGAACTGGGACCAAGGTCACCGTCCTAG | GTCAGCCCAAGTCCACTCCCACTCTC |
| 2D9 | GACAGCAGTGGTAATCAT | TATGTCTTCGGAACTGGGACCAAGGTCACCGTCCTAG | GTCAGCCCAAGTCCACTCCCACTCTC |
| 3E15 | GACAGCAGCACTGCc | GTCTTCGGAACTGGGACCAAGGTCACCGTCCTAG | GTCAGCCCAAGTCCACTCCCACTCTC |
| FWR4 |  | F  G  T  K  V  T  V  L  G | Q  P  K  S  T  P  T  L |

FIG. 13

```
                      SEQUENCE LISTING

<160> NUMBER OF SEQ ID NOS: 105

<210> SEQ ID NO 1
<211> LENGTH: 219
<212> TYPE: DNA
<213> ORGANISM: artificial sequence
<220> FEATURE:
<223> OTHER INFORMATION: synthetic

<400> SEQUENCE: 1
actttcagaa tgttcttgaa cagtctctga gaaacacgga agacggccgc ataacttcgt      60
atagtataca ttatacgaag ttattctaga cccccgggct cgataactat aacggtccta    120
aggtagcgac tcgagataac ttcgtataat gtatgctata cgaagttatc catggtaagc    180
ttacgtggca tacagtgtca gattttctgt ttatcaagc                           219

<210> SEQ ID NO 2
<211> LENGTH: 21
<212> TYPE: DNA
<213> ORGANISM: artificial sequence
<220> FEATURE:
<223> OTHER INFORMATION: synthetic

<400> SEQUENCE: 2
agctgaatgg aaacaaggca a                                               21

<210> SEQ ID NO 3
<211> LENGTH: 19
<212> TYPE: DNA
<213> ORGANISM: artificial sequence
<220> FEATURE:
<223> OTHER INFORMATION: synthetic

<400> SEQUENCE: 3
ggagacaatg ccccagtga                                                  19

<210> SEQ ID NO 4
<211> LENGTH: 21
<212> TYPE: DNA
<213> ORGANISM: artificial sequence
<220> FEATURE:
<223> OTHER INFORMATION: synthetic

<400> SEQUENCE: 4
tcccataggg ctaggatttc c                                               21
```

<210> SEQ ID NO 5
<211> LENGTH: 19
<212> TYPE: DNA
<213> ORGANISM: artificial sequence
<220> FEATURE:
<223> OTHER INFORMATION: synthetic

<400> SEQUENCE: 5
tcccctcaca ctgttcccc                                                19

<210> SEQ ID NO 6
<211> LENGTH: 19
<212> TYPE: DNA
<213> ORGANISM: artificial sequence
<220> FEATURE:
<223> OTHER INFORMATION: synthetic

<400> SEQUENCE: 6
ggtggagagg ctattcggc                                                19

<210> SEQ ID NO 7
<211> LENGTH: 17
<212> TYPE: DNA
<213> ORGANISM: artificial sequence
<220> FEATURE:
<223> OTHER INFORMATION: synthetic

<400> SEQUENCE: 7
gaacacggcg gcatcag                                                  17

<210> SEQ ID NO 8
<211> LENGTH: 21
<212> TYPE: DNA
<213> ORGANISM: artificial sequence
<220> FEATURE:
<223> OTHER INFORMATION: synthetic

<400> SEQUENCE: 8
tcaacctttc ccagcctgtc t                                             21

<210> SEQ ID NO 9
<211> LENGTH: 24
<212> TYPE: DNA
<213> ORGANISM: artificial sequence
<220> FEATURE:
<223> OTHER INFORMATION: synthetic

<400> SEQUENCE: 9
ccccagagag agaaaacaga tttt                                          24

<210> SEQ ID NO 10
<211> LENGTH: 20
<212> TYPE: DNA
<213> ORGANISM: artificial sequence
<220> FEATURE:
<223> OTHER INFORMATION: synthetic

<400> SEQUENCE: 10
ccctggtgaa gcatgtttgc                                               20

<210> SEQ ID NO 11
<211> LENGTH: 20
<212> TYPE: DNA
<213> ORGANISM: artificial sequence
<220> FEATURE:
<223> OTHER INFORMATION: synthetic

```
<400> SEQUENCE: 11
tgtggcctgt ctgccttacg                                              20

<210> SEQ ID NO 12
<211> LENGTH: 21
<212> TYPE: DNA
<213> ORGANISM: artificial sequence
<220> FEATURE:
<223> OTHER INFORMATION: synthetic

<400> SEQUENCE: 12
cacacctaga ccccggaagt c                                            21

<210> SEQ ID NO 13
<211> LENGTH: 21
<212> TYPE: DNA
<213> ORGANISM: artificial sequence
<220> FEATURE:
<223> OTHER INFORMATION: synthetic

<400> SEQUENCE: 13
tcgctttgcc agttgattct c                                            21

<210> SEQ ID NO 14
<211> LENGTH: 17
<212> TYPE: DNA
<213> ORGANISM: artificial sequence
<220> FEATURE:
<223> OTHER INFORMATION: synthetic

<400> SEQUENCE: 14
tgcggccgat cttagcc                                                 17

<210> SEQ ID NO 15
<211> LENGTH: 18
<212> TYPE: DNA
<213> ORGANISM: artificial sequence
<220> FEATURE:
<223> OTHER INFORMATION: synthetic

<400> SEQUENCE: 15
ttgaccgatt ccttgcgg                                                18

<210> SEQ ID NO 16
<211> LENGTH: 20
<212> TYPE: DNA
<213> ORGANISM: artificial sequence
<220> FEATURE:
<223> OTHER INFORMATION: synthetic

<400> SEQUENCE: 16
gcaaacaaaa accactggcc                                              20

<210> SEQ ID NO 17
<211> LENGTH: 19
<212> TYPE: DNA
<213> ORGANISM: artificial sequence
<220> FEATURE:
<223> OTHER INFORMATION: synthetic

<400> SEQUENCE: 17
ggccacattc catgggttc                                               19

<210> SEQ ID NO 18
```

```
<211> LENGTH: 22
<212> TYPE: DNA
<213> ORGANISM: artificial sequence
<220> FEATURE:
<223> OTHER INFORMATION: synthetic

<400> SEQUENCE: 18
ccatgactgg gcctctgtag ac                                              22

<210> SEQ ID NO 19
<211> LENGTH: 25
<212> TYPE: DNA
<213> ORGANISM: artificial sequence
<220> FEATURE:
<223> OTHER INFORMATION: synthetic

<400> SEQUENCE: 19
caagtcaggg tgctaatgct gtatc                                           25

<210> SEQ ID NO 20
<211> LENGTH: 19
<212> TYPE: DNA
<213> ORGANISM: artificial sequence
<220> FEATURE:
<223> OTHER INFORMATION: synthetic

<400> SEQUENCE: 20
cacagcttgt gcagcctcc                                                  19

<210> SEQ ID NO 21
<211> LENGTH: 22
<212> TYPE: DNA
<213> ORGANISM: artificial sequence
<220> FEATURE:
<223> OTHER INFORMATION: synthetic

<400> SEQUENCE: 21
gggcactgga tacgatgtat gg                                              22

<210> SEQ ID NO 22
<211> LENGTH: 21
<212> TYPE: DNA
<213> ORGANISM: artificial sequence
<220> FEATURE:
<223> OTHER INFORMATION: synthetic

<400> SEQUENCE: 22
tcataggtag gtctcagttt g                                               21

<210> SEQ ID NO 23
<211> LENGTH: 21
<212> TYPE: DNA
<213> ORGANISM: artificial sequence
<220> FEATURE:
<223> OTHER INFORMATION: synthetic

<400> SEQUENCE: 23
tgatctgcgc tgtttcatcc t                                               21

<210> SEQ ID NO 24
<211> LENGTH: 31
<212> TYPE: DNA
<213> ORGANISM: artificial sequence
<220> FEATURE:
<223> OTHER INFORMATION: synthetic

<400> SEQUENCE: 24
```
tgacatgaac catctgtttc tctctcgaca a                                    31

<210> SEQ ID NO 25
<211> LENGTH: 29
<212> TYPE: DNA
<213> ORGANISM: artificial sequence
<220> FEATURE:
<223> OTHER INFORMATION: synthetic

<400> SEQUENCE: 25
agagacgctc cgaggtcaag gtgctctag                                       29

<210> SEQ ID NO 26
<211> LENGTH: 23
<212> TYPE: DNA
<213> ORGANISM: artificial sequence
<220> FEATURE:
<223> OTHER INFORMATION: synthetic

<400> SEQUENCE: 26
tgggcacaac agacaatcgg ctg                                             23

<210> SEQ ID NO 27
<211> LENGTH: 16
<212> TYPE: DNA
<213> ORGANISM: artificial sequence
<220> FEATURE:
<223> OTHER INFORMATION: synthetic

<400> SEQUENCE: 27
accctctgct gtccct                                                     16

<210> SEQ ID NO 28
<211> LENGTH: 26
<212> TYPE: DNA
<213> ORGANISM: artificial sequence
<220> FEATURE:
<223> OTHER INFORMATION: synthetic

<400> SEQUENCE: 28
ccaagcagga ggtgctcagt tcccaa                                          26

<210> SEQ ID NO 29
<211> LENGTH: 24
<212> TYPE: DNA
<213> ORGANISM: artificial sequence
<220> FEATURE:
<223> OTHER INFORMATION: synthetic

<400> SEQUENCE: 29
tccacactgt cggctgggag ctca                                            24

<210> SEQ ID NO 30
<211> LENGTH: 21
<212> TYPE: DNA
<213> ORGANISM: artificial sequence
<220> FEATURE:
<223> OTHER INFORMATION: synthetic

<400> SEQUENCE: 30
acgagcgggt tcggcccatt c                                               21

<210> SEQ ID NO 31
<211> LENGTH: 37
<212> TYPE: DNA

<213> ORGANISM: artificial sequence
<220> FEATURE:
<223> OTHER INFORMATION: synthetic

<400> SEQUENCE: 31
ctgttcctct aaaactggac tccacagtaa atggaaa            37

<210> SEQ ID NO 32
<211> LENGTH: 27
<212> TYPE: DNA
<213> ORGANISM: artificial sequence
<220> FEATURE:
<223> OTHER INFORMATION: synthetic

<400> SEQUENCE: 32
tgccgcttat acaacactgc catctgc            27

<210> SEQ ID NO 33
<211> LENGTH: 37
<212> TYPE: DNA
<213> ORGANISM: artificial sequence
<220> FEATURE:
<223> OTHER INFORMATION: synthetic

<400> SEQUENCE: 33
agaagaagcc tgtactacag catccgtttt acagtca            37

<210> SEQ ID NO 34
<211> LENGTH: 21
<212> TYPE: DNA
<213> ORGANISM: artificial sequence
<220> FEATURE:
<223> OTHER INFORMATION: synthetic

<400> SEQUENCE: 34
gggctacttg aggaccttgc t            21

<210> SEQ ID NO 35
<211> LENGTH: 23
<212> TYPE: DNA
<213> ORGANISM: artificial sequence
<220> FEATURE:
<223> OTHER INFORMATION: synthetic

<400> SEQUENCE: 35 gacagcccctt acagagtttg gaa            23

<210> SEQ ID NO 36
<211> LENGTH: 23
<212> TYPE: DNA
<213> ORGANISM: artificial sequence
<220> FEATURE:
<223> OTHER INFORMATION: synthetic

<400> SEQUENCE: 36
aagaccagga gctctgccta agt            23

<210> SEQ ID NO 37
<211> LENGTH: 22
<212> TYPE: DNA
<213> ORGANISM: artificial sequence
<220> FEATURE:
<223> OTHER INFORMATION: synthetic

<400> SEQUENCE: 37
cccatcacga actgaagttg ag            22

```
<210> SEQ ID NO 38
<211> LENGTH: 20
<212> TYPE: DNA
<213> ORGANISM: artificial sequence
<220> FEATURE:
<223> OTHER INFORMATION: synthetic

<400> SEQUENCE: 38
cagggcctcc atcccaggca                                                    20

<210> SEQ ID NO 39
<211> LENGTH: 28
<212> TYPE: DNA
<213> ORGANISM: artificial sequence
<220> FEATURE:
<223> OTHER INFORMATION: synthetic

<400> SEQUENCE: 39
ccccagtgtg tgaatcactc taccctcc                                           28

<210> SEQ ID NO 40
<211> LENGTH: 20
<212> TYPE: DNA
<213> ORGANISM: artificial sequence
<220> FEATURE:
<223> OTHER INFORMATION: synthetic

<400> SEQUENCE: 40
cctctcctcc tcaccctcct                                                    20

<210> SEQ ID NO 41
<211> LENGTH: 20
<212> TYPE: DNA
<213> ORGANISM: artificial sequence
<220> FEATURE:
<223> OTHER INFORMATION: synthetic
<220> FEATURE:
<221> NAME/KEY: variation
<222> LOCATION: (4)...(4)
<223> OTHER INFORMATION: r=a or g
<220> FEATURE:
<221> NAME/KEY: variation
<222> LOCATION: (9)...(9)
<223> OTHER INFORMATION: s=c or g
<220> FEATURE:
<221> NAME/KEY: variation
<222> LOCATION: 11, 12, 13
<223> OTHER INFORMATION: y=c or t

<400> SEQUENCE: 41
atgrccdgst yyyctctcct                                                    20

<210> SEQ ID NO 42
<211> LENGTH: 18
<212> TYPE: DNA
<213> ORGANISM: artificial sequence
<220> FEATURE:
<223> OTHER INFORMATION: synthetic

<400> SEQUENCE: 42
ctcctcactc agggcaca                                                      18

<210> SEQ ID NO 43
<211> LENGTH: 20
<212> TYPE: DNA
<213> ORGANISM: artificial sequence
<220> FEATURE:
```

```
<223> OTHER INFORMATION: synthetic
<220> FEATURE:
<221> NAME/KEY: variation
<222> LOCATION: (18)...(18)
<223> OTHER INFORMATION: s=c or g

<400> SEQUENCE: 43
atggcctggg ctctgctsct                                                    20

<210> SEQ ID NO 44
<211> LENGTH: 19
<212> TYPE: DNA
<213> ORGANISM: artificial sequence
<220> FEATURE:
<223> OTHER INFORMATION: synthetic
<220> FEATURE:
<221> NAME/KEY: variation
<222> LOCATION: (11)...(11)
<223> OTHER INFORMATION: y=c or t
<220> FEATURE:
<221> NAME/KEY: variation
<222> LOCATION: (13)...(13)
<223> OTHER INFORMATION: s=c or g

<400> SEQUENCE: 44
atggcctgga ycsctctcc                                                     19

<210> SEQ ID NO 45
<211> LENGTH: 23
<212> TYPE: DNA
<213> ORGANISM: artificial sequence
<220> FEATURE:
<223> OTHER INFORMATION: synthetic
<220> FEATURE:
<221> NAME/KEY: variation
<222> LOCATION: 11, 16, 18, 21
<223> OTHER INFORMATION: y=c or t
<220> FEATURE:
<221> NAME/KEY: variation
<222> LOCATION: (15)...(15)
<223> OTHER INFORMATION: r=a or g
<220> FEATURE:
<221> NAME/KEY: variation
<222> LOCATION: (20)...(20)
<223> OTHER INFORMATION: m=a or c

<400> SEQUENCE: 45
tcaccatggc ytggrycycm ytc                                                23

<210> SEQ ID NO 46
<211> LENGTH: 22
<212> TYPE: DNA
<213> ORGANISM: artificial sequence
<220> FEATURE:
<223> OTHER INFORMATION: synthetic

<400> SEQUENCE: 46
tcaccatggc ctgggtctcc tt                                                 22

<210> SEQ ID NO 47
<211> LENGTH: 22
<212> TYPE: DNA
<213> ORGANISM: artificial sequence
<220> FEATURE:
<223> OTHER INFORMATION: synthetic
<220> FEATURE:
<221> NAME/KEY: variation
<222> LOCATION: (16)...(16)
<223> OTHER INFORMATION: m=a or c
<220> FEATURE:
<221> NAME/KEY: variation
```

<222> LOCATION: (19)...(19)
<223> OTHER INFORMATION: y=c or t

<400> SEQUENCE: 47
tcaccatggc ctggamtcyt ct                                          22

<210> SEQ ID NO 48
<211> LENGTH: 26
<212> TYPE: DNA
<213> ORGANISM: artificial sequence
<220> FEATURE:
<223> OTHER INFORMATION: synthetic

<400> SEQUENCE: 48
tcaccatggc ctgggctcca ctactt                                      26

<210> SEQ ID NO 49
<211> LENGTH: 20
<212> TYPE: DNA
<213> ORGANISM: artificial sequence
<220> FEATURE:
<223> OTHER INFORMATION: synthetic

<400> SEQUENCE: 49
tcaccatggc ctggactcct                                             20

<210> SEQ ID NO 50
<211> LENGTH: 23
<212> TYPE: DNA
<213> ORGANISM: artificial sequence
<220> FEATURE:
<223> OTHER INFORMATION: synthetic

<400> SEQUENCE: 50
tcaccatggc ctggatgatg ctt                                         23

<210> SEQ ID NO 51
<211> LENGTH: 22
<212> TYPE: DNA
<213> ORGANISM: artificial sequence
<220> FEATURE:
<223> OTHER INFORMATION: synthetic

<400> SEQUENCE: 51
taaatatggc ctgggctcct ct                                          22

<210> SEQ ID NO 52
<211> LENGTH: 22
<212> TYPE: DNA
<213> ORGANISM: artificial sequence
<220> FEATURE:
<223> OTHER INFORMATION: synthetic

<400> SEQUENCE: 52
tcaccatgcc ctgggctctg ct                                          22

<210> SEQ ID NO 53
<211> LENGTH: 22
<212> TYPE: DNA
<213> ORGANISM: artificial sequence
<220> FEATURE:
<223> OTHER INFORMATION: synthetic

<400> SEQUENCE: 53
tcaccatggc cctgactcct ct                                          22

<210> SEQ ID NO 54
<211> LENGTH: 30
<212> TYPE: DNA
<213> ORGANISM: artificial sequence
<220> FEATURE:
<223> OTHER INFORMATION: synthetic

<400> SEQUENCE: 54
cccaagctta ctggatggtg ggaagatgga                                    30

<210> SEQ ID NO 55
<211> LENGTH: 16
<212> TYPE: DNA
<213> ORGANISM: artificial sequence
<220> FEATURE:
<223> OTHER INFORMATION: synthetic

<400> SEQUENCE: 55
gtaaaacgac ggccag                                                   16

<210> SEQ ID NO 56
<211> LENGTH: 17
<212> TYPE: DNA
<213> ORGANISM: artificial sequence
<220> FEATURE:
<223> OTHER INFORMATION: synthetic

<400> SEQUENCE: 56
caggaaacag ctatgac                                                  17

<210> SEQ ID NO 57
<211> LENGTH: 440
<212> TYPE: DNA
<213> ORGANISM: artificial sequence
<220> FEATURE:
<223> OTHER INFORMATION: synthetic

<400> SEQUENCE: 57
gggcctgggc tctgctgctc ctcaccctcc tcactcaggg cacagggtcc tgggcccagt    60
ctgccctgac tcagcctccc tccgcgtccg ggtctcctgg acagtcagtc accatctcct   120
gcactggaac cagcagtgac gttggtggtt ataactatgt ctcctggtac caacagcacc   180
caggcaaagc ccccaaactc atgatttatg aggtcagtaa gcggccctca ggggtccctg   240
atcgcttctc tggctccaag tctggcaaca cggcctccct gaccgtctct gggctccagg   300
ctgaggatga ggctgattat tactgcagct catatgcagg cagcaacaat ttcgtcttcg   360
gaactgggac caaggtcacc gtcctagggg ctgatgctgc accaactgta tccatcttcc   420
caccatccag taagcttggg                                              440

<210> SEQ ID NO 58
<211> LENGTH: 441
<212> TYPE: DNA
<213> ORGANISM: artificial sequence
<220> FEATURE:
<223> OTHER INFORMATION: synthetic

<400> SEQUENCE: 58
atggcctggg ctctgctgct cctcaccctc tcactcagg gcacagggtc ctgggcccag    60
tctgccctga ctcagcctcc ctccgcgtcc gggtctcctg acagtcagt caccatctcc   120 tgcactggaa ccagcagtga cgttggtggt tataactatg tctcctggta ccaacagcac   180
ccaggcaaag cccccaaact catgatttat gaggtcacta agcggccctc agggtccct   240

| | |
|---|---|
| gatcgcttct ctggctccaa gtctggcaac acggcctccc tgaccgtctc tgggctccag | 300 |
| gctgaggatg aggctgatta ttactgcagc tcatatgcag gcagcaacaa ttatgtcttc | 360 |
| ggaactggga ccaaggtcac cgtcctaggg gctgatgctg caccaactgt atccatcttc | 420 |
| ccaccatcca gtaagcttgg g | 441 |

<210> SEQ ID NO 59
<211> LENGTH: 441
<212> TYPE: DNA
<213> ORGANISM: artificial sequence
<220> FEATURE:
<223> OTHER INFORMATION: synthetic

<400> SEQUENCE: 59

| | |
|---|---|
| atggcctggg ctctgctgct cctcaccctc ctcactcagg gcacagggtc ctgggcccag | 60 |
| tctgccctga ctcagcctcc ctccgcgtcc gggtctcctg gacagtcagt caccatctcc | 120 |
| tgcactggaa ccagcagtga cgttggtggt tataactatg tctcctggta ccaacagcac | 180 |
| ccaggcaaag cccccaaact catgatttat gaggtcagta agcggccctc aggggtccct | 240 |
| gatcgcttct ctggctccaa gtctggcaac acggcctccc tgaccgtctc tgggctccag | 300 |
| gctgaggatg aggctgatta ttactgcagc tcatatgcag gcagcaacaa ttatgtcttc | 360 |
| ggaactggga ccaaggtcac cgtcctaggg gctgatgctg caccaactgt atccatcttc | 420 |
| ccaccatcca gtaagcttgg g | 441 |

<210> SEQ ID NO 60
<211> LENGTH: 438
<212> TYPE: DNA
<213> ORGANISM: artificial sequence
<220> FEATURE:
<223> OTHER INFORMATION: synthetic

<400> SEQUENCE: 60

| | |
|---|---|
| atggcctggg ctctgctcct caccctcctc actcagggca cagggtcctg ggcccagtct | 60 |
| gccctgactc agcctccctc cgcgtccggg tctcctggac agtcagtcac catctcctgc | 120 |
| actggaacca gcagtgacgt tggtggttat aactatgtct cctggtacca acagcaccca | 180 |
| ggcaaagccc ccaaactcat gatttatgag gtcagtaagc ggccctcagg ggtccctgat | 240 |
| cgcttctctg gctccaagtc tggcaacacg gcctccctga ccgtctctgg ctccaggct | 300 |
| gaggatgagg ctgattatta ctgcagctca tatgcaggca gcaacaatta tgtcttcgga | 360 |
| actgggacca aggtcaccgt cctagggget gatgctgcac caactgtatc catcttccca | 420 |
| ccatccagta agcttggg | 438 |

<210> SEQ ID NO 61
<211> LENGTH: 438
<212> TYPE: DNA
<213> ORGANISM: artificial sequence
<220> FEATURE:
<223> OTHER INFORMATION: synthetic

<400> SEQUENCE: 61

| | |
|---|---|
| atggcctggg ctctgctgct cctcaccctc ctcactcagg gcacagggtc ctgggcccag | 60 |
| tctgccctga ctcagcctcc ctccgcgtcc gggtctcctg gacagtcagt caccatctcc | 120 |
| tgcactggaa ccagcagtga cgttggtggt tataactatg tctcctggta ccaacagcac | 180 |
| ccaggcaaag cccccaaact catgatttat gaggtcagta agcggccctc aggggtccct | 240 |

```
gatcgcttct ctggctccaa gtctggcaac acggcctccc tgaccgtctc tgggctccag    300
gctgaggatg aggctgatta ttactgcagc tcatatgcag gcagcaacaa tgtcttcgga    360
actgggacca aggtcaccgt cctaggggct gatgctgcac caactgtatc catcttccca    420
ccatccagta agcttggg                                                  438

<210> SEQ ID NO 62
<211> LENGTH: 441
<212> TYPE: DNA
<213> ORGANISM: artificial sequence
<220> FEATURE:
<223> OTHER INFORMATION: synthetic

<400> SEQUENCE: 62
atggcctggg ctctgctcct cctcaccctc ctcactcagg gcacagggtc ctgggcccag     60
tctgccctga ctcagcctcc ctccgcgtcc gggtctcctg gacagtcagt caccatctcc    120
tgcactggaa ccagcagtga cgttggtggt tataactatg tctcctggta ccaacagcac    180
ccaggcaaag cccccaaact catgatttat gaggtcagta gcggccctc aggggtccct    240 gatcgcttct ctggctccaa gtctggcaac acggcctccc tgaccgtctc tgggctccag    300
gctgaggatg aggctgatta ttactgcagc tcatatgcag gcagcaacaa tttatgtctc    360
ggaactggga ccaaggtcac cgtcctaggg gctgatgctg caccaactgt atccatcttc    420
ccaccatcca gtaagcttgg g                                              441

<210> SEQ ID NO 63
<211> LENGTH: 442
<212> TYPE: DNA
<213> ORGANISM: artificial sequence
<220> FEATURE:
<223> OTHER INFORMATION: synthetic

<400> SEQUENCE: 63
atggcctggg ctctgctgct cctcaccctc ctcactcagg gcacagggtc ctgggcccag     60
tctgccctga ctcagcctcc ctccgcgtcc gggtctcctg gacagtcagt caccatctcc    120
tgcactggaa ccagcagtga cgttggtggt tataactatg tctcctggta ccaacagcac    180
ccaggcaaag cccccaaact catgatttat gaggtcagta gcggccctc aggggtccct    240 gatcgcttct ctggctccaa gtctggcaac acggcctccc tgaccgtctc tgggctccag    300
gctgaggatg aggctgatta ttactgcagc tcatatgcag gcagcaacaa tttatgtctt    360
cggaactggg accaaggtca ccgtcctagg ggctgatgct gcaccaactg tatccatctt    420
cccaccatcc agtaagcttg gg                                             442

<210> SEQ ID NO 64
<211> LENGTH: 428
<212> TYPE: DNA
<213> ORGANISM: artificial sequence
<220> FEATURE:
<223> OTHER INFORMATION: synthetic

<400> SEQUENCE: 64
ccttcatttt ctccacaggt ctctgtgctc tgcctgtgct gactcagccc ccgtctgcat     60
ctgccttgct gggagcctcg atcaagctca cctgcaccct aagcagtgag cacagcacct    120
acaccatcga atggtatcaa cagagaccag ggaggtcccc ccagtatata atgaaggtta    180
agagtgatgg cagccacagc aagggggacg ggatccccga tcgcttcatg ggctccagtt    240
ctggggctga ccgctaccct accttctcca acctccagtc tgacgatgag gctgagtatc    300
```

```
actgtggaga gagccacacg attgatggcc aagtcggttg tgtcttcgga actgggacca    360
aggtcaccgt cctaggggct gatgctgcac caactgtatc catcttccca ccatccagta    420
agcttggg                                                             428
```

<210> SEQ ID NO 65
<211> LENGTH: 441
<212> TYPE: DNA
<213> ORGANISM: artificial sequence
<220> FEATURE:
<223> OTHER INFORMATION: synthetic

<400> SEQUENCE: 65

```
atgacctgct cccctctcct cctcacccTT ctcattcact gcacagggtc ctgggcccag     60
tctgtgttga cgcagccgcc ctcagtgtct gcggccccag gacagaaggt caccatctcc    120
tgctctggaa gcagctccaa cattgggaat aattatgtat cctggtacca gcagctccca    180
ggaacagccc ccaaactcct catttatgac aataataagc gaccctcagg gattcctgac    240
cgattctctg gctccaagtc tggcacgtca gccaccctgg gcatcaccgg actccagact    300
ggggacgagg ccgattatta ctgcggaaca tgggatagca gcctgagtgc ttatgtcttc    360
ggaactggga ccaaggtcac cgtcctaggg gctgatgctg caccaactgt atccatcttc    420
ccaccatcca gtgagcagtt a                                              441
```

<210> SEQ ID NO 66
<211> LENGTH: 441
<212> TYPE: DNA
<213> ORGANISM: artificial sequence
<220> FEATURE:
<223> OTHER INFORMATION: synthetic

<400> SEQUENCE: 66

```
atgacctgct cccctctcct cctcacccTT ctcattcact gcacagggtc ctgggcccag     60
tctgtgttga cgcagccgcc ctcagtgtct gcggccccag gacagaaggt caccatctcc    120
tgctctggaa gcagctccaa cattgggaat aattatgtat cctggtacca gcagctccca    180
ggaacagccc ccaaactcct catttatgac aataataagc gaccctcagg gattcctgac    240
cgattctctg gctccaagtc tggcacgtca gccaccctgg gcatcaccgg actccagact    300
ggggacgagg ccgattatta ctgcggaaca tgggatagca gcctgagtgc ggcttttttt    360
ggaactggga ccaaggtcac cgtcctaggg gctgatgctg caccaactgt atccatcttc    420
ccaccatcca gtgagcagtt a                                              441
```

<210> SEQ ID NO 67
<211> LENGTH: 345
<212> TYPE: DNA
<213> ORGANISM: artificial sequence
<220> FEATURE:
<223> OTHER INFORMATION: synthetic

<400> SEQUENCE: 67

```
cccgggcaga gggtcaccat ctcttgttct ggaagcagct ccaacatcgg aagtaatact     60
gtaaactggt accagcagct cccaggaacg gcccccaaac tcctcatcta tagtaataat    120
cagcggccct caggggtccc tgaccgattc tctggctcca gtctggcac ctcagcctcc    180 ctggccatca gtgggctcca gtctgaggat gaggctgatt attactgtgc agcatgggat    240
gacagcctga atggttatgt cttcggaact gggaccaagg tcaccgtcct agggctgat    300
```
gctgcaccaa ctgtatccat cttcccacca tccagtgagc agtta 345

<210> SEQ ID NO 68
<211> LENGTH: 432
<212> TYPE: DNA
<213> ORGANISM: artificial sequence
<220> FEATURE:
<223> OTHER INFORMATION: synthetic

<400> SEQUENCE: 68
atggcctgga cccctctcct gctccccctc ctcactttct gcacagtctc tgaggcctcc 60
tatgagctga cacagccacc ctcggtgtca gtgtccccag acaaacggc caggatcacc 120
tgctctggag atgcattgcc aaaaaaatat gcttattggt accagcagaa gtcaggccag 180
gcccctgtgc tggtcatcta tgaggacagc aaacgaccct ccgggatccc tgagagattc 240
tctggctcca gctcagggac aatggccacc ttgactatca gtggggccca ggtggaggat 300
gaagctgact actactgtta ctcaacagac tacagtggta atcatgtctt cggaactggg 360
accaaggtca ccgtcctagg ggctgatgct gcaccaactg tatccatctt cccaccatcc 420
agtgagcagt ta 432

<210> SEQ ID NO 69
<211> LENGTH: 426
<212> TYPE: DNA
<213> ORGANISM: artificial sequence
<220> FEATURE:
<223> OTHER INFORMATION: synthetic

<400> SEQUENCE: 69
atggcctgga ctcctctctt tctgttcctc ctcacttgct gcccagggtc caattcccag 60
gctgtggtga ctcaggagcc ctcactgact gtgtccccag agggacagt cactctcacc 120
tgtggctcca gcactggagc tgtcaccagt ggtcattatc cctactggtt ccagcagaag 180
cctggccaag cccccaggac actgatttat gatacaagca caaaactc ctggacacct 240
gcccggttct caggctccct ccttggggc aaagctgccc tgacccttc gggtgcgcag 300
cctgaggatg aggctgagta ttactgcttg ctctcctata gtggtgctta tgtcttcgga 360
actgggacca aggtcaccgt cctaggggct gatgctgcac caactgtatc catcttccca 420
ccatcc 426

<210> SEQ ID NO 70
<211> LENGTH: 331
<212> TYPE: DNA
<213> ORGANISM: artificial sequence
<220> FEATURE:
<223> OTHER INFORMATION: synthetic

<400> SEQUENCE: 70
agtggtcctg ggacagacgg ccaggattac ctgtggggga acaacattg gaagtaaaaa 60
tgtgcactgg taccagcaga agccaggcca ggccctgtg ctggtcatct atagggataa 120
caaccggccc tctgggatcc ctgagcgatt ctctggctcc aactcgggga cacggccac 180
cctgaccatc agcagagccc aagccgggga tgaggctgac tattactgtc aggtgtggga 240
cagcagcact tatgtcttcg gaactgggac caaggtcacc gtcctagggg ctgatgctgc 300
accaactgta tccatcttcc caccatccag t 331

<210> SEQ ID NO 71
<211> LENGTH: 417

<212> TYPE: DNA
<213> ORGANISM: artificial sequence
<220> FEATURE:
<223> OTHER INFORMATION: synthetic

<400> SEQUENCE: 71

```
actcctctcc tcctcctgtt cctctctcac tgcacaggtt ccctctcgca ggctgtgctg    60
actcagccgt cttccctctc tgcatctcct ggagcatcag ccagtctcac ctgcaccttg   120
cgcagtggca tcaatgttgg tacctacagg atatactggt accagcagaa gccagggagt   180
cctccccagt atctcctgag gtacaaatca gactcagata agcagcaggg ctctggagtc   240
cccagccgct tctctggatc caaagatgct tcggccaatg cagggatttt actcatctct   300
gggctccagt ctgaggatga ggctgactat tactgtatga tttggcacag cagcgcttat   360
gtcttcggaa ctgggaccaa ggtcaccgtc ctaggggctg atgctgcacc aactgta      417
```

<210> SEQ ID NO 72
<211> LENGTH: 393
<212> TYPE: DNA
<213> ORGANISM: artificial sequence
<220> FEATURE:
<223> OTHER INFORMATION: synthetic

<400> SEQUENCE: 72

```
tttctgttcc tcctcacttg ctgcccaggg tccaattctc agactgtggt gactcaggag    60
ccctcactga ctgtgtcccc aggagggaca gtcactctca cctgtgcttc cagcactgga   120
gcagtcacca gtggttacta tccaaactgg ttccagcaga aacctggaca agcacccagg   180
gcactgattt atagtacaag caacaaacgc tcctggaccc ctgcccggtt ctcaggctcc   240
ctccttgggg gcaaagctgc cctgacactg tcaggtgtgc agcctgagga cgaggctgag   300
tattactgcc tgctctacta tggtggtgct tatgtcttcg gaactgggac caaggtcacc   360
gtcctagggg ctgatgctgc accaactgta tcc                                393
```

<210> SEQ ID NO 73
<211> LENGTH: 417
<212> TYPE: DNA
<213> ORGANISM: artificial sequence
<220> FEATURE:
<223> OTHER INFORMATION: synthetic

<400> SEQUENCE: 73

```
atggcctggg ctctgctgct cctcactctc ctcactcagg acacagggtc ctgggcccag    60
tctgccctga ctcagcctgc ctccgtgtct gggtctcctg gacagtcgat caccatctcc   120
tgcactggaa ccagcagtga tgttgggagt tataaccttg tctcctggta ccaacagcac   180
ccaggcaaag cccccaaact catgatttat gagggcagta gcggccctc aggggtttct   240
aatcgcttct ctggctccaa gtctggcaac acggcctccc tgacaatctc tgggctccag   300
gctgaggacg aggctgatta ttactgctgc tcatatgcag gtagtagcac ttatgtcttc   360
ggaactggga ccaaggtcac cgtcctaggg gctgatgctg caccaactgt atccatc      417
```

<210> SEQ ID NO 74
<211> LENGTH: 348
<212> TYPE: DNA
<213> ORGANISM: artificial sequence
<220> FEATURE:
<223> OTHER INFORMATION: synthetic

<400> SEQUENCE: 74

```
cagtctgccc tgactcagcc tgcctccgtg tctgggtctc ctggacagtc gatcaccatc    60
tcctgcactg gaaccagcag tgacgttggt ggttataact atgtctcctg gtaccaacag   120
cacccaggca aagcccccaa actcatgatt tatgaggtca gtaatcggcc ctcaggggtt   180
tctaatcgct tctctggctc caagtctggc aacacggcct ccctgaccat ctctgggctc   240
caggctgagg acgaggctga ttattactgc agctcatata caagcagcag cacttatgtc   300
ttcggaactg ggaccaaggt caccggcctg ggggctgatg ctgcacca                348
```

<210> SEQ ID NO 75
<211> LENGTH: 20
<212> TYPE: DNA
<213> ORGANISM: Artificial Sequence
<220> FEATURE:
<223> OTHER INFORMATION: synthetic
<400> SEQUENCE: 75

```
aacaaccgag ctccaggtgt                                                20
```

<210> SEQ ID NO 76
<211> LENGTH: 19
<212> TYPE: DNA
<213> ORGANISM: Artificial Sequence
<220> FEATURE:
<223> OTHER INFORMATION: synthetic
<400> SEQUENCE: 76

```
agggcagcct tgtctccaa                                                 19
```

<210> SEQ ID NO 77
<211> LENGTH: 20
<212> TYPE: DNA
<213> ORGANISM: Artificial Sequence
<220> FEATURE:
<223> OTHER INFORMATION: synthetic
<400> SEQUENCE: 77

```
cctgccagat tctcaggctc                                                20
```

<210> SEQ ID NO 78
<211> LENGTH: 20
<212> TYPE: DNA
<213> ORGANISM: Artificial Sequence
<220> FEATURE:
<223> OTHER INFORMATION: synthetic
<400> SEQUENCE: 78

```
catcacaggg gcacagactg                                                20
```

<210> SEQ ID NO 79
<211> LENGTH: 19
<212> TYPE: DNA
<213> ORGANISM: Artificial Sequence
<220> FEATURE:
<223> OTHER INFORMATION: synthetic
<400> SEQUENCE: 79

```
gatttgctga gggcagggt                                                 19
```

<210> SEQ ID NO 80
<211> LENGTH: 21
<212> TYPE: DNA
<213> ORGANISM: Artificial Sequence
<220> FEATURE:
<223> OTHER INFORMATION: synthetic

<400> SEQUENCE: 80
ccccaagtct gatccttcct t                                              21

<210> SEQ ID NO 81
<211> LENGTH: 20
<212> TYPE: DNA
<213> ORGANISM: Artificial Sequence
<220> FEATURE:
<223> OTHER INFORMATION: synthetic

<400> SEQUENCE: 81
gctgaccaac gatcgcctaa                                                20

<210> SEQ ID NO 82
<211> LENGTH: 19
<212> TYPE: DNA
<213> ORGANISM: Artificial Sequence
<220> FEATURE:
<223> OTHER INFORMATION: synthetic

<400> SEQUENCE: 82
taagcgccac actgcacct                                                 19

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
cctgccagat tctcaggctc cctg                                           24

<210> SEQ ID NO 84
<211> LENGTH: 23
<212> TYPE: DNA
<213> ORGANISM: Artificial Sequence
<220> FEATURE:
<223> OTHER INFORMATION: synthetic

<400> SEQUENCE: 84
ctgattggag acaaggctgc cct                                            23

<210> SEQ ID NO 85
<211> LENGTH: 30
<212> TYPE: DNA
<213> ORGANISM: Artificial Sequence
<220> FEATURE:
<223> OTHER INFORMATION: synthetic

<400> SEQUENCE: 85
ccttcatact cttgcatcct cccttctcca                                     30

<210> SEQ ID NO 86
<211> LENGTH: 35
<212> TYPE: DNA
<213> ORGANISM: Artificial Sequence
<220> FEATURE:
<223> OTHER INFORMATION: synthetic

<400> SEQUENCE: 86
ttccttctct tctgtgactc aattatttgt ggaca                               35

<210> SEQ ID NO 87

```
<211> LENGTH: 159
<212> TYPE: DNA
<213> ORGANISM: Artificial Sequence
<220> FEATURE:
<223> OTHER INFORMATION: synthetic

<400> SEQUENCE: 87
tctggcacct cagcctccct ggccatcact gggctccagg ctgaggatga ggctgattat      60
tactgccagt cctatgacag cagcctgagt ggttctgtgt tcggaggagg cacccggctg     120
accgccctcg gggctgatgc tgcaccaact gtatccatc                            159

<210> SEQ ID NO 88
<211> LENGTH: 159
<212> TYPE: DNA
<213> ORGANISM: Artificial Sequence
<220> FEATURE:
<223> OTHER INFORMATION: synthetic

<400> SEQUENCE: 88
tctggcacct cagcctccct ggccatcact gggctccagg ctgaggatga ggctgattat      60
tactgccagt cctatgacag cagcctgagt ggttatgtct tcggaactgg gaccaaggtc     120
accgtcctag gggctgatgc tgcaccaact gtatccatc                            159

<210> SEQ ID NO 89
<211> LENGTH: 159
<212> TYPE: DNA
<213> ORGANISM: Artificial Sequence
<220> FEATURE:
<223> OTHER INFORMATION: synthetic

<400> SEQUENCE: 89
tctggcacct cagcctccct ggccatcagt gggctccagt ctgaggatga ggctgattat      60
tactgtgcag catgggatga cagcctgaat ggtgctgtgt tcggaggagg cacccagctg     120
accgccctcg gggctgatgc tgcaccaact gtatccatc                            159

<210> SEQ ID NO 90
<211> LENGTH: 159
<212> TYPE: DNA
<213> ORGANISM: Artificial Sequence
<220> FEATURE:
<223> OTHER INFORMATION: synthetic

<400> SEQUENCE: 90
tctggcacct cagcctccct ggccatcagt gggctccggt ccgaggatga ggctgattat      60
tactgtgcag catgggatga cagcctgagt ggtcgggtgt tcggcggagg gaccaagctg     120
accgtcctag gggctgatgc tgcaccaact gtatccatc                            159

<210> SEQ ID NO 91
<211> LENGTH: 153
<212> TYPE: DNA
<213> ORGANISM: Artificial Sequence
<220> FEATURE:
<223> OTHER INFORMATION: synthetic

<400> SEQUENCE: 91
tcggggaaca cggccaccct gaccatcagc agagcccaag ccggggatga ggctgactat      60
tactgtcagg tgtgggacag cagcactgct gtgttcggag gaggcaccca gctgaccgcc     120
ctcggggctg atgctgcacc aactgtatcc atc                                  153
```

```
<210> SEQ ID NO 92
<211> LENGTH: 156
<212> TYPE: DNA
<213> ORGANISM: Artificial Sequence
<220> FEATURE:
<223> OTHER INFORMATION: synthetic

<400> SEQUENCE: 92
tcagggacaa tggccacctt gactatcagt ggggcccagg tggaggatga agctgactac      60
tactgttact caacagacag cagtggtaat gctgtgttcg gaggaggcac ccagctgacc     120
gccctcgggg ctgatgctgc accaactgta tccatc                              156

<210> SEQ ID NO 93
<211> LENGTH: 159
<212> TYPE: DNA
<213> ORGANISM: Artificial Sequence
<220> FEATURE:
<223> OTHER INFORMATION: synthetic

<400> SEQUENCE: 93
tcagggacaa tggccacctt gactatcagt ggggcccagg tggaggatga agctgactac      60
tactgttact caacagacag cagtggtaat cataggtgt tcggcggagg gaccaagctg      120
accgtcctag gggctgatgc tgcaccaact gtatccatc                            159

<210> SEQ ID NO 94
<211> LENGTH: 159
<212> TYPE: DNA
<213> ORGANISM: Artificial Sequence
<220> FEATURE:
<223> OTHER INFORMATION: synthetic

<400> SEQUENCE: 94
tctggcacct cagcctccct ggccatcact gggctccagg ctgaggatga ggctgattat      60
tactgccagt cctatgacag cagcctgagt ggttatgtct tcggaactgg gaccaaggtc    120
accgtcctag gggctgatgc tgcaccaact gtatccatc                            159

<210> SEQ ID NO 95
<211> LENGTH: 159
<212> TYPE: DNA
<213> ORGANISM: Artificial Sequence
<220> FEATURE:
<223> OTHER INFORMATION: synthetic

<400> SEQUENCE: 95
gatgcttcgg ccaatgcagg gattttactc atctctgggc tccagtctga ggatgaggct      60
gactattact gtatgatttg gcacagcagc gctgtggtat tcggcggagg gaccaagctg     120
accgtcctag gggctgatgc tgcaccaact gtatccatc                            159

<210> SEQ ID NO 96
<211> LENGTH: 153
<212> TYPE: DNA
<213> ORGANISM: Artificial Sequence
<220> FEATURE:
<223> OTHER INFORMATION: synthetic

<400> SEQUENCE: 96
cttgggggca aagctgccct gacactgtca ggtgtgcagc ctgaggacga ggctgagtat      60
tactgcctgc tctactatgg tggtgctcgg gtgttcggcg gagggaccaa gctgaccgtc    120
ctaggggctg atgctgcacc aactgtatcc atc                                 153
```

<210> SEQ ID NO 97
<211> LENGTH: 153
<212> TYPE: DNA
<213> ORGANISM: Artificial Sequence
<220> FEATURE:
<223> OTHER INFORMATION: synthetic

<400> SEQUENCE: 97

| | | | | | |
|---|---|---|---|---|---|
| cttgggggca | aagctgccct | gacccttcg | ggtgcgcagc | ctgaggatga | ggctgagtat | 60 |
| tactgcttgc | tctcctatag | tggtgctcga | gtattcggcg | agggaccaa | gctgaccgtc | 120 |
| ctaggggctg | atgctgcacc | aactgtatcc | atc | | | 153 |

<210> SEQ ID NO 98
<211> LENGTH: 165
<212> TYPE: DNA
<213> ORGANISM: Artificial Sequence
<220> FEATURE:
<223> OTHER INFORMATION: synthetic

<400> SEQUENCE: 98

| | | | | | |
|---|---|---|---|---|---|
| tcaggcctga | atcggtacct | gaccatcaag | aacatccagg | aagaggatga | gagtgactac | 60 |
| cactgtgggg | cagaccatgg | cagtgggagc | aacttcgtgt | ctgtgttcgg | aggaggcacc | 120 |
| cagctgaccg | ccctcgggc | tgatgctgca | ccaactgtat | ccatc | | 165 |

<210> SEQ ID NO 99
<211> LENGTH: 164
<212> TYPE: DNA
<213> ORGANISM: Artificial Sequence
<220> FEATURE:
<223> OTHER INFORMATION: synthetic

<400> SEQUENCE: 99

| | | | | | |
|---|---|---|---|---|---|
| tctggcacgt | cagccaccct | gggcatcacc | ggactccaga | ctggggacga | ggccgattat | 60 |
| tactgcggaa | catgggatag | cagcctgagt | gctggccccg | ggtgttcggc | ggagggacca | 120 |
| agctgaccgt | cctagggggct | gatgctgcac | caactgtatc | catc | | 164 |

<210> SEQ ID NO 100
<211> LENGTH: 22800
<212> TYPE: DNA
<213> ORGANISM: Artificial Sequence
<220> FEATURE:
<223> OTHER INFORMATION: synthetic

<400> SEQUENCE: 100

| | | | | | |
|---|---|---|---|---|---|
| aagctctaaa | actacaaact | gctgaaagat | ctaatgacta | ggacagccta | gtaattttca | 60 |
| tagggggcata | aatgtgaaac | gccttgtgca | tcgtagaaga | aagcagaaga | gaaagcattc | 120 |
| ccaatttctt | aactgccttt | tacctatatt | aatcagtaat | atactggctt | ttacctctgt | 180 |
| taatcataat | aaacaaattc | tcaataaatt | ttatcgatac | tcttcaatgc | ctgctcagca | 240 |
| acattttccg | aaggcagctc | aagatattaa | ataactcata | agggccaacc | tcctattgca | 300 |
| gcattctttg | ggatttaacc | agtttcccaa | gactcttttc | acaatgttaa | gatgttagaa | 360 |
| atagatccaa | aactaggtga | tatatcccct | agtaaaactg | tgaggtcaaa | cttgtctggc | 420 |
| taatgcttcc | atttaaaaat | ttctctttct | tgatccttca | ttgtatgtac | acaataaatc | 480 |
| agggggaaaac | tttaactgag | tgaatcaaag | tattctcatt | attataatag | gagcttcaca | 540 |
| cacacacaaa | aaaatcaatt | ctattactct | cagcctcagt | tcctaaagcc | aagttaaagt | 600 |
| cctgttctaa | gatcattgtt | gcatgaccat | atgtattcca | ggtctaatct | aaactgtgga | 660 |

```
taaatcccag caggacatta gagattttg tgagagtaag catataggat tcagggttta     720
tgagctttag atttttcttg tcaaaatgaa tgagagttgc catatctaaa aattattccc    780
agataaataa aattcactac ctagaattaa tttatgcata taagtagaaa tgctatctcc    840 cttttacca tccaaagtgg aaagcctcat ggaactagaa attaatatta gaaaaatcag     900
ttaataaaag tatgtcattt catcaattca ataagttata atagcaaaaa accataataa    960
attatcactt aaatgtcaat acatttataa actatggtac ataaatagga tattgaataq   1020 ccattgatgc tcctgatgaa aattagcagg cagtgataaa tgataaatat gaagcacatg   1080
tcaataaata aaataagttt tatgtaattt aggagaaaat ggtgataatg acacaaaatg   1140
tgaattatgg atgcatctat aaaattcttt gtacatttgt gaattgtaaa tatttatctt   1200
agagacatta ttactttgta tatgttccat ttgctcacct atatgtccca gtctccttac   1260
aaatgctatg gccaaagaaa taggcataca tacatccttt gcaggctgag gcaggaaaaa   1320
gatcttacgg aattttccag tctatccttt atctgtataa gcaacttaag aggccatgtg   1380
ctccaaatgg tgcaaataca agatggtaga gcctctgtct gcctggatcc ttgagtggct   1440
gcatggagca gagcaccttt ctggccctgg tgaagattgt agcatgagca agatataagc   1500
atttgttgga gctaggccat gagatttggg gcagtggtat aacctaccct attatggaaa   1560
atataaatac acaaaacaga aaagagagag agaagtgaga gaagactgtg agagaagtgc   1620
atgagagaag actgtgtttt gttcatttcc tataatccta tatcaccatg ggatcctgtg   1680
ccttctggtg atcaaactaa tgttctacag ctccaaagaa gaatgctcgc ctaacgtctc   1740
cattccaatg acctagagac taaaagccaa aaagaaccctt agaaattatc tattgcattc   1800
tttgatgtaa ggaaatatct tagagggcac agatagaaat atcttaaccc aggtcactta   1860
gttcgtggca gagctgaggc taaaaccagg cctttttgact cctaattttg tgctctttac   1920
accttctcac atcacttctc caacccaaag tctagcagaa aaggctaaaa taagatatat   1980
gcatagattt gctattataa gtccatgtac ttcctcagac gctttaagat ggggcttctc   2040
atggttcaca ataagcagca gagggaagtg aataactatc ttcgtctccc ctactgctat   2100
ttgtgcagtt tgaagcttat ctcttaaatc atgttttctt ctcgtagtaa atactacaac   2160
ttgtgccttt tatgtgtgta taaattttaa tataattttt ttccatgaac cattcaagta   2220
aaatggacac tccaaaaaga tgttcaataa ggttacatgg cttcacattg cccctctac    2280 accatcttgt ggagctacac attcacctca cccaaatttg agaaaataa tcaagaaaat    2340 gactctcact agcagtgaga ccaagtccat aagcactaat gtcatcagtg cacactgcag   2400
cctcatgctg ccaagcatgt tttgggcgta tccctggact ggtttggtga catgatcaaa   2460
ggtacatttt ccacctgcat agccccatcc tggatctata gccttccttg tgtctttgtg   2520
aacaacctag tgtgaactca agtatgaga cagatctcaa ttaatttaga aagtttattt     2580
tcccaagatt aaggacaagc ccatgataaa gcctccagag gtcctgatat atgtgcccaa   2640
gggggtcggg gcacagcttg tgttatacat ttagggag acaagaaaca tcaatcgata     2700
tgtagaagat gtgcatcgct ttggtctgga aaggtgtgac aactcaaggc agggaagggg   2760
gcttcctgct ggggttgcat tgttttgagt ctctgatcag ccttttcacat gtgaaaggca   2820 ggtagagaaa tagtcattta tgccttagtc tggcttattg aaacagtagg gcagaagaag   2880
cattgcatat gcatttgtct gaagtgaaca gagggatgac tttgagctct gtccttttctt  2940 tgtccacaag gaattacctt gtgggcaaat tgtgagggag gtatgtagct ttttttttctt  3000
```

```
tgtagctatc ttatttagga ataaaatggg aggcaggttt gcctgatgca attcccagct    3060
tgactttccc ttttggctta gtgattttg gggtcctgag gtttattttt tctttcacat    3120
tagtataact acttttcttt ttctaattcc ttttctactt gtatgtgtta cagctgactt    3180
atgttacttg caaaaagaat tctgactaat gcaccatctg actagaaggc agggttcttc    3240
gatgataacg aatcctccag aatctagtaa acagaattgc ctgaaaaaga ggtgggtgtc    3300
ttcttgggga atttctcatg gcaatgaatg gcaactggcc aaaggattta tgaccagact    3360
gagctctctt ttatctattc tgttactcac caagacctat tagggtttgt gctccacagg    3420
gacactggtt tctaagttct agggttaaac agtccactcc caggcccacc acaccatacc    3480
ctcctgacat ctggtgaaca gcaataaaat tgtttcttat tctgaaaatc ctccaatact    3540
tccaccatcc ccaaaaatgc agtggaggag gagagaaaat gaattgttcc attagagaac    3600
acaatatcca ttatattatt cttggccttt gagatacctt acaaaacaaa tacaaaaaaa    3660
gtcccaattt aacatctttt aataatcttt acaaaacaga acacatctcc tttcttgata    3720
atagtcaaga ggctcagtgg caactgtggt gaaaagtgtc agattctggt catgtttcaa    3780
aggtagaaaa aatagaattt gttaacatat tggatgtgag gcgtgggaga aacgtgaaat    3840
caaggtggtt gcaagtgttt aacctgagca actagagaat ttggaaggac attttctgag    3900
atggggaagg caggcgggaa tcagggatta gagttgaaca tattagacat ttgagatgcc    3960
tgctagacct ctaattggca atatcccttg gacaggtgga tgaatatgcg tgattctgga    4020
gttcgggaaa tagtccgggt ggagatgcaa atttgggaaa cagggcgagg ttactagcaa    4080
tgagttaaat caatgaaggc aggctgggac ctggcaggta acccaacaag tagaggtcga    4140
agagatgaga agaaaacagc acaggagact tagaagcagt ggtcaggagg aaggagttga    4200
accaagaaag tgatgtccca gagccaacaa aataaggatt tcttttctgt ttacaaatgt    4260
aaaattaaaa ggtttaataa aaagaaaatt tactttatg gttggttgtt attaagtggt    4320
ccaaacactg tctcctattt gtagaatcag aactctctca tggcagtaga aaatttggaa    4380
agttactttt taaaggtgt gtgcactgct gccctttgct ggtcaagttt atgcactgca    4440
aattccaagg acgattgctc gtcagctttt ctcctttaaa atagctcagg ctgtacaagc    4500
tagaaagaac ctcgcaagat attccttcca acatttgcat ttgacttatg ggaagtgcag    4560
gttcagccag aaaagttgtg tgcaaggccg tttatgtaag tttatcagac ctgattctta    4620
cggctcttcc cattgtttcg agcctccctt ccattcactt cccgctcata cgcgaccaag    4680
tataggacag gagtagttat tctgcacttt atagcagctc cactgtctgg cactctgatg    4740
ttctttaatt acaagcttta tgacagtgat tctcaacctg ctccactgcc tccacctagt    4800
ggcagaaaga agaaaatgtg tgtaactcgg gagtctctgg tctgaaagct ccggggtatc    4860
atttcttcaa agtcttgagc ttgttttgt ttgtatttat ttatttattt gttttagaga    4920
caaggtctcg cactgcactc cagcctggga gacagagcga gacaattcag gatctatcta    4980
gtgaataaag agatatcagt aatgactgtt ttatattgtg gctgtagcgc attcgaggga    5040
taattcgatt ctgttctgct ttcgaatgca tggctcactg taacctccaa ctcccgggct    5100
caagcgatcc tcctacctca gcttctccag tagttgagct tgatttattt taagtttca    5160 taaaattttg gcatttcttt ccacaatatg gccatgtgtg ctttactata aatatttc    5220 atcacaaaat ttcatcgct ggaaatcccc ataagccagt ttgagaaaca caacccaaga    5280
aagcagaaca gactcaaatt atcccttaaa tccccttaa ccacaaatat aaaacagtcc    5340
gtgactgggc gtgttggctt acacctgtaa tcccagcact ttgggaggcc aaggcgggtg    5400
```

```
gattacttga gctcaggagt tcaagaccag cctggccaac atggtgaaac cccgtccta    5460
ttaaaaatac aaaattattc aggagttgtg gcaggcagtt gtaatcccag ctacttggga   5520
ggctgaggca ggagaatcac ttgaacccag gaggtggagg ttgtagtgag ccaagattgt   5580
gccagtgcac tccagcctgg gcaacagagc gagacttcca tcttaaaaaa aaaaaattaa   5640
gtaaataaaa tataaaaaaa taaagcagtc cctattgata tctctttatt cactaaatca   5700
acctggaatt gacctgaatt ctgattttt tttcatcatg gattttttgc attaattttg    5760
attgtttaaa tattgcatta aaatattatt tatcttgact actgagtttg cgggacctcc   5820
ttaaaattta tgaccaaggc aatgcctcac tcactcgcct taccataatc tgggccacat   5880
atcaggggct ccaatagcaa gcaacatgac ttttgaacag ctaagacttc tctcttcact   5940
gtgaagacca gatgggccct gcaaacagtg taacctctac atgaaaatgc acgagattcc   6000
aactacaacc aggcacaaaa gactctgatg gtgaagtccc agccctccaa gtcccaactt   6060
cctgaaggga aagagcaccc caagttctga ccagaggcca gagtcataac gaagatggaa   6120
tgtgagcttg acatagaagg ggtggtagca cctggctcag taatgaagag gctttcggtc   6180
ctgaaggaag agctcagcac attcaaagat tagaagggag gtcccagtca taggagcagg   6240
gaaggagaga aggcccaata agaaacacag acaggaggga ggggtcaggg caagatcata   6300
ctggaaacaa ctagagagct aataaaagtc acagtgccca gtccccacat ggaccagact   6360
cttcggaatc tctaggcatc aatttgggca ccagtagttt tcaaagttct ccagaagatt   6420
ctatgcacac cagccaaggg tgggaaccac aggtgttggc ctaggatca tgacaatgag    6480
tttctaagtg caataagaaa cctccagaga gtttaagcag gggaataatt tgatttgttt   6540
cttgtttgtg atttttaaag atcagtctgg ttactgtgtg taagacaata atccagaaaa   6600
tctgttgctc atgaaccaca tatctgtaaa tttgcttccc ctgtaactgg atctaaccaa   6660
caaaaattag tacttactaa gaaattacat gcccagggac tatgctaagt aattcataaa   6720
cactatttta tttactcctc acagcaagtt tataagagaa acgttattat ttccacattt   6780
cggatgagaa atttgaggct tggggaaagt taagtaattt acctaatgtc acacccagtt   6840
cataagatgc agagttaaga ttctaattct gtgtctaagt tgatgctcca tcaaacacac   6900
cacgcctcca actaggaagc aacatgctgg ccagaggatg ctgtcatcaa gtttacagaa   6960
tggttagatt tctaggcaca gatgaataaa tcaacatgtt ggtttgcaat agaatgaatc   7020
tatccagctc tgaatttgca tccaagggtt tgtgagcaca caagtctaaa agtgtggcct   7080
cagctctgct aacttcatca aggtgaatac ctaggaggcc accctctgag accaccagat   7140
ggacagtcca ccatctgttt acagatggta aagccacata ccagctttgc catctgatgt   7200
tctctattca cattcaacat ttatacaaga aatagtcata tggatccttt tcaatagaca   7260
gtactgggga aattgaattg ccatatgcag aagaatggaa ctagacctct atctctcacc   7320
aaatacaaaa gttaactcaa gacagattaa agacttacat ataagacctg taactacaaa   7380
aacactagaa gaaaacctag ggaaaatgct tctggaatta atctaggtga agaactcagg   7440
actaagatat caaagcaca agcaccaaaa caaaaataga caaacaggac ttaattaaac    7500
tagaacgctt ctgaacagca agagaaataa tcaatagagt gaacagataa tctgcagaat   7560
gggtgaaaat atttgcaaac tatgcatcct acagggaaat aatgtccaga atttagaagg   7620
aactcaaaca attcaacaac aacagcaaaa taacccacc aaaaaagtgg gcaaaggaca    7680
tgaatagaca ttttttcaaaa gaaggtatat gatatggttt ggctctgtgt ctccacccag   7740
```

```
atctcacctt aaattgtaat aatccccaca tatcatggga gagacccggt gggaggtaat    7800
tgaatcatgg gggcaggttt gtcccatgct gttctcatga tactgaataa gtcctatgag    7860
atctgatgat tttataaagg ggagttcccc tgcacacact ctcttgcctg cctccatgta    7920
atatgtgcct ttgcttctcc tttgccttct gccatgattg tgaggcctct ccagccatat    7980
ggaactgagt caattaaacc acttttctt tgtaaattac ccaatcttgg gtatgtcttt    8040
attagcagca taagaacaga ctaatacagt gtacaaatgg ccaagaagcg tacaaaaaac    8100
aaaatgctca aatcactaat cactagagaa tcgcaagtta aaaccacaat gagatattat    8160
cttacagcag tcagaatgcc tattattaaa acaccaaaaa ataacatgtt ggcaaggatg    8220
cagagaaaag ggaatactta cacattatta gtgggaatgt aaactagtac agcttctgtg    8280
gaaaacacta tggagatttc tcaaagaact agaaatagaa ctaccatgtg gttcagcaat    8340
accacaactg ggtatctacc caagggaaa taaattatta tataaaaag atatctgcac    8400 tcacttgttt attgcagcac tattcacaat agcaaagata tggaatcaac ccaagtgtcc    8460
atcaacagat gattggataa agaaaacgtg gtgtgtgtgt gtgtgtgtgt gtgtgtgtat    8520
acacatacca caatgaaata ctattcagct ataagaaaaa gaatgaaatc atgtcttttg    8580
cagcaatgtg gttggaactg gaggccatta tcttaagtgg ataattcaaa aacagaaggt    8640
caaatgtcac atgttctcac ttataagtgg gagctaaatg atgtgtacac atggacatag    8700
agtgtggtat gataaacact ggagattgag atgggtggaa gggtggaagg aggttgagtg    8760
atgagaaaat actaaatgga tacaatatac atgattcagg cgatagatac actaaaagcc    8820
cagacttcac cactcacag tatagctatg tagcaaaatt gcacctgtat tgcttaaatt    8880
tatacaagta aaaaaagat cgtacgaatt ctgttttta ttctctatga aattactact    8940
gagagtatta tccaatgccg tttctatgca gtgcccccaa tattatccat ttagcagctc    9000
ctatgcaatg ccccaagata gaaattgtct tcaactttta tcccaggaaa accttcagtc    9060
acacgtagaa actagaaatt tttcccctag atgaaagtta tgtaacataa cacattatct    9120
tcatttagtc ggtttccaag aagctcagaa ccagatttta tgttcaatca aaaactgctt    9180
attttaagtg aggtttactg aggtataaat tacaataaaa gccaccttt cgtgtatatt    9240 tctataagtt ttggcaaatg catagctgtg taaccacaac cacattcaag atataggaca    9300
agtccctcat cctttaaagt tcctttatgc cccttccttc accccagccc ttggcaacca    9360 ctggttttg tctgatccaa tcgtttgcct cttcctgaat gtcatgtaaa tagagccatg    9420
caatgtgaag ccttttgagt ctggcttgt tcacttgttc acttaggaga atgcatttga    9480
gattcatctt tgctgtttcg tgtagcacta gttcactgtc tattgttgag tagtattcca    9540
ttgtgtggat atgccacaga ttgtttatct agttaacaat ttaaagccat ttggtcattt    9600
ctaattttta gctgctaaga ataaagttgc tgtaagcttt ccaatgcagg ttttgtgtg    9660 aactcaggat ttcatttcgc ttgggtaaat tcctagctt gggactgctg agtcatctgg    9720
taggtgtatg ttgaacttta taagaaactg ccaaactgtt ttccaaagtt gctgtgctct    9780
tttgcactcc catcagcagt gaatgagggt tccacttgct cgagcctagt attttaactt    9840
cactatatac cttctttgat gacatatcct ttcaaatttt tggtcaagtt tttattgggg    9900
tgttgttact atggactgtg agagttcttt gtatattctg catatgattt ttttctcaca    9960
tttgtgtttt atgaatatgt tctcccaatg tgtggcgcct tttatttct taacgtgcca    10020 tgtgaagagc agaagtttaa ttttatgatg tccaaattat cttttttct tttctttttt    10080 agatcaaaat aggggtctat tttgattacc actgttattt tatctccatt tgattttcga    10140
```

```
tttttatttt tattttttcta atttcattgt aaattttaa ttaaacccaa atattctagg    10200
ggaaagaggc aagataaaaa tagtctaact tgggcataaa ttttagagtc atattctctt    10260
gccgagaaag gaaactagct ctcttacatt gattgtttaa tttcagacgt cactacttta    10320
tgaggatgcc caaattatgg gctttaaaaa atatatatcc aaacagggg tcagaaagaa    10380 taactaattt gtccacaaca acacaaaaaa tgattccacc ataagtttgc ccagtgacag    10440
ggtctatatt attttctata tatcaaattc tacaactggt tcttaaagct actgtacata    10500
acctaagtta aaatattagg tattagttga taagacattt tatcatctat gaaatgttgc    10560
ctgttgtcat agttagagaa tcttttaaaa tatggagcta ttttcataga ttaaactatg    10620
ccagttaaaa gttgggtaaa aagaactaca gaataatatt tatgtttatc gtgtaaggtt    10680
ttaaagcaaa ctccaagtca ttttcatcaa tgaaatcaat aaggttttgc aaatatatat    10740
gtatgaaaat actgatttaa aatgcaaata aggggagagt ttgagagaga gagagagacc    10800
aaatgatttt ataattctag taagtttata ggtttatggg gttttttacgt acttttctac    10860 ccaacttgtc tataagactt taatgaatca cttagaattt ttaaaataat ttattattac    10920
tctgtacctg ttctttactc tgcaaatctt accttgccct tttgtctaaa agcaataaaa    10980
tctgacctgg tttatatcgt atcattgatt ttgttactta gcaagcacag tgatccatta    11040
ggcctatgta ggctcatggt ttatacaaca ctgccatctg ctgacagagt gtgacagtca    11100
cagtcagcaa cacgagacca cttttatttt c attttagtg tttatagaaa tatgaatata    11160
cacaaatagt ataatgaacc ctaagcttca caaattaaca ttttgctaat cttgtttcaa    11220
ctaccgcctc cccctcatc caattactct gttctctcac ctcctcacac acagacactg    11280
gcagtatttt tcagccaatc attaatacgt tgccaactga taaggacttt taaaaaacaa    11340
ccaccattcc attatgattc ccagcataat tgagagtaat tccctaatat ccaatacccca    11400 ttttctattc caatttcctt gattgtcttt aaactgtttt taccctaagt ttgcttaaat    11460
caaagtccag gtcctgttaa acatatggtt aagttttacc caaacccaaa taaataaata    11520
aataaataaa taaataaacct attttttcca attccaggga atagtgaaag agggtaaatg    11580
ccattattta gaaacataaa tcacatcata ggactagaat tatcttgaag tcaaaattga    11640
agactgaaaa tggaaaagaa aggtatagac taaacttatt taaaaacttc aatgcagaac    11700
tctaagagaa gatattagaa agttgtacca gcattcatta ttcagtattc atcagtattc    11760
actcagctat atgtagttga aatctaacta gaggagcttg atcagataaa gagatacatt    11820
tttctcacca aggcggactc tggaggcagg tggttcagag ctagacagct gctgcaggac    11880
ccaggtcctt tccctgcctg ctcctccact ctagcttgtg actttcatcc tgcaagatgg    11940
gtgtttctgc caagttccag atagaagaag atagaacaca aaggagaaat aagcagtggt    12000
gcctctgtcc atcaagcaaa attttccag aaatgcacaa tagatttcag atgatgtctc    12060
aacagtccta actgcaaaga agctgaggaa ttagattttt ggctgggaca ctgttgccct    12120
gtaaaaaaat tgggattctg ttattaaaga ataagaggag ggaagaaaga ttgaaaactc    12180
ctatgcaata gtgaaaaaaa taagaaactc aataaaaaag tgggcatacc ttaaaaacag    12240
gcaattcaca acagatgaga ccccaatagc caataaacat ttttaaatgg tcaacctcat    12300
gagtgatcag aaaacacaaa tatgtatttt aaaccaaaaa taaaatacaa tgtattgacc    12360
atttgagtgg aaaaaaatta aaaagcctga taatatcaag tattggagag gatgtagagt    12420
gaggaaactc catggaggac ctatcattgc aaatgtggga atgaaactta atacacgaat    12480
```

```
ttgaggccaa tttgtaaatt gaaaaatgcg cacaccctgc aaccaagtac cccttgcaat    12540 attttttgaaa agacaaaaac gttatgtaaa tggaatcatg caatatgtga cctttatact    12600
cagcataatg cccctcagat ccattgaagt catgtgtatc aacagctcac tattttttt     12660 ttaattttt ttagagacag agtctcactc tgtcacacag ggtggagtgc agtggcgaga    12720
tcataactct ctctagcagc ctcgaactcc tgggctcaag catcctcctg cctcagcctc    12780
ccaagtagct aggactacag gcatgggaca caacacacag ctaatttttt taaatttttt    12840
ttagagacat ggtctcacta tgttgcctac gctggtctca aactcctagg tcaagcgatt    12900
ctcccacctc tacttcacaa agtgctgtag gtatgtaggt atggattgta ggtatgaacc    12960
accgtgccca actcactact ttttattact aattattcca tgggatggat gtaccgcagt    13020
ttgttttacc attaatctat tgtaggacat tttgactgat tccagttttt ttttaataca    13080
aataaaacca ctatgaatag ttgtgtattg tatacgtttt tgtgctaagt tttcattttt    13140
ctgggataag ttttcatttc tttgggcttt tactgtatcc ttgatattat aatatgttac    13200
atcttcagtt ttattctatt caatatataa tcttttattt tccttgaaat ctcccatgga    13260
ttgtttagaa gtgtgttgtt ttgtttccaa gggtttggca ttttttccat tattttttcta    13320 ttatcgattt ccagtttgat tccaggtggt cagagaacac acttcatgtg atttcagttc    13380
tattaaattt gttgaggttt gttacatggc ccagtatatg gcaattttgg tatatgttcc    13440
atgagcactt gaaaagaatg cgaattctgc tggtgctggt tggagttttc cagcaatgtt    13500
gatttatgat cttactcatt gatggtggtg ttgagtttga tgtgttctta cgatggcagc    13560
tttaacattc ttgtcaggta attctaacgt ctctgtcatg tcagtattag cgcctcttaa    13620
ctgtctcatc aaagctgaga ttttcctggt tcccctggtt cctgttggga tgtgtggttt    13680
tcatttgaaa tctggacttt ggagtattgt gttatgaggc tttggatctc atttaaactc    13740
atctcagcga atttcctctc ttgccactca ggaaggagaa gttgggtgtt tgaatggagc    13800
agagccgtta ctgcctaaga attgttttac tgggcttccc cttctcttct cctttgacta    13860
gagagagcca gcttttatt agggctttat gttttttctgg gcctgttggt gtttctgggt    13920
tgacaaactt ctccagaacc aagtctggaa tggatgaggc aaaaagaaac cccgtggaat    13980
gcactgctgg gtcgctcctt gggtcccaat gttcctaact ggtctgcctt cttctctcca    14040
gcttccagag tcttcataag tttgcttttac gtacaatgtc cggggttttt acttacttg    14100 agagaaatag gtaaaagtaa ttctactcca tctttcagga agcaaaagcc cccttgtgta    14160 ttttttttaaa ctttcaaaaa caaaacaaaa ggcagctgca acagtaaaga agctagtaac    14220
acccttggtg ggaaattcaa gtccaaatac acattttaag tttggctagc cagtgagaac    14280 atcagaaatag ttcaggtttt aaacaaattt atatttatga ttatgcatat actaaaagct    14340
gaaggcatct tatatttact aagcacctat tttgttcttg ttaaaaagac agaattccat    14400
tccctaggaa atttgacctg gcagctggag ctgatccacc tggccactag agcacagagc    14460
agggagagta gtagccctgc cccagccacc cctcaagaca ggattctttc tctgggaact    14520
gtaggtaaca ctaaatcgtt ctggaacaca acaacgaaag aagaaggaa agagaaagaa    14580 agaaaggaag aaagagagag agaaggaagg aaggagggga gggaaggaag gaagggaag    14640 ggaagggaat ggaagggaag gaaggaagga aaggaaggaa agggagggag agaggaagga    14700
aggaaggaaa ggaaaggaag gaaggaagaa ggaaagaaaa aagaaagaa aagaaaagaa    14760 aagaaagaca agaaagaaag aaagaaagaa agaaggggga aagaaaagaa agaggaaaga    14820
aagagaaaga agaaaaagaa agaaaggaaa gaaagagaaa gaaagaaaaa gaaagagaaa    14880
```

```
gaaagagaaa gacaagaaag aaaaaggaaa gaaaagaaag agaaagaaaa gaaagaaagg  14940
aaagaaagag aaagaaagaa aaagaaagaa agaaagaaag aaagagaaag aaagaaagaa  15000
aaagaaagaa agaaagaaag aaagaaaaag aaaagaaagg gagaaaatga cagcaattac  15060
ttttgcaaca acctaatata agttttttaa aagttaaata ttctgttcca tgcattgctg  15120
gataccttat aaataacagg gcatcctatg acctgaattt cccaaattat gagttgaggg  15180
tttgaactag ttttaaaaaa caaggaggcc aggcgcactg gctcatgcct gtaatcccag  15240
cactttggga ggctgaggca ggtggatcac gaggtcagga gctcgagacc agccttacca  15300
acatagtgaa acaccgcctc tactaaaaat acaaaaatta gccgggcgtg atggtgcgca  15360
cctgtaatct cagctactca gcaggctgag gcaggagaat cgcttgaacc cagaaggcgg  15420
aggttgcagt gagccaagat cacagcattg cactccagcc tgggcgacag agggagactc  15480
cgtcttcaaa aaaaaaaaaa aagacaagga atctgtaaaa caggcactgg aagtatatgc  15540
acttttattt tcattctatg ctatccgatg cctactgcta tttcccttca tatttaacct  15600
ccaacagctg cattttgctc cctccagacc acctgattgg agctcacgtg ctcccacaca  15660
gtacctccaa ccagagagag tcgagtccca cagaaaggcg taacaatcac cagtaatttt  15720
gcacttattt tacattgtgc cttgatacag agtactcaat gaatgctctt tgaatcatat  15780
ttaataaata tgtgtatttg ggattgtagc atattgcagc tacctggata tataaattaa  15840
ttagaaaaaa aattttgtgt ggctcaatca acaaacgact tttctctctc tctctttctc  15900
tttctccctc tctctctctt tcttctcagt tgatgttgct ggagttcagt gttgtgcaga  15960
tggcagtgac aaatgccatg ggcacatgag atatgataaa aggtccctga agaaggtgga  16020
gaaccagtta tcttatgaaa ttttccagag tgggtactgg atctctcctg tctggcacca  16080
tgctggcctc agcccaaggg gaatttcctt ccagagacag agggcagtga ttgaggtggg  16140
gagacagatc gtaacactga gacttacatg aggacaccaa acagaaaaaa ggtggcaagt  16200
atagaaaatt cttctttctg gacagtcttc tctgttctaa cttcagcaaa attctccccc  16260
cagtggatgc tattgcacaa ccctacatat gctatgtttt ttcctataca cacttaccta  16320
tgataaaatg cattaattag tcacagtaag aggttaacaa caataactag taataaaata  16380
gaacaattca gtaaaataag agttacttga gcacaaacac taggatatca tgacagtcaa  16440
tctgatgacc aagagggcta ctaagcatct aaacaggagg gtaagtgtag acagcatgga  16500
gacgctggac aaagggatga ttcagtccca ggctggtatg gagcggaagg gcatgatatg  16560
tcatcacgct actaaggcac acaatttaaa atgagtaaat tcttatttct agaaatttct  16620
ttttaatatt ttcagactac agttgcctac aggtaactga aaccccagaa agcaaaattg  16680
ttgataagga ggtactactg tacatcgtcc tttgaaccaa ctttatcatt tgctagtata  16740
tacatatata cctacataca tacatataca catcctgca cacacctata tgtatacgta  16800
cacacacaca cacgcacaca cacacactca catctactaa tgttagaata agtttgctaa  16860
ataagatgca caacttgtta atgtcctaca gagcaataaa accataagca ttggggttat  16920
cttttctact agataaaaat ccattatcat tttcataaag ttttctttac attaacatct  16980
aacttttgca atctagtttt taatcatcat aaataggaag caaatgaact gtttctctag  17040
tgaatcaaat atccttgaaa acatacatag tcatcttttt ggtttatttt tattttttaga  17100 taaattattt aaagttttaa ataatttaac attcacaata gtttgtgact gtatattttg  17160
acttggtcct tcaaacttaa tttgtacttt tatgtatcgt gcttacctca attttttatt  17220
```

```
cactttttcct aaactttgct ggattggttt attattttttg tctatttctt ttccttctag    17280
tggtttggga gggttttttta aatcccatta ctattgaatg cctattaact tgcccccttt     17340
ttctttcaat ctctattccc acggcctgaa gcatgagggc caagctgtct gtaaccagca     17400
gagagatgac ccaggtgtta ttccactctc cactgtccac ctatcaccat tcccagcccg     17460
atagctctga agtacggctt ttctggggct ctgtggggaa aactagaact ggctgcttca     17520
aggacacctc ctgttttttgc aatggaaaaa atgtttctaa attccagttt ctctatgaat    17580
tcaatgacat ggtttaaatc tctgtggtgt tcttcaaagt tttttcttct aataggacct     17640
ctcatgattc tccaaccacg aaataaattc attatcattt ttatatttct tctgtcattg     17700
caaaggaggt tttgaaagag tggaggacgc gctaatgaac tcaaaaatcc acactattcc     17760
ttgtttccat ctgttgttca ttcattgttt ccattggcct gtccgcctcc tatcctcctt     17820
cttagacttg gagctctagc ctcagccagg atagggaaaa gagagatcag actgttactt     17880
tgtctatgta gaaaaggaag acataagaaa ctccatttttg atctgtatcc tgaacaattg    17940
ttttgccttg agatgctgtt aatctgtaac tttagcccca accttgtgct cacagaaaca     18000
tgtgttgtat ggaatcaaga tttaagggat ctagggctgt gcagaatgtg ccttgttaac     18060
aacatgttta caggcagtat gcttggtaaa agtcatcgcc attctccatt ctcgattaac     18120
taggggcaca gtgcactgcg gaaagccgca gggacctctg cccaggaaaa ctgggtattg     18180
tccaaggttt ctccccactg agacagcctg agatatggcc ttgcgggatg ggaaagatct     18240
gaccgtcccc cagcctgaca cccgtgaagg gtctgcgctg aggaggatta gtaaaagagg     18300
aaggcctctt gcggttgaga taagaggaag ccctctgtct cctgcatgcc cctgggaacg     18360
gcatgtctca gtgtaaaacc tgattgtaca ttcgttctat tctgagatag gagaaaaccg     18420
ctctgtggct ggaggcgaga tatgctggcg gcaatgctgc tctgttgttc tttactacac     18480
tgagatgttt gggtgagaga agcataaatc tggcctacgt gcacatccag gcatagtacc     18540
ttcccttgaa tttacttgtg acacagattc ctttgctcac atgttttctt gctgaccttc     18600
tccccactat caccctgttc tcctgccgca ttcccttgc tgaggtagtg aaaatagtaa      18660
tcaataaata ctgagggaac tcagagaccg gtgccagcgc gggtcctccg tatgctgagt     18720
gacggtccct tgggcccact gttccttctc tatactttgt ctctgtgtct tatttcttt     18780 ctcagtctct cgtcccacct gacgagaaat acccacaggt gtggaggggc tggacacccc     18840
ttcgagccag gattatcagg gcatttgggg gtctgcaaaa ctaagcccca actcatcgat     18900
ttcacaactt catccagagc cagcctgaac agtagttgcc catgattct atgccttaat      18960 acgagaagag aacatagggg ctgggtgcca agtaggtaga cagggagggc agggaactct     19020
aagacagagc ttgagggget cattcctctt gcaaaatgaa acaaaaacca cagcactgaa    19080
tatgtaaatc tcggtggctg aacccctcct aggatagtaa gccctgacac aattgctgct    19140
atcttctctt tctctcaagg aagtcaaaaa acacctgcag ccttactgtc cccttggaaa    19200
caagatgaac atctacattt tctaaagtgg acaagaatc tctgttcata tttatgtccc     19260
atgcatttgc acgtggccgg acaaaggact tgcttctgc cagcacatct gtcttcagat     19320
atgagaggaa acagacacaa cctggaggcg gcaaagaagc agctcttttct caagtgacct   19380 cctctatctc cctacttcct ggctaatggg gcagccttga tccttgggaa tccaggacag     19440
atatccactc gtgacaaact agctggaaga atgacaacca atcaggttcc aagcaccact    19500
ggatgtgaac cacagaattt cctcctctcc ttgtggaatg tcagcttacg tctgacaaaa    19560
aatgtaaaac tgagagagtt acaatcttaa ggaggagtca agctaaagca gaaagaatca    19620
```

```
cctactctgg actccagcat gactgctgag ctcaaatata tatagagaga gaaagaacca   19680
caaacttgaa gatggatatc agctacagac tttcctgagt caggtaggga aatggccatc   19740
cctcaaacct tgcaaaaggc aaacttatgc cattgtgtcc tctgacatac tgggtgatgt   19800
actgtatgtt actgatgtga ggggaacttc ctaaattggc tagtaaatta tgccaaataa   19860
aaagcaaaaa tgatatttct tgaaatgtta catctgagga acattgctaa ataatttat   19920 cagtagtttt caggatgatt tatagatgtg cattgaagtg tgtacttgtg ctctctctct   19980
cctctctctc tctcttttctc tcctctctct cgctctttct ctccttgccc cctccctcc   20040 ctgactttcc ttcctgtccc ctccacagca gtttatattt tttttctgat aatctaactt   20100
tgctgagggt tcaatgtaaa gcaccttcag tgatgagtta gttggaatgt tccccaagaa   20160
attctatttc cagcactctt ttacatgaaa tccaagaagc tctcagacta tcttactgac   20220
accttgcctt tcctcaacag atcaatctta tcaatgtcca tcacagatat tttgtagaac   20280
ggtggatcct ggcagagtct cacagatgct tctgagacaa catttgcttt caaaaaatga   20340
accacacaca tcctaaagat ctcagccact tcccatgttt cattttgtgt tacagcaaac   20400
atcacaacaa tcattcctac agatcaccac tgcatgtgat caataaaata gttttttgcaa   20460 caatggtact tatgataatc atcttttatt gtttacaaat actgctttac aatagttatt   20520
cggttgcact gttcatatta gatttccaat tagctcactt aggaacataa gtccctcgaa   20580
cagctcagtc atcttttttca ttcctgtttc tatccctac atctcttttcc tttgcagacg   20640 actatctcct acactgaaac aggaaagctt ttaccttttt ggcatgcttg atttaaagat   20700
tatagaaaag tatttgacaa agaaaactca cacatgtgtg tacatatctt ttaaaaagtt   20760
atgtttatgc attgcacagg aatatcgaga atgctaatag gcaatgtcag agtttactgt   20820
ttttcaaaat tagtacagtt ttattatttc taaaaactat aaaatgaata tattcacatc   20880
accatacaga agagtaggag gagatggcat aaagtgtcat tgttcctcct ctgcaatccc   20940
aggagataac taccaagcac aatttatgtc ttttaaaatt cagcccgtat ttatatacat   21000
atatattcaa tgtagatggg atcatgatat ctcaccacac atactcttca gtgacctgca   21060
ttttcacaaa caccttccac gtaactatat agaagtctac gtcttcccct taatgtctgc   21120
tttgtgctac attgtaaagc tctagcacag tttaaccaaa ctcctattaa tgaggatttt   21180
agttattttt cactctttaa acaatatttc catgtgtagt cttatacata cgtctgtaca   21240
cacttatccc agtctaagga gttccttta ccttcccccca tcccagcatt ccctgtcacg   21300
cttgttgctt ccgttgagtg actttactcc tggagtataa tctgcgtata gttcagttaa   21360
aaacatggga tctgagttta ggtcacagct ctgccactta ctgccataag ccagttcctt   21420
gacctctctg ccctcaagtt tttgcaccta caaagtaggg gataatatta gttcctagtt   21480
catagagtct tgggaataat taaatgtgat gatccatgta caatgtctgg cacttagtaa   21540
gtgctcaata aatgtcaccc tttatgattg gtattgcgtg tatgtctgca gagaaaatca   21600
ctttgtgtcc cctttaaaaa aggactatgc ccttggtcag ctattttgca cattaaattt   21660
cacttgccaa tattaactct ccacctctaa cttgatccct ctccttcctc atcttctggt   21720
gagaccaaat gctaattctg ctattcaagg caactagcaa agctgccagt gacagaatca   21780
aataaaccta cccctaatct ttagaattgt agttatgatt tctgttgtaa aagttactgt   21840
tgtggcagtc agtattagtc tttggtctat gatagcatct ctgatctatt attgaytttc   21900
aattakgtat ttttttttat ttattctgaa aatgtttgtt aagcatttgc taagtaaaga   21960
```

```
tactggackg agcctcccaa atacagggca aataaaacat caaacagctt ataatttaga    22020
agggtagaag agaatctgaa agcaggtaaa aataaacagg cactcggctg ggcgcgtgg    22080 ctcacgcctg taatcccagc actttgggag gccgaggtgg gcggatcacg aggtcaggag    22140
atcgagacca tcctggctaa cacggtgaaa ccccgtctct actaaaaata caaaaaatta    22200
gcgaggcgtg gtggcgggcg cctttagtcc cagctagtcg ggaggctgag gcaggagaat    22260
ggtgtgaacc cgggaggcgg agcttgcagt gagccaagat cgcaccactg cactccagcc    22320
tgggygacag agcgagactc cgtctcaaaa aaataaata aataaataa aaataatta    22380 ggtactctag gcccagtgac ctgtctctgt actctgtaaa ttcaggtcac ctgctcaggg    22440
ctaatctgag agaaggtctc tcttcagttg aattttgaaa gacaattagc agttcacaag    22500
ctaacccagg tggacaaaga tgttcccaag cagagggagt gcttgtgaaa gctggaggcc    22560
atagaaaaac tctaaggagt gtagggaggt gggagtaatg tatggaaggg gtggagatgg    22620
aaggttaaga gagatacaag gctgcaaaaa tggagctgga ctcaaaagaa aatactgaaa    22680
aggtcttcag tgttgttgat gagattacta tggaaacact atggaacact gggactccat    22740
ggcagctcca aagatggcat gcgcctggtc cagctcagta agagctgagc tcttcctgtg    22800

<210> SEQ ID NO 101
<211> LENGTH: 154
<212> TYPE: DNA
<213> ORGANISM: Artificial Sequence
<220> FEATURE:
<223> OTHER INFORMATION: synthetic

<400> SEQUENCE: 101
tctggcaaca cggcctccct gaccgtctct gggctccagg ctgaggatga ggctgattat     60
tactgcagct catatgcagg cagcaacaat ttaagtcttc ggaactggga ccaaggtcac    120
cgtcctaggt cagcccaagt ccactcccac tctc                                154

<210> SEQ ID NO 102
<211> LENGTH: 156
<212> TYPE: DNA
<213> ORGANISM: Artificial Sequence
<220> FEATURE:
<223> OTHER INFORMATION: synthetic

<400> SEQUENCE: 102
tcagggacaa tggccacctt gactatcagt ggggcccagg tggaggatga agctgactac     60
tactgttact caacagacag cagtggtaat cattatgtct cggaactgg gaccaaggtc    120 accgtcctag gtcagcccaa gtccactccc actctc                              156

<210> SEQ ID NO 103
<211> LENGTH: 150
<212> TYPE: DNA
<213> ORGANISM: Artificial Sequence
<220> FEATURE:
<223> OTHER INFORMATION: synthetic

<400> SEQUENCE: 103
tctgggaaca cagccactct gaccatcagc gggacccagg ctatggatga ggctgactat     60
tactgtcagg cgtgggacag cagcactgcc gtcttcggaa ctgggaccaa ggtcaccgtc    120
ctaggtcagc ccaagtccac tcccactctc                                     150

<210> SEQ ID NO 104
<211> LENGTH: 21
```

```
<212> TYPE: DNA
<213> ORGANISM: Artificial Sequence
<220> FEATURE:
<223> OTHER INFORMATION: synthetic

<400> SEQUENCE: 104
aggtggaaac acggtgagag t                                            21

<210> SEQ ID NO 105
<211> LENGTH: 21
<212> TYPE: DNA
<213> ORGANISM: Artificial Sequence
<220> FEATURE:
<223> OTHER INFORMATION: synthetic

<400> SEQUENCE: 105
ccactcgggg aaaagttgga a                                            21
```

HUMAN LAMBDA LIGHT CHAIN MICE

CROSS-REFERENCE TO RELATED APPLICATIONS

This application is a continuation of U.S. patent application Ser. No. 14/638,429, filed Mar. 4, 2015, which is a continuation of U.S. patent application Ser. No. 13/945,582, filed Jul. 18, 2013, which is a divisional of U.S. patent application Ser. No. 13/166,171, filed 22 Jun. 2011, which claims the benefit under 35 USC §119(e) of U.S. Provisional Application Ser. No. 61/357,317, filed 22 Jun. 2010 and U.S. Provisional Application Ser. No. 61/357,314, filed 22 Jun. 2010, each of which are hereby incorporated by reference in their entirety.

FIELD

Genetically modified mice that comprise a mouse or human lambda variable (Vλ) light chain sequence operably linked with a mouse or human light chain constant region (λ or kappa (κ)). Genetically modified mice that express epitope-binding proteins that comprise an immunoglobulin light chain comprising a variable domain derived from a human lambda variable (hVλ) gene segment, a human lambda J (hJλ) gene segment, and a mouse light chain constant ($C_L$) domain. Genetically modified mice, comprising an unrearranged immunoglobulin lambda (λ) light chain variable nucleic acid sequence at an endogenous mouse light chain locus. Mice capable of rearranging and expressing a chimeric human λ/mouse $C_L$ light chain from an endogenous light chain locus that comprises a replacement of all endogenous mouse light chain variable region gene segments with one or more hVλ gene segments and one or more hJλ gene segments. Somatically mutated antibodies comprising hVλ domains and mouse $C_L$ domains.

BACKGROUND

Mice that express antibodies that are fully human, or partly human and partly mouse, are known in the art. For example, transgenic mice that express fully human antibodies from transgenes containing human light and heavy chain immunoglobulin variable region genes have been reported. Genetically modified mice that comprise a replacement of the endogenous mouse heavy chain variable region (HCVR) gene segments and kappa (κ) light chain variable region (LCVR) gene segments with human HCVR and LCVR gene segments and that make chimeric antibodies with a chimeric human/mouse kappa chain are known as well.

Antibody light chains are encoded by one of two separate loci: kappa (κ) and lambda (λ). Mouse antibody light chains are primarily of the κ type. The ratio of κ to λ light chain usage in humans is about 60:40, whereas in mice it is about 95:5. Biased usage of κ light chains in mice is reportedly sustained in genetically modified mice capable of expressing fully or partly human antibodies. Thus, mice that express fully or partly human antibodies appear to be constrained in lambda variable usage.

There is a need in the art to generate lambda variable regions, whether mouse or human, for use in making epitope-binding proteins. There is a need in the art for mice that express fully or partly human antibodies, wherein the mice display an increased lambda variable (Vλ) usage.

There is a need in the art for mice that express fully or partly human antibodies, wherein the mice display an increased λ variable (Vλ) usage.

SUMMARY

Genetically modified mice, embryos, cells, tissues, as well as nucleic acid constructs for modifying mice, and methods and compositions for making and using them, are provided. Mice and cells that generate lambda (λ) variable regions (human or non-human) in the context of a kappa (κ) light chain are provided. Mice and cells that generate human λ variable regions in the context of a κ or a λ light chain, e.g., from an endogenous mouse light chain locus, are also provided. Also provided are methods for making antibodies that comprise lambda variable regions. Methods for selecting heavy chains that express with cognate lambda variable regions are also provided.

Chimeric and human antigen-binding proteins (e.g., antibodies), and nucleic acids encoding them, are provided that comprise somatically mutated variable regions, including antibodies that have light chains comprising a variable domain derived from a human Vλ and a human Jλ gene segment fused to a mouse light chain constant domain.

In one aspect, a mouse is provided that expresses a human λ variable region sequence on a light chain that comprises a mouse constant region. In one aspect, a mouse is provided that expresses a human λ variable region sequence on a light chain that comprises a κ constant region. In one aspect, a mouse is provided that expresses from an endogenous mouse light chain locus a light chain that comprises a human λ variable region sequence. In one aspect, a mouse is provided that comprises a rearranged light chain gene that comprises a human λ variable sequence linked to a mouse constant region sequence; in one embodiment, the mouse constant region sequence is a λ constant sequence; in one embodiment, the mouse constant region sequence is a κ constant sequence.

In one aspect, a genetically modified mouse is provided, wherein the mouse comprises an unrearranged human ⌊ light chain variable gene segment (hVλ) and a human λ joining gene segment (hJλ). In one embodiment, the unrearranged hVλ and hJλ are at a mouse light chain locus. In one embodiment, the unrearranged hVλ and unrearranged hJλ are on a transgene and operably linked to a human or mouse constant region sequence. In one embodiment, the unrearranged hVλ and unrearranged hJλ are on an episome. In one embodiment, the mouse is capable of making an immunoglobulin that comprises a light chain that is derived from an unrearranged hVλ sequence and a hJλ sequence and a mouse light chain constant region ($C_L$) nucleic acid sequence. Methods and compositions for making and using genetically modified mice are also provided. Antibodies are provided that comprise (a) a human heavy chain variable domain ($hV_H$) fused to a mouse heavy chain constant region, and (b) a human Vλ fused to a mouse $C_L$ domain; including wherein one or more of the variable domains are somatically mutated, e.g., during antibody or immune cell selection in a mouse of the invention. In one embodiment, the unrearranged hVλ and unrearranged hJλ are operably linked with a human or mouse κ constant region (Cκ). In one embodiment, the unrearranged hVλ and unrearranged hJλ are operably linked with a human or mouse λ constant region (Cλ).

In one aspect, a mouse is provided that comprises in its germline, at an endogenous mouse light chain locus, a human λ light chain variable region sequence, wherein the human lambda variable region sequence is expressed in a light chain that comprises a mouse immunoglobulin constant region gene sequence.

In one embodiment, the endogenous mouse light chain locus is a λ locus. In one embodiment, the endogenous mouse light chain locus is a κ locus.

In one embodiment, the mouse lacks an endogenous light chain variable sequence at the endogenous mouse light chain locus.

In one embodiment, all or substantially all endogenous mouse light chain variable region gene segments are replaced with one or more human λ variable region gene segments.

In one embodiment, the human λ light chain variable region sequence comprises a human Jλ sequence. In one embodiment, the human Jλ sequence is selected from the group consisting of Jλ1, Jλ2, Jλ3, Jλ7, and a combination thereof.

In one embodiment, the human λ light chain variable region sequence comprises a fragment of cluster A of the human light chain locus. In a specific embodiment, the fragment of cluster A of the human λ light chain locus extends from hVλ3-27 through hVλ3-1.

In one embodiment, the human λ light chain variable region sequence comprises a fragment of cluster B of the human light chain locus. In a specific embodiment, the fragment of cluster B of the human λ light chain locus extends from hVλ5-52 through hVλ1-40.

In one embodiment, the human λ light chain variable region sequence comprises a genomic fragment of cluster A and a genomic fragment of cluster B. In a one embodiment, the human λ light chain variable region sequence comprises at least one gene segment of cluster A and at least one gene segment of cluster B.

In one embodiment, more than 10% of the light chain nave repertoire of the mouse is derived from at least two hVλ gene segments selected from 2-8, 2-23, 1-40, 5-45, and 9-49. In one embodiment, more than 20% of the light chain nave repertoire of the mouse is derived from at least three hVλ gene segments selected from 2-8, 2-23, 1-40, 5-45, and 9-49. In one embodiment, more than 30% of the light chain nave repertoire of the mouse is derived from at least four hVλ gene segments selected from 2-8, 2-23, 1-40, 5-45, and 9-49.

In one aspect, a mouse is provided that expresses an immunoglobulin light chain that comprises a human λ variable sequence fused with a mouse constant region, wherein the mouse exhibits a κ usage to λ usage ratio of about 1:1.

In one embodiment, the immunoglobulin light chain is expressed from an endogenous mouse light chain locus.

In one aspect, a mouse is provided that comprises a λ light chain variable region sequence (Vλ) and at least one J sequence (J), contiguous with a mouse κ light chain constant region sequence.

In one embodiment, the mouse lacks a functional mouse Vκ and/or mouse Jκ gene segment.

In one embodiment, the Vλ is a human Vλ (hVλ), and the J is a human Jλ (hJλ). In one embodiment, the hVλ and the hJλ are unrearranged gene segments.

In one embodiment, the mouse comprises a plurality of unrearranged hVλ gene segments and at least one hJλ gene segment. In a specific embodiment, the plurality of unrearranged hVλ gene segments are at least 12 gene segments, at least 28 gene segments, or at least 40 gene segments.

In one embodiment, the at least one hJλ gene segment is selected from the group consisting of Jλ1, Jλ2, Jλ3, Jλ7, and a combination thereof.

In one embodiment, an endogenous mouse λ light chain locus is deleted in whole or in part.

In one embodiment, the mouse κ light chain constant region sequence is at an endogenous mouse κ light chain locus.

In one embodiment, about 10% to about 45% of the B cells of the mouse express an antibody that comprises a light chain comprising a human λ light chain variable (Vλ) domain and a mouse κ light chain constant (Cκ) domain.

In one embodiment, the human λ variable domain is derived from a rearranged hVλ/hJλ sequence selected from the group consisting of 3-1/1, 3-1/7, 4-3/1, 4-3/7, 2-8/1, 3-9/1, 3-10/1, 3-10/3, 3-10/7, 2-14/1, 3-19/1, 2-23/1, 3-25/1, 1-40/1, 1-40/2, 1-40/3, 1-40/7, 7-43/1, 7-43/3, 1-44/1, 1-44/7, 5-45/1, 5-45/2, 5-45/7, 7-46/1, 7-46/2, 7-46/7, 9-49/1, 9-49/2, 9-49/7 and 1-51/1.

In one embodiment, the mouse further comprises a human Vκ-Jκ intergenic region from a human κ light chain locus, wherein the human Vκ-Jκ intergenic region is contiguous with the Vλ sequence and the J sequence. In a specific embodiment, the human Vκ-Jκ intergenic region is placed between the Vλ sequence and the J sequence.

In one aspect, a mouse is provided that comprises (a) at least 12 to at least 40 unrearranged human λ light chain variable region gene segments and at least one human Jλ gene segment at an endogenous mouse light chain locus; (b) a human Vκ-Jκ intergenic sequence located between the at least 12 to at least 40 human light chain variable region gene segments and the at least one human Jλ sequence; wherein the mouse express an antibody that comprises a light chain comprising a human Vλ domain and a mouse Cκ domain.

In one aspect, a mouse is provided that expresses an antibody comprising a light chain that comprises a λ variable sequence and a κ constant sequence.

In one embodiment, the mouse exhibits a κ usage to λ usage ratio of about 1:1.

In one embodiment, a population of immature B cells obtained from bone marrow of the mouse exhibits a κ usage to λ usage ratio of about 1:1.

In one aspect, a genetically modified mouse is provided, wherein the mouse comprises an unrearranged immunoglobulin Vλ and a Jλ gene segment operably linked to a mouse light chain locus that comprises a mouse $C_L$ gene.

In one embodiment, the Vλ and/or Jλ gene segments are human gene segments. In one embodiment, the Vλ and/or Jλ gene segments are mouse gene segments, and the $C_L$ is a mouse Cκ.

In one embodiment, the endogenous mouse light chain locus is a κ light chain locus. In one embodiment, the endogenous mouse light chain locus is a λ light chain locus.

In one embodiment, the unrearranged Vλ and Jλ gene segments are at an endogenous mouse light chain locus.

In one embodiment, the unrearranged immunoglobulin Vλ and Jλ gene segments are on a transgene.

In one embodiment, the mouse further comprises a replacement of one or more heavy chain V, D, and/or J gene segments with one or more human V, D, and/or J gene segments at an endogenous mouse heavy chain immunoglobulin locus.

In one embodiment, the mouse comprises an unrearranged immunoglobulin Vλ and a Jλ gene segment at an endogenous mouse κ light chain locus that comprises a mouse Cκ gene.

In one embodiment, the mouse comprises an unrearranged human immunoglobulin λ light chain variable gene segment (Vλ) and a λ joining gene segment (Jλ) at an endogenous mouse λ light chain locus that comprises a mouse Cλ gene.

In one embodiment, the light chain variable gene locus (the "$V_L$ locus") comprises at least one human Vλ (hVλ) gene segment. In one embodiment, the $V_L$ locus comprises at least one human Jλ (hJλ) gene segment. In another embodiment, $V_L$ locus comprises up to four hJλ gene segments. In one embodiment, the $V_L$ locus comprises a contiguous sequence comprising human λ and human κ genomic sequence.

In one embodiment, the κ light chain variable gene locus (the "κ locus") comprises at least one human Vλ (hVλ) gene segment. In one embodiment, the κ locus comprises at least one human Jλ (hJλ) gene segment. In one embodiment, the κ locus comprises up to four hJλ gene segments. In one embodiment, the κ locus comprises at least one hVλ and at least one hJλ, and lacks or substantially lacks a functional Vκ region gene segment and lacks or substantially lacks a functional Jκ region gene segment. In one embodiment, the mouse comprises no functional Vκ region gene segment. In one embodiment, the mouse comprises no functional Jκ region gene segment.

In one embodiment, the λ light chain variable gene locus (the "λ locus") comprises at least one hVλ gene segment. In one embodiment, the λ locus comprises at least one human Jλ (hJλ) gene segment. In another embodiment, the λ locus comprises up to four hJλ gene segments.

In one embodiment, the $V_L$ locus comprises a plurality of hVλs. In one embodiment, the plurality of hVλs are selected so as to result in expression of a λ light chain variable region repertoire that reflects about 10%, about 20%, about 30%, about 40%, about 50%, about 60%, about 70%, about 80%, or about 90% or more of the Vλ usage observed in a human. In one embodiment, the $V_L$ locus comprises gene segments hVλ1-40, 1-44, 2-8, 2-14, 3-21, and a combination thereof.

In one embodiment, the hVλs include 3-1, 4-3, 2-8, 3-9, 3-10, 2-11, and 3-12. In a specific embodiment, the $V_L$ locus comprises a contiguous sequence of the human λ light chain locus that spans from Vλ3-12 to Vλ3-1. In one embodiment, the $V_L$ locus comprises at least 2, 3, 4, 5, 6, 7, 8, 9, 10, 11 or 12 hVλs. In a specific embodiment, the hVλs include 3-1, 4-3, 2-8, 3-9, 3-10, 2-11, and 3-12. In a specific embodiment, the $V_L$ locus comprises a contiguous sequence of the human λ locus that spans from Vλ3-12 to Vλ3-1. In one embodiment, the $V_L$ locus is at the endogenous κ locus. In a specific embodiment, the $V_L$ locus is at the endogenous κ locus and the endogenous λ light chain locus is deleted in part or completely. In one embodiment, the $V_L$ locus is at the endogenous λ locus. In a specific embodiment, the $V_L$ locus is at the endogenous λ locus and the endogenous κ locus is deleted in part or completely.

In one embodiment, the $V_L$ locus comprises 13 to 28 or more hVλs. In a specific embodiment, the hVλs include 2-14, 3-16, 2-18, 3-19, 3-21, 3-22, 2-23, 3-25, and 3-27. In a specific embodiment, the κ locus comprises a contiguous sequence of the human λ locus that spans from Vλ3-27 to Vλ3-1. In one embodiment, the $V_L$ locus is at the endogenous κ locus. In a specific embodiment, the $V_L$ locus is at the endogenous κ locus and the endogenous λ light chain locus is deleted in part or completely. In another embodiment, the $V_L$ locus is at the endogenous λ locus. In a specific embodiment, the $V_L$ locus is at the endogenous λ locus and the endogenous κ locus is deleted in part or completely.

In one embodiment, the $V_L$ locus comprises 29 to 40 hVλs. In a specific embodiment, the κ locus comprises a contiguous sequence of the human λ locus that spans from Vλ3-29 to Vλ3-1, and a contiguous sequence of the human λ locus that spans from Vλ5-52 to Vλ1-40. In a specific embodiment, all or substantially all sequence between hVλ1-40 and hVλ3-29 in the genetically modified mouse consists essentially of a human λ sequence of approximately 959 bp found in nature (e.g., in the human population) downstream of the hVλ1-40 gene segment (downstream of the 3' untranslated portion), a restriction enzyme site (e.g., PI-SceI), followed by a human λ sequence of approximately 3,431 bp upstream of the hVλ3-29 gene segment found in nature. In one embodiment, the $V_L$ locus is at the endogenous mouse κ locus. In a specific embodiment, the $V_L$ locus is at the endogenous mouse κ locus and the endogenous mouse λ light chain locus is deleted in part or completely. In another embodiment, the $V_L$ locus is at the endogenous mouse λ locus. In a specific embodiment, the $V_L$ locus is at the endogenous mouse λ locus and the endogenous mouse κ locus is deleted in part or completely.

In one embodiment, the $V_L$ locus comprises at least one hJλ. In one embodiment, the $V_L$ locus comprises a plurality of hJλs. In one embodiment, the $V_L$ locus comprises at least 2, 3, 4, 5, 6, or 7 hJλ. In a specific embodiment, the $V_L$ locus comprises four hJλ. In a specific embodiment, the four hJλs are hJλ1, hJλ2, hJλ3, and hJλ7. In one embodiment, the $V_L$ locus is a κ locus. In a specific embodiment, the $V_L$ locus is at the endogenous κ locus and the endogenous λ light chain locus is deleted in part or completely. In one embodiment, the $V_L$ locus comprises one hJλ. In a specific embodiment, the one hJλ is hJλ1. In one embodiment, the $V_L$ locus is at the endogenous κ locus. In a specific embodiment, the $V_L$ locus is at the endogenous κ locus and the endogenous λ light chain locus is deleted in part or completely. In another embodiment, the $V_L$ locus is at the endogenous λ locus. In a specific embodiment, the $V_L$ locus is at the endogenous λ locus and the endogenous κ locus is deleted in part or completely.

In one embodiment, the $V_L$ locus comprises at least one hVλ, at least one hJλ, and a mouse Cl gene. In one embodiment, the $V_L$ locus comprises at least one hVλ, at least one hJλ, and a mouse Cλ gene. In a specific embodiment, the mouse Cλ gene is Cλ2. In a specific embodiment, the mouse Cλ gene is at least 60%, at least 70%, at least 80%, at least 90%, at least 95%, 96%, 97%, 98%, or at least 99% identical to mouse Cλ2.

In one embodiment, the mouse comprises a replacement at the endogenous mouse κ locus of endogenous mouse Vκ gene segments with one or more hVλ gene segments, wherein the hVλ gene segments are operably linked to an endogenous mouse Cκ region gene, such that the mouse rearranges the human Vλ gene segments and expresses a reverse chimeric immunoglobulin light chain that comprises a human Vλ domain and a mouse Cκ. In one embodiment, 90-100% of unrearranged mouse Vκ gene segments are replaced with at least one unrearranged hVλ gene segment. In a specific embodiment, all or substantially all of the endogenous mouse Vκ gene segments are replaced with at least one unrearranged hVλ gene segment. In one embodiment, the replacement is with at least 12, at least 28, or at least 40 unrearranged hVλ gene segments. In one embodiment, the replacement is with at least 7 functional unrearranged hVλ gene segments, at least 16 functional unrearranged hVλ gene segments, or at least 27 functional unrearranged hVλ gene segments. In one embodiment, the mouse comprises a replacement of all mouse Jκ gene segments with at least one unrearranged hJλ gene segment. In one embodiment, the at least one unrearranged hJλ gene segment is selected from Jλ1, Jλ2, Jλ3, Jλ 4, Jλ 5, Jλ 6, Jλ7, and a combination thereof. In a specific embodiment, the one or more hVλ gene segment is selected from a 3-1, 4-3, 2-8, 3-9, 3-10, 2-11, 3-12, 2-14, 3-16, 2-18, 3-19, 3-21, 3-22, 2-23, 3-25, 3-27, 1-40, 7-43, 1-44, 5-45, 7-46, 1-47, 5-48, 9-49, 1-50, 1-51, a 5-52 hVλ gene segment, and a combination thereof. In a specific embodiment, the at least one unrearranged hJλ gene segment is selected from Jλ1, Jλ2, Jλ3, Jλ7, and a combination thereof.

In one embodiment, the mouse comprises a replacement of endogenous mouse Vλ gene segments at the endogenous mouse λ locus with one or more human Vλ gene segments at the endogenous mouse λ locus, wherein the hVλ gene segments are operably linked to a mouse Cλ region gene, such that the mouse rearranges the hVλ gene segments and expresses a reverse chimeric immunoglobulin light chain that comprises a hVλ domain and a mouse Cλ. In a specific embodiment, the mouse Cλ gene is Cλ2. In a specific embodiment, the mouse Cλ gene is at least 60%, at least 70%, at least 80%, at least 90%, at least 95%, or at least 98% identical to mouse Cλ2. In one embodiment, 90-100% of unrearranged mouse Vλ gene segments are replaced with at least one unrearranged hVλ gene segment. In a specific embodiment, all or substantially all of the endogenous mouse Vλ gene segments are replaced with at least one unrearranged hVλ gene segment. In one embodiment, the replacement is with at least 12, at least 28, or at least 40 unrearranged hVλ gene segments. In one embodiment, the replacement is with at least 7 functional unrearranged hVλ gene segments, at least 16 functional unrearranged hVλ gene segments, or at least 27 functional unrearranged hVλ gene segments. In one embodiment, the mouse comprises a replacement of all mouse Jλ gene segments with at least one unrearranged hJλ gene segment. In one embodiment, the at least one unrearranged hJλ gene segment is selected from Jλ1, Jλ2, Jλ3, Jλ 4, Jλ 5, Jλ 6, Jλ7, and a combination thereof. In a specific embodiment, the one or more hVλ gene segment is selected from a 3-1, 4-3, 2-8, 3-9, 3-10, 2-11, 3-12, 2-14, 3-16, 2-18, 3-19, 3-21, 3-22, 2-23, 3-25, 3-27, 1-40, 7-43, 1-44, 5-45, 7-46, 1-47, 5-48, 9-49, 1-50, 1-51, a 5-52 hVλ gene segment, and a combination thereof. In a specific embodiment, the at least one unrearranged hJλ gene segment is selected from Jλ1, Jλ2, Jλ3, Jλ7, and a combination thereof.

In one aspect, a genetically modified mouse is provided that comprises a human Vκ-Jκ intergenic region sequence located at an endogenous mouse κ light chain locus.

In one embodiment, the human Vκ-Jκ intergenic region sequence is at an endogenous κ light chain locus of a mouse that comprises a hVλ and hJλ gene segment, and the human Vκ-Jκ intergenic region sequence is disposed between the hVλ and hJλ gene segments. In a specific embodiment, the hVλ and hJλ gene segments are capable of recombining to form a functional human λ light chain variable domain in the mouse.

In one embodiment, a mouse is provided that comprises a plurality of hVλ's and one or more hJλ's, and the human Vκ-Jκ intergenic region sequence is disposed, with respect to transcription, downstream of the proximal or 3' most hVλ sequence and upstream or 5' of the first hJλ sequence.

In one embodiment, the human Vκ-Jκ intergenic region is a region located about 130 bp downstream or 3' of a human Vκ4-1 gene segment, about 130 bp downstream of the 3' untranslated region of the human Vκ4-1 gene segment, and spans to about 600 bp upstream or 5' of a human Jκ1 gene segment. In a specific embodiment, the human Vκ-Jκ intergenic region is about 22.8 kb in size. In one embodiment, the Vκ-Jκ intergenic region is about 90% or more, 91% or more, 92% or more, 93% or more, 94% or more, or about 95% or more identical with a human Vκ-Jκ intergenic region extending from the end of the 3' untranslated region of a human Vκ4-1 gene segment to about 600 bp upstream of a human Jκ1 gene segment. In one embodiment, the Vκ-Jκ intergenic region comprises SEQ ID NO:100. In a specific embodiment, the Vκ-Jκ intergenic region comprises a functional fragment of SEQ ID NO:100. In a specific embodiment, the Vκ-Jκ intergenic region is SEQ ID NO:100.

In one aspect, a mouse, a mouse cell (e.g., a mouse embryonic stem cell), a mouse embryo, and a mouse tissue are provided that comprise the recited human Vκ-Jκ intergenic region sequence, wherein the intergenic region sequence is ectopic. In a specific embodiment, the ectopic sequence is placed at a humanized endogenous mouse immunoglobulin locus.

In one aspect, an isolated nucleic acid construct is provided that comprises the recited human Vκ-Jκ intergenic region sequence. In one embodiment, the nucleic acid construct comprises targeting arms to target the human Vκ-Jκ intergenic region sequence to a mouse light chain locus. In a specific embodiment, the mouse light chain locus is a κ locus. In a specific embodiment, the targeting arms target the human Vκ-Jκ intergenic region to a modified endogenous mouse κ locus, wherein the targeting is to a position between a hVλ sequence and a hJλ sequence.

In one aspect, a genetically modified mouse is provided, wherein the mouse comprises no more than two light chain alleles, wherein the light chain alleles comprise (a) an unrearranged immunoglobulin human Vλ and a Jλ gene segment at an endogenous mouse light chain locus that comprises a mouse $C_L$ gene; and, (b) an unrearranged immunoglobulin $V_L$ and a $J_L$ gene segment at an endogenous mouse light chain locus that comprises a mouse $C_L$ gene.

In one embodiment, the endogenous mouse light chain locus is a κ locus. In another embodiment, the endogenous mouse light chain locus is a λ locus.

In one embodiment, the no more than two light chain alleles are selected from a κ allele and a λ allele, two κ alleles, and two λ alleles. In a specific embodiment, one of the two light chain alleles is a λ allele that comprises a Cλ2 gene.

In one embodiment, the mouse comprises one functional immunoglobulin light chain locus and one nonfunctional light chain locus, wherein the functional light chain locus comprises an unrearranged immunoglobulin human Vλ and a Jλ gene segment at an endogenous mouse κ light chain locus that comprises a mouse Cκ gene.

In one embodiment, the mouse comprises one functional immunoglobulin light chain locus and one nonfunctional light chain locus, wherein the functional light chain locus comprises an unrearranged immunoglobulin human Vλ and a Jλ gene segment at an endogenous mouse λ light chain locus that comprises a mouse Cλ gene. In one embodiment, the Cλ gene is Cλ2. In a specific embodiment, the mouse Cλ gene is at least 60%, at least 70%, at least 80%, at least 90%, at least 95%, or at least 98% identical to mouse Cλ2.

In one embodiment, the mouse further comprises at least one immunoglobulin heavy chain allele. In one embodiment, the at least one immunoglobulin heavy chain allele comprises a human $V_H$ gene segment, a human $D_H$ gene segment, and a human $J_H$ gene segment at an endogenous mouse heavy chain locus that comprises a human heavy chain gene that expresses a human/mouse heavy chain. In a specific embodiment, the mouse comprises two immunoglobulin heavy chain alleles, and the mouse expresses a human/mouse heavy chain.

In one embodiment, the mouse comprises a first light chain allele that comprises an unrearranged hVκ and an unrearranged hJκ, at an endogenous mouse κ locus that comprises an endogenous Cκ gene; and a second light chain allele that comprises an unrearranged hVλ and an unrearranged hJλ, at an endogenous mouse κ locus that comprises an endogenous Cκ gene. In a specific embodiment, the first and the second light chain alleles are the only functional light chain alleles of the genetically modified mouse. In a specific embodiment, the mouse comprises a nonfunctional λ locus. In one embodiment, the genetically modified mouse does not express a light chain that comprises a λ constant region.

In one embodiment, the mouse comprises a first light chain allele that comprises an unrearranged hVκ and an unrearranged hJκ, at an endogenous mouse κ locus that comprises an endogenous Cκ gene; and a second light chain allele that comprises an unrearranged hVλ and an unrearranged hJλ, at an endogenous mouse λ locus that comprises an endogenous Cλ gene. In a specific embodiment, the first and the second light chain alleles are the only functional light chain alleles of the genetically modified mouse. In one embodiment, the endogenous Cλ gene is Cλ2. In a specific embodiment, the mouse Cλ gene is at least 60%, at least 70%, at least 80%, at least 90%, at least 95%, or at least 98% identical to mouse Cλ2.

In one embodiment, the mouse comprises six immunoglobulin alleles, wherein the first allele comprises an unrearranged immunoglobulin Vλ and Jλ gene segment at an endogenous mouse κ light chain locus that comprises a mouse Cκ gene, the second comprises an unrearranged immunoglobulin Vκ and Jκ gene segment at an endogenous mouse κ light chain locus that comprises a mouse Cκ gene, the third comprises an unrearranged immunoglobulin Vλ and Jλ gene segment at an endogenous mouse λ light chain locus that comprises a mouse Cλ gene, the fourth and fifth each independently comprise an unrearranged $V_H$ and $D_H$ and $J_H$ gene segment at an endogenous mouse heavy chain locus that comprises a mouse heavy chain gene, and the sixth comprises either (a) an unrearranged immunoglobulin Vλ and Jλ gene segment at an endogenous mouse λ light chain locus that comprises a mouse Cλ gene, (b) a λ locus that is nonfunctional, or (c) a deletion in whole or in part of the λ locus.

In one embodiment, the first allele comprises an unrearranged hVλ and hJλ. In one embodiment, the second allele comprises an unrearranged hVκ and hJκ. In one embodiment, the third allele comprises an unrearranged hVλ and hJλ. In one embodiment, the fourth and fifth each independently comprise an unrearranged $hV_H$ and $hD_H$ and $hJ_H$. In one embodiment, the sixth allele comprises an endogenous mouse λ locus that is deleted in whole or in part.

In one embodiment, the mouse comprises six immunoglobulin alleles, wherein the first allele comprises an unrearranged immunoglobulin Vλ and Jλ gene segment at an endogenous mouse λ light chain locus that comprises a mouse Cλ gene, the second comprises an unrearranged immumoglobulin Vλ and Jλ gene segment at an endogenous mouse λ light chain locus that comprises a mouse Cλ gene, the third comprises an unrearranged immunoglobulin Vκ and Jκ gene segment at an endogenous mouse κ light chain locus that comprises a mouse Cκ gene, the fourth and fifth each independently comprise an unrearranged $V_H$ and $D_H$ and $J_H$ gene segment at an endogenous mouse heavy chain locus that comprises a mouse heavy chain gene, and the sixth comprises either (a) an unrearranged immunoglobulin Vκ and Jκ gene segment at an endogenous mouse κ light chain locus that comprises a mouse Cκ gene, (b) a κ locus that is nonfunctional, or (c) a deletion of one or more elements of the κ locus.

In one embodiment, the first allele comprises an unrearranged hVλ and hJλ gene segment. In one embodiment, the second allele comprises an unrearranged hVλ and hJλ gene segment. In one embodiment, the third allele comprises an unrearranged hVκ and hJκ gene segment. In one embodiment, the fourth and fifth each independently comprise an unrearranged $hV_H$ and $hD_H$ and $hJ_H$ gene segment. In one embodiment, the sixth allele comprises an endogenous mouse κ locus that is functionally silenced.

In one embodiment, the genetically modified mouse comprises a B cell that comprises a rearranged antibody gene comprising a rearranged hVλ domain operably linked to a mouse $C_L$ domain. In one embodiment, the mouse $C_L$ domain is selected from a mouse Cκ and a mouse Cλ domain. In a specific embodiment, the mouse Cλ domain is derived from a Cλ2 gene. In a specific embodiment, the mouse Cλ domain is derived from a Cλ domain that is at least 60%, at least 70%, at least 80%, at least 90%, at least 95%, or at least 98% identical to mouse Cλ2.

In one aspect, a genetically modified mouse is provided that expresses a Vλ region on a $C_L$ that is a Cκ. In one aspect, a genetically modified mouse is provided that expresses a hVλ region on a $C_L$ selected from a human Cκ, a human Cλ, or a mouse Cκ. In one aspect, a genetically modified mouse is provided that expresses a hVλ region on a mouse Cκ.

In one embodiment, about 10-50% of the splenocytes of the mouse are B cells (i.e., CD19-positive), or which about 9-28% express an immunoglobulin light chain comprising a hVλ domain fused to a mouse Cκ domain.

In a specific embodiment, about 23-34% of the splenocytes of the mouse are B cells (i.e., CD19-positive), or which about 9-11% express an immunoglobulin light chain comprising a hVλ domain fused to a mouse Cκ domain.

In a specific embodiment, about 19-31% of the splenocytes of the mouse are B cells (i.e., CD19-positive), or which about 9-17% express an immunoglobulin light chain comprising a hVλ domain fused to a mouse Cκ domain.

In a specific embodiment, about 21-38% of the splenocytes of the mouse are B cells (i.e., CD19-positive), or which about 24-27% express an immunoglobulin light chain comprising a hVλ domain fused to a mouse Cκ domain.

In a specific embodiment, about 10-14% of the splenocytes of the mouse are B cells (i.e., CD19-positive), or which about 9-13% express an immunoglobulin light chain comprising a hVλ domain fused to a mouse Cκ domain.

In a specific embodiment, about 31-48% of the splenocytes of the mouse are B cells (i.e., CD19-positive), or which about 15-21% express an immunoglobulin light chain comprising a hVλ domain fused to a mouse Cκ domain. In a specific embodiment, about 30-38% of the splenocytes of the mouse are B cells (i.e., CD19-positive), of which about 33-48% express an immunoglobulin light chain comprising a hVλ domain fused to a mouse Cκ domain.

In one embodiment, about 52-70% of the bone marrow of the mouse are B cells (i.e., CD19-positive), or which about 31-47% of the immature B cells (i.e., CD19-positive/B220-intermediate positive/IgM-positive) express an immunoglobulin light chain comprising a hVλ domain fused to a mouse Cκ domain.

In one embodiment, about 60% of the bone marrow of the mouse are B cells (i.e., CD19-positive), or which about 38.3% of the immature B cells (i.e., CD19-positive/B220-intermediate positive/IgM-positive) express an immunoglobulin light chain comprising a hVλ domain fused to a mouse Cκ domain.

In one embodiment, the mouse expresses an antibody comprising a light chain that comprises a variable domain derived from a human V and a human J gene segment, and a constant domain derived from a mouse constant region gene. In one embodiment, the mouse constant region gene is a Cκ gene. In another embodiment, the mouse constant region gene is a Cλ gene. In a specific embodiment, the Cλ region is Cλ2. In a specific embodiment, the mouse Cλ gene is derived from a Cλ gene that is at least 60%, at least 70%, at least 80%, at least 90%, at least 95%, or at least 98% identical to mouse Cλ2. In a specific embodiment, the antibody further comprises a heavy chain comprising a variable domain derived from a human V, a human D and a human J gene segment, and a heavy chain constant domain derived from a mouse heavy chain constant region gene. In one embodiment, the mouse heavy chain constant region gene comprises a hinge-$CH_2$—$CH_3$ sequence of a heavy chain constant domain. In another embodiment, the mouse heavy chain constant region gene comprises a $CH_1$-hinge-$CH_2$—$CH_3$ sequence of a heavy chain constant domain. In another embodiment, the mouse heavy chain constant region gene comprises a $CH_1$—$CH_2$—$CH_3$—$CH_4$ sequence of a heavy chain constant domain. In another embodiment, the mouse heavy chain constant region gene comprises a $CH_2$—$CH_3$—$CH_4$ sequence of a heavy chain constant domain.

In one embodiment, the mouse expresses an antibody comprising a light chain that comprises a rearranged human Vλ-Jλ sequence and a mouse Cκ sequence. In one embodiment, the rearranged human Vλ-Jλ sequence is derived from a rearrangement of hVλ gene segments selected from a 3-1, 4-3, 2-8, 3-9, 3-10, 2-14, 3-19, 2-23, 3-25, 1-40, 7-43, 1-44, 5-45, 7-46, 1-47, 9-49, and a 1-51 gene segment. In one embodiment, the rearranged human Vλ-Jλ sequence is derived from a rearrangement of hJλ gene segments selected from Jλ1, Jλ2, Jλ3, and a Jλ 7 gene segment.

In one embodiment, the mouse expresses an antibody comprising a light chain that comprises a rearranged immunoglobulin λ light chain variable region comprising a human Vλ/Jλ sequence selected from 3-1/1, 3-1/7, 4-3/1, 4-3/7, 2-8/1, 3-9/1, 3-10/1, 3-10/3, 3-10/7, 2-14/1, 3-19/1, 2-23/1, 3-25/1, 1-40/1, 1-40/2, 1-40/3, 1-40/7, 7-43/1, 7-43/3, 1-44/1, 1-44/7, 5-45/1, 5-45/2, 5-45/7, 7-46/1, 7-46/2, 7-46/7, 9-49/1, 9-49/2, 9-49/7 and 1-51/1. In a specific embodiment, the B cell expresses an antibody comprising a human immunoglobulin heavy chain variable domain fused with a mouse heavy chain constant domain, and a human immunoglobulin λ light chain variable domain fused with a mouse κ light chain constant domain.

In one aspect, a mouse is provided that expresses an antibody comprising (a) a heavy chain comprising a heavy chain variable domain derived from an unrearranged human heavy chain variable region gene segment, wherein the heavy chain variable domain is fused to a mouse heavy chain constant ($C_H$) region; and, (b) a light chain comprising a light chain variable domain derived from an unrearranged hVλ and a hJλ, wherein the light chain variable domain is fused to a mouse $C_L$ region.

In one embodiment, the mouse comprises (i) a heavy chain locus that comprises a replacement of all or substantially all functional endogenous mouse V, D and J gene segments with all or substantially all functional human V, D, and J gene segments, a mouse $C_H$ gene, (ii) a first κ light chain locus comprising a replacement of all or substantially all functional endogenous mouse Vκ and Jκ gene segments with all, substantially all, or a plurality of, functional hVλ and hJλ gene segments, and a mouse Cl gene, (iii) a second κ light chain locus comprising a replacement of all or substantially all functional endogenous mouse Vκ and Jκ gene segments with all, substantially all, or a plurality of, functional hVκ and hJκ gene segments, and a mouse Cκ gene. In one embodiment, the mouse does not express an antibody that comprises a Cλ region. In one embodiment, the mouse comprises a deletion of a Cλ gene and/or a Vλ and/or a Jλ gene segment. In one embodiment, the mouse comprises a nonfunctional λ light chain locus. In a specific embodiment, the λ light chain locus is deleted in whole or in part.

In one embodiment, the mouse comprises (i) a heavy chain locus that comprises a replacement of all or substantially all functional endogenous mouse V, D and J gene segments with all or substantially all functional human V, D, and J gene segments, a mouse $C_H$ gene, (ii) a first λ light chain locus comprising a replacement of all or substantially all functional endogenous mouse Vλ and Jλ gene segments with all, substantially all, or a plurality of, functional hVλ and hJλ gene segments, and a mouse Cλ gene, (iii) a second λ light chain locus comprising a replacement of all or substantially all functional endogenous mouse Vλ and Jλ gene segments with all, substantially all, or a plurality of, functional hVλ and hJλ gene segments, and a mouse Cλ gene. In a specific embodiment, the mouse Cλ gene is Cλ2. In a specific embodiment, the mouse Cλ gene is derived from a Cλ gene that is at least 60%, at least 70%, at least 80%, at least 90%, at least 95%, or at least 98% identical to mouse Cλ2.

In one embodiment, the mouse comprises a deletion of a Cκ gene and/or a Vκ and/or a Jκ gene segment. In one embodiment, the mouse comprises a nonfunctional κ light chain locus.

In one aspect, a genetically modified mouse that expresses an antibody is provided, wherein greater than 10%, greater than 15%, greater than 20%, greater than 25%, greater than 30%, greater than 35%, greater than 40%, greater than 60%, greater than 70%, greater than 80%, or greater than 90% of total IgG antibody produced by the mouse comprises a λ-derived variable domain, and wherein the mouse expresses antibodies comprising a κ-derived variable domain fused with a mouse Cκ region. In specific embodiments, about 15-40%, 20-40%, 25-40%, 30-40%, or 35-40% of total antibody produced by the mouse comprises a λ-derived variable domain.

In one embodiment, the λ-derived variable domain is derived from a hVλ and a hJλ. In one embodiment, the λ-derived variable domain is in a light chain that comprises a mouse Cκ region. In a specific embodiment, the λ-derived variable region is in a light chain that comprises a mouse Cλ region. In another specific embodiment, the Cλ region is a Cλ2 region. In one embodiment, the κ-derived variable domain is derived from a hVκ and a hJκ, and in a specific embodiment is in a light chain that comprises a mouse Cκ region.

In one aspect, an isolated DNA construct is provided that comprises an upstream homology arm and a downstream homology arm, wherein the upstream and the downstream homology arms target the construct to a mouse κ locus, and the construct comprises a functional unrearranged hVλ segment and a functional unrearranged hJλ segment, and a selection or marker sequence.

In one aspect, an isolated DNA construct is provided, comprising, from 5' to 3' with respect to the direction of transcription, a targeting arm for targeting a mouse λ sequence upstream of mouse Vλ2, a selection cassette flanked 5' and 3' with recombinase recognition sites, and a targeting arm for targeting a mouse λ sequence 3' of mouse Jλ2. In one embodiment, the selection cassette is a Frt'ed Hyg-TK cassette. In one embodiment, the 3' targeting arm comprises mouse Cλ2, Jλ 4, Cλ 4, and mouse enhancer 2.4.

In one aspect, an isolated DNA construct is provided, comprising, from 5' to 3' with respect to the direction of transcription, a targeting arm for targeting the mouse λ locus 5' with respect to Vλ1, a selection cassette flanked 5' and 3' with recombinase recognition sites, and a 3' targeting arm for targeting a mouse λ sequence 3' with respect to mouse Cλ1. In one embodiment, the selection cassette is a loxed neomycin cassette. In one embodiment, the 3' targeting arm comprises the mouse λ 3' enhancer and mouse λ 3' enhancer 3.1.

In one aspect, an isolated DNA construct is provided, comprising from 5' to 3' with respect to the direction of transcription, a targeting arm for targeting the mouse λ locus 5' with respect to Vλ2, a selection cassette flanked 5' and 3' with recombinase recognition sites, and a 3' targeting arm for targeting a mouse λ sequence 3' with respect to mouse Jλ2 and 5' with respect to mouse Cλ2. In one embodiment, the selection cassette is a Frt'ed hygromycin-TK cassette. In one embodiment, the 3' targeting arm comprises the mouse Cλ 2-Jλ4-Cλ 4 gene segments and mouse λ enhancer 2.4.

In one aspect, an isolated DNA construct is provided, comprising, from 5' to 3' with respect to the direction of transcription, a targeting arm for targeting the mouse λ locus 5' with respect to Vλ2, a selection cassette flanked 5' and 3' with recombinase recognition sites, a human genomic fragment comprising a contiguous region of the human λ light chain locus from hVλ3-12 downstream to the end of hJλ1, and a 3' targeting arm for targeting a mouse λ sequence 3' with respect to mouse Jλ2. In one embodiment, the selection cassette is a Frt'ed neomycin cassette. In one embodiment, the 3' targeting arm comprises the mouse Cλ2-Jλ4-Cλ 4 gene segments and mouse λ enhancer 2.4.

In one aspect, an isolated DNA construct is provided, comprising a contiguous region of the human λ light chain locus from hVλ3-12 downstream to the end of hJλ1.

In one aspect, an isolated DNA construct is provided, comprising, from 5' to 3' with respect to the direction of transcription, a targeting arm for targeting the mouse λ locus 5' with respect to Vλ2, a selection cassette flanked 5' and 3' with recombinase recognition sites and a human genomic fragment comprising a contiguous region of the human λ light chain locus from hVλ3-27 downstream to the end of hVλ2-8. In one embodiment, the selection cassette is a Frt'ed hygromycin cassette. In one embodiment, the human genomic fragment comprises a 3' targeting arm. In a specific embodiment, the 3' targeting arm comprises about 53 kb of the human λ light chain locus from hVλ3-12 downstream to the end of hVλ2-8.

In one aspect, an isolated DNA construct is provided, comprising a contiguous region of the human λ light chain locus from hVλ3-27 downstream to the end of hVλ3-12.

In one aspect, an isolated DNA construct is provided, comprising, from 5' to 3' with respect to the direction of transcription, a targeting arm for targeting the mouse λ locus 5' with respect to Vλ2, a selection cassette flanked 5' and 3' with recombinase recognition sites, a first human genomic fragment comprising a contiguous region of the human λ light chain locus from hVλ5-52 downstream to the end of hVλ1-40, a restriction enzyme site, and a second human genomic fragment comprising a contiguous region of the human λ light chain locus from hVλ3-29 downstream to the end of hVλ82K. In one embodiment, the selection cassette is a Frt'ed neomycin cassette. In one embodiment, the restriction enzyme site is a site for a homing endonuclease. In a specific embodiment, the homing endonuclease is PI-SceI. In on embodiment, the second human genomic fragment is a 3' targeting arm. In a specific embodiment, the 3' targeting arm comprises about 27 kb of the human λ light chain locus from hVλ3-29 downstream to the end of hVλ82K.

In one aspect, an isolated DNA construct is provided, comprising a contiguous region of the human λ light chain locus from hVλ5-52 downstream to the end of hVλ1-40.

In one aspect, an isolated DNA construct is provided, comprising, from 5' to 3' with respect to the direction of transcription, a targeting arm for targeting the mouse κ locus 5' with respect to the endogenous Vκ gene segments, two juxtaposed recombinase recognition sites, a selection cassette 3' to the juxtaposed recombinase recognition sites, and a 3' targeting arm for targeting a mouse κ sequence 5' with respect to the κ light chain variable gene segments. In one embodiment, the juxtaposed recombinase recognition sites are in opposite orientation with respect to one another. In a specific embodiment, the recombinase recognition sites are different. In another specific embodiment, the recombinase recognition sites are a loxP site and a lox511 site. In one embodiment, the selection cassette is a neomycin cassette.

In one aspect, an isolated DNA construct is provided, comprising, from 5' to 3' with respect to the direction of transcription, a targeting arm for targeting the mouse κ locus 5' with respect to the mouse Jκ gene segments, a selection cassette, a recombinase recognition site 3' to the selection cassette, and a 3' targeting arm for targeting a mouse κ sequence 3' with respect to the mouse Jκ gene segments and 5' to the mouse κ intronic enhancer. In one embodiment, the selection cassette is a hygromycin-TK cassette. In one embodiment, the recombinase recognition site is in the same direction with respect to transcription as the selection cassette. In a specific embodiment, the recombinase recognition site is a loxP site.

In one aspect, an isolated DNA construct is provided, comprising, from 5' to 3' with respect to the direction of transcription, a first mouse genomic fragment comprising sequence 5' of the endogenous mouse Vκ gene segments, a first recombinase recognition site, a second recombinase recognition site, and a second mouse genomic fragment comprising sequence 3' of the endogenous mouse Jκ gene segments and 5' of the mouse κ intronic enhancer.

In one aspect, a genetically modified mouse is provided, wherein the genetic modification comprises a modification with one or more of the DNA constructs described above or herein.

In one aspect, use of an isolated DNA construct to make a mouse as described herein is provided. In one aspect, use of an isolated DNA construct as described herein in a method for making an antigen-binding protein is provided.

In one aspect, a non-human stem cell is provided that comprises a targeting vector that comprises a DNA construct as described above and herein. In one aspect, a non-human stem cell is provided, wherein the non-human stem cell is derived from a mouse described herein.

In one embodiment, the non-human stem cell is an embryonic stem (ES) cell. In a specific embodiment, the ES cell is a mouse ES cell.

In one aspect, use of a non-human stem cell as described herein to make a mouse as described herein is provided. In one aspect, use of a non-human stem cell as described herein to make an antigen-binding protein is provided.

In one aspect, a mouse embryo is provided, wherein the mouse embryo comprises a genetic modification as provided herein. In one embodiment, a host mouse embryo that comprises a donor ES cell is provided, wherein the donor ES cell comprises a genetic modification as described herein. In one embodiment, the mouse embryo is a pre-morula stage embryo. In a specific embodiment, the pre-morula stage embryo is a 4-cell stage embryo or an 8-cell stage embryo. In another specific embodiment, the mouse embryo is a blastocyst.

In one aspect, use of a mouse embryo as described herein to make a mouse as described herein is provided. In one aspect, use of a mouse embryo as described herein to make an antigen-binding protein is provided.

In one aspect, a non-human cell is provided, wherein the non-human cell comprises a rearranged immunoglobulin light chain gene sequence derived from a genetically modified mouse as described herein. In one embodiment, the cell is a B cell. In one embodiment, the cell is a hybridoma. In one embodiment, the cell encodes an immunoglobulin light chain variable domain and/or an immunoglobulin heavy chain variable domain that is somatically mutated.

In one aspect, a non-human cell is provided, wherein the non-human cell comprises a rearranged immunoglobulin light chain gene sequence derived from a genetically modified mouse as described herein. In one embodiment, the cell is a B cell. In one embodiment, the cell is a hybridoma. In one embodiment, the cell encodes an immunoglobulin light chain variable domain and/or an immunoglobulin heavy chain variable domain that is somatically mutated.

In one aspect, use of a non-human cell as described herein to make a mouse as described herein is provided. In one aspect, use of a non-human cell as described herein to make an antigen-binding protein is provided.

In one aspect, a mouse B cell is provided that expresses an immunoglobulin light chain that comprises (a) a variable region derived from a hVλ gene segment and a hJλ gene segment; and, (b) a mouse $C_L$ gene. In one embodiment, the mouse $C_L$ gene is selected from a Cκ and a Cλ gene. In a specific embodiment, the Cλ gene is Cλ2. In a specific embodiment, the mouse Cλ gene is derived from a Cλ gene that is at least 60%, at least 70%, at least 80%, at least 90%, at least 95%, or at least 98% identical to mouse Cλ2. In one embodiment, the mouse B cell further expresses a cognate heavy chain that comprises (c) a variable region derived from a $hV_H$, a $hD_H$, and (d) a $hJ_H$ segment. In one embodiment, the B cell does not comprise a rearranged λ gene. In another embodiment, the B cell does not comprise a rearranged κ gene.

In one aspect, a method for making an antibody in a genetically modified mouse is provided, comprising: (a) exposing a genetically modified mouse to an antigen, wherein the mouse has a genome comprising at least one hVλ and at least one hJλ at an endogenous light chain locus, wherein the endogenous light chain locus comprises a mouse $C_L$ gene; (b) allowing the genetically modified mouse to develop an immune response to the antigen; and, (c) isolating from the mouse of (b) an antibody that specifically recognizes the antigen, or isolating from the mouse of (b) a cell comprising an immunoglobulin domain that specifically recognizes the antigen, wherein the antibody comprises a light chain derived from a hVλ, a hJλ and a mouse $C_L$ gene. In a specific embodiment, the mouse $C_L$ gene is a mouse Cκ gene.

In one embodiment, a method for making an antibody in a genetically modified mouse is provided, comprising: (a) exposing a genetically modified mouse to an antigen, wherein the mouse has a genome comprising at least one hVλ at an endogenous κ locus and at least one hJλ at the κ locus, wherein the κ locus comprises a mouse Cκ gene; (b) allowing the genetically modified mouse to develop an immune response to the antigen; and, (c) isolating from the mouse of (b) an antibody that specifically recognizes the antigen, or isolating from the mouse of (b) a cell comprising an immunoglobulin domain that specifically recognizes the antigen, wherein the antibody comprises a light chain derived from a hVλ, a hJλ and a mouse Cκ gene.

In one embodiment, the κ light chain constant gene is selected from a human Cκ gene and a mouse Cκ gene.

In one embodiment, a method for making an antibody in a genetically modified mouse is provided, comprising: (a) exposing a genetically modified mouse to an antigen, wherein the mouse has a genome comprising at least one hVλ at a λ light chain locus and at least one Jλ at the λ light chain locus, wherein the λ light chain locus comprises a mouse Cλ gene; (b) allowing the genetically modified mouse to develop an immune response to the antigen; and, (c) isolating from the mouse of (b) an antibody that specifically recognizes the antigen, or isolating from the mouse of (b) a cell comprising an immunoglobulin domain that specifically recognizes the antigen, or identifying in the mouse of B a nucleic acid sequence encoding a heavy and/or light chain variable domain that binds the antigen, wherein the antibody comprises a light chain derived from a hVλ, a hJλ and a mouse Cλ gene.

In one embodiment, the λ light chain constant gene is selected from a human Cλ gene and a mouse Cλ gene. In one embodiment, the λ light chain constant gene is a human Cλ gene. In a specific embodiment, the human Cλ gene is selected from Cλ1, Cλ2, Cλ3 and Cλ7. In one embodiment, the λ light chain constant gene is a mouse Cλ gene. In a specific embodiment, the mouse Cλ gene is selected from Cλ1, Cλ2 and Cλ3. In a more specific embodiment, the mouse Cλ gene is Cλ2. In another specific embodiment, the mouse Cλ gene is derived from a Cλ gene that is at least 60%, at least 70%, at least 80%, at least 90%, at least 95%, or at least 98% identical to mouse Cλ2.

In one aspect, a method for making a rearranged antibody gene in a genetically modified mouse is provided, comprising: (a) exposing a genetically modified mouse to an antigen, wherein the genetic modification comprises a hVλ and a hJλ at an endogenous light chain locus, wherein the endogenous light chain locus comprises a mouse $C_L$ gene or functional fragment thereof; and, (b) identifying a rearranged immunoglobulin gene in said mouse, wherein the rearranged immunoglobulin gene comprises a λ light chain variable region gene segment and a $C_L$ gene or functional fragment thereof.

In one embodiment, the method further comprises cloning a nucleic acid sequence encoding a heavy and/or light chain variable region from the mouse, wherein the heavy and/or light chain variable region is from an antibody that comprises a human Vλ and a mouse $C_L$.

In one embodiment, the mouse $C_L$ gene or functional fragment thereof is selected from a human $C_L$ gene and a mouse $C_L$ gene, or functional fragment thereof.

In one embodiment, a method for making a rearranged antibody gene in a genetically modified mouse is provided, comprising: (a) exposing a genetically modified mouse to an antigen, wherein the genetic modification comprises a hVλ and a hJλ at a κ light chain locus, wherein the κ light chain locus comprises a mouse Cl gene or functional fragment thereof; and, (b) identifying a rearranged immunoglobulin gene in said mouse, wherein the rearranged immunoglobulin gene comprises a λ light chain variable region gene segment and a Cl gene or functional fragment thereof.

In one embodiment, the κ light chain constant gene or functional fragment thereof is selected from a human Cκ gene and a mouse Cκ gene, or a functional fragment thereof.

In one embodiment, the method further comprises cloning a nucleic acid sequence encoding a heavy and/or light chain variable region from the mouse, wherein the heavy and/or light chain variable region is from an antibody that comprises a human Vλ and a mouse Cκ.

In one embodiment, a method for making a rearranged antibody gene in a genetically modified mouse is provided, comprising: (a) exposing a genetically modified mouse to an antigen, wherein the genetic modification comprises a hVλ and a hJλ at a mouse λ light chain locus, wherein the λ light chain locus comprises a mouse Cλ gene or functional fragment thereof; and, (b) identifying a rearranged immunoglobulin gene in said mouse, wherein the rearranged immunoglobulin gene comprises a λ light chain variable region gene segment and a Cl gene or functional fragment thereof.

In one embodiment, the λ light chain constant gene or functional fragment thereof is selected from a human Cλ gene and a mouse Cλ gene, or a functional fragment thereof. In a specific embodiment, the λ light chain constant gene is a mouse Cλ gene, or a functional fragment thereof.

In one embodiment, the method further comprises cloning a nucleic acid sequence encoding a heavy and/or light chain variable region from the mouse, wherein the heavy and/or light chain variable region is from an antibody that comprises a human Vλ and a mouse Cλ.

In one aspect, a method for making an antibody is provided, comprising exposing a mouse as described herein to an antigen, allowing the mouse to mount an immune response that comprises making an antibody that specifically binds the antigen, identifying a rearranged nucleic acid sequence in the mouse that encodes heavy chain and a rearranged nucleic acid sequence in the mouse that encodes a cognate light chain variable domain sequence of an antibody, wherein the antibody specifically binds the antigen, and employing the nucleic acid sequences of the heavy and light chain variable domains fused to human constant domains to make a desired antibody, wherein the desired antibody comprises a light chain that comprises a Vλ domain fused to a $C_L$ domain. In one embodiment, the Vλ domain is human and the $C_L$ domain is a human or mouse Cλ domain. In one embodiment, the Vλ domain is mouse and the $C_L$ domain is a human or mouse Cκ domain.

In one embodiment, a method for making an antibody is provided, comprising exposing a mouse as described herein to an antigen, allowing the mouse to mount an immune response that comprises making an antibody that specifically binds the antigen, identifying a rearranged nucleic acid sequence in the mouse that encodes a heavy chain and a rearranged nucleic acid sequence in the mouse that encodes a cognate light chain variable domain sequence of an antibody, wherein the antibody specifically binds the antigen, and employing the nucleic acid sequences of the heavy and light chain variable domains fused to nucleic acid sequences of human constant domains to make a desired antibody, wherein the desired antibody comprises a light chain that comprises a Vλ domain fused to a Cκ domain.

In one embodiment, a method for making an antibody is provided, comprising exposing a mouse as described herein to an antigen, allowing the mouse to mount an immune response that comprises making an antibody that specifically binds the antigen, identifying a rearranged nucleic acid sequence in the mouse that encodes a heavy chain variable domain and a rearranged nucleic acid sequence that encodes a cognate light chain variable domain sequence of an antibody, wherein the antibody specifically binds the antigen, and employing the nucleic acid sequences fused to nucleic acid sequences that encode a human heavy chain constant domain and a human light chain constant domain to make an antibody derived from human sequences, wherein the antibody that specifically binds the antigen comprises a light chain that comprises a human Vλ domain fused to a mouse Cλ region.

In one embodiment, the mouse Cλ region is selected from Cλ1, Cλ2 and Cλ3. In a specific embodiment, the mouse Cλ region is Cλ2.

In one aspect, a method for making a rearranged antibody light chain variable region gene sequence is provided, comprising (a) exposing a mouse as described herein to an antigen; (b) allowing the mouse to mount an immune response; (c) identifying a cell in the mouse that comprises a nucleic acid sequence that encodes a rearranged human Vλ domain sequence fused with a mouse $C_L$ domain, wherein the cell also encodes a cognate heavy chain comprising a human $V_H$ domain and a mouse $C_H$ domain, and wherein the cell expresses an antibody that binds the antigen; (d) cloning from the cell a nucleic acid sequence encoding the human Vλ domain and a nucleic acid sequence encoding the cognate human $V_H$ domain; and, (e) using the cloned nucleic acid sequence encoding the human Vλ domain and the cloned nucleic acid sequence encoding the cognate human $V_H$ domain to make a fully human antibody.

In one embodiment, a method for making a rearranged antibody light chain variable region gene sequence is provided, comprising (a) exposing a mouse as described in this disclosure to an antigen; (b) allowing the mouse to mount an immune response; (c) identifying a cell in the mouse that comprises a nucleic acid sequence that encodes a rearranged human Vλ domain sequence contiguous on the same nucleic acid molecule with a nucleic acid sequence encoding a mouse Cκ domain, wherein the cell also encodes a cognate heavy chain comprising a human $V_H$ domain and a mouse $C_H$ domain, and wherein the cell expresses an antibody that binds the antigen; (d) cloning from the cell a nucleic acids sequence encoding the human Vλ domain and a nucleic acid sequence encoding the cognate human $V_H$ domain; and, (e) using the cloned nucleic acid sequence encoding the human Vλ domain and the cloned nucleic acid sequence encoding the cognate human $V_H$ domain to make a fully human antibody.

In one embodiment, a method for making a rearranged antibody light chain variable region gene sequence is provided, comprising (a) exposing a mouse as described herein to an antigen; (b) allowing the mouse to mount an immune response to the antigen; (c) identifying a cell in the mouse that comprises DNA that encodes a rearranged human Vλ domain sequence fused with a mouse Cλ domain, wherein the cell also encodes a cognate heavy chain comprising a human $V_H$ domain and a mouse $C_H$ domain, and wherein the cell expresses an antibody that binds the antigen; (d) cloning from the cell a nucleic acid sequence encoding the rearranged human Vλ domain and a nucleic acid sequence encoding the cognate human $V_H$ domain; and, (e) using the cloned nucleic acid sequence encoding the human Vλ domain and the cloned nucleic acid sequence encoding the cognate human $V_H$ domain to make a fully human antibody. In one embodiment, the mouse Cλ domain is mouse Cλ2. In a specific embodiment, the mouse Cλ domain is derived from a Cλ gene that is at least 60%, at least 70%, at least 80%, at least 90%, at least 95%, or at least 98% identical to mouse Cλ2.

In one aspect, a genetically modified mouse is provided that expresses a human λ-derived light chain fused to an endogenous light chain constant region ($C_L$), wherein the mouse, upon immunization with antigen, makes an antibody comprising a human Vλ domain fused to a mouse $C_L$ domain. In one embodiment, the mouse $C_L$ domain is selected from a Cκ domain and a Cλ domain. In one embodiment, the mouse $C_L$ domain is a Cκ domain. In one embodiment, the mouse $C_L$ domain is a Cλ domain. In a specific embodiment, the Cλ domain is Cλ2. In a specific embodiment, the mouse Cλ domain is derived from a Cλ gene that is at least 60%, at least 70%, at least 80%, at least 90%, at least 95%, or at least 98% identical to mouse Cλ2.

In one aspect, a genetically modified mouse comprising a modified endogenous κ or λ light chain locus as described herein, is provided that expresses a plurality of immunoglobulin λ light chains associated with a plurality of immunoglobulin heavy chains. In one embodiment, the heavy chain comprises a human sequence. In various embodiments, the human sequence is selected from a variable sequence, a $C_H1$, a hinge, a $C_H2$, a $C_H3$, and a combination thereof. In one embodiment, the plurality of immunoglobulin λ light chains comprises a human sequence. In various embodiments, the human sequence is selected from a variable sequence, a constant sequence, and a combination thereof. In one embodiment, the mouse comprises a disabled endogenous immunoglobulin locus and expresses the heavy chain and/or the λ light chain from a transgene or extrachromosomal episome. In one embodiment, the mouse comprises a replacement at an endogenous mouse locus of some or all endogenous mouse heavy chain gene segments (i.e., V, D, J), and/or some or all endogenous mouse heavy chain constant sequences (e.g., $C_H1$, hinge, $C_H2$, $C_H3$, or a combination thereof), and/or some or all endogenous mouse light chain sequences (e.g., V, J, constant, or a combination thereof), with one or more human immunoglobulin sequences.

In one aspect, a mouse suitable for making antibodies that have a human λ-derived light chain is provided, wherein all or substantially all antibodies made in the mouse are expressed with a human λ-derived light chain. In one embodiment, the human λ-derived light chain is expressed from an endogenous light chain locus. In one embodiment, the endogenous light chain locus is a κ light chain locus. In a specific embodiment, the κ light chain locus is a mouse κ light chain locus.

In one aspect, a method for making a λ-derived light chain for a human antibody is provided, comprising obtaining from a mouse as described herein a light chain sequence and a heavy chain sequence, and employing the light chain sequence and the heavy chain sequence in making a human antibody.

In one aspect, a method for making an antigen-binding protein is provided, comprising exposing a mouse as described herein to an antigen; allowing the mouse to mount an immune response; and obtaining from the mouse an antigen-binding protein that binds the antigen, or obtaining from the mouse a sequence to be employed in making an antigen-binding protein that binds the antigen.

In one aspect, a cell derived from a mouse as described herein is provided. In one embodiment, the cell is selected from an embryonic stem cell, a pluripotent cell, an induced pluripotent cell, a B cell, and a hybridoma.

In one aspect, a cell is provided that comprises a genetic modification as described herein. In one embodiment, the cell is a mouse cell. In one embodiment, the cell is selected from a hybridoma and a quadroma. In one embodiment, the cell expresses an immunoglobulin light chain that comprises a human λ variable sequence fused with a mouse constant sequence. In a specific embodiment, the mouse constant sequence is a mouse κ constant sequence.

In one aspect, a tissue derived from a mouse as described herein is provided.

In one aspect, use of a mouse or a cell as described herein to make an antigen-binding protein is provided. In one embodiment, the antigen-binding protein is a human protein. In one embodiment, the human protein is a human antibody.

In one aspect, an antigen-binding protein made by a mouse, cell, tissue, or method as described herein is provided. In one embodiment, the antigen-binding protein is a human protein. In one embodiment, the human protein is a human antibody.

Any of the embodiments and aspects described herein can be used in conjunction with one another, unless otherwise indicated or apparent from the context. Other embodiments will become apparent to those skilled in the art from a review of the ensuing description.

BRIEF DESCRIPTION OF THE FIGURES

FIG. 11 shows a nucleotide sequence alignment of the Vλ-Jλ-Cκ junction of eighteen independent RT-PCR clones amplified from splenocyte RNA of mice bearing human λ light chain gene sequences at an endogenous mouse κ light chain locus. A6=SEQ ID NO:57; B6=SEQ ID NO:58; F6=SEQ ID NO:59; B7=SEQ ID NO:60; E7=SEQ ID NO:61; F7=SEQ ID NO:62; C8=SEQ ID NO:63; E12=SEQ ID NO:64; 1-4=SEQ ID NO:65; 1-20=SEQ ID NO:66; 3B43=SEQ ID NO:67; 5-8=SEQ ID NO:68; 5-19=SEQ ID NO:69; 1010=SEQ ID NO:70; 11A1=SEQ ID NO:71; 7A8=SEQ ID NO:72; 3A3=SEQ ID NO:73; 2-7=SEQ ID NO:74. Lower case bases indicate non-germline bases resulting from either mutation and/or N addition during recombination. Consensus amino acids within the Framework 4 region (FWR4) encoded by the nucleotide sequence of hJλ1 and mouse Cκ are noted at the bottom of the sequence alignment.

FIG. 12 shows a nucleotide sequence alignment of the Vλ-Jλ-Cκ junction of twelve independent RT-PCR clones amplified from splenocyte RNA of mice bearing human λ light chain gene sequences including a contiguous human Vκ-Jκ genomic sequence at an endogenous mouse κ light chain locus. 5-2=SEQ ID NO:87; 2-5=SEQ ID NO:88; 1-3=SEQ ID NO:89; 4B-1=SEQ ID NO:90; 3B-5=SEQ ID NO:91; 7A-1=SEQ ID NO:92; 5-1=SEQ ID NO:93; 4A-1=SEQ ID NO:94; 11A-1=SEQ ID NO:95; 5-7=SEQ ID NO:96; 5-4=SEQ ID NO:97; 2-3=SEQ ID NO:98. Lower case bases indicate non-germline bases resulting from either mutation and/or N addition during recombination. Consensus amino acids within the Framework 4 region (FWR4) encoded by the nucleotide sequence of each human Jλ and mouse Cκ are noted at the bottom of the sequence alignment.

FIG. 13 shows a nucleotide sequence alignment of the Vλ-Jλ-Cκ junction of three independent RT-PCR clones amplified from splenocyte RNA of mice bearing human λ light chain gene sequences at an endogenous mouse λ light chain locus. 2D1=SEQ ID NO:101; 2D9=SEQ ID NO:102; 3E15=SEQ ID NO:103. Lower case bases indicate non-germline bases resulting from either mutation and/or N addition during recombination. Consensus amino acids within the Framework 4 region (FWR4) encoded by the nucleotide sequence of hJλ1 and mouse Cλ2 are noted at the bottom of the sequence alignment.

DETAILED DESCRIPTION

Figure 1:
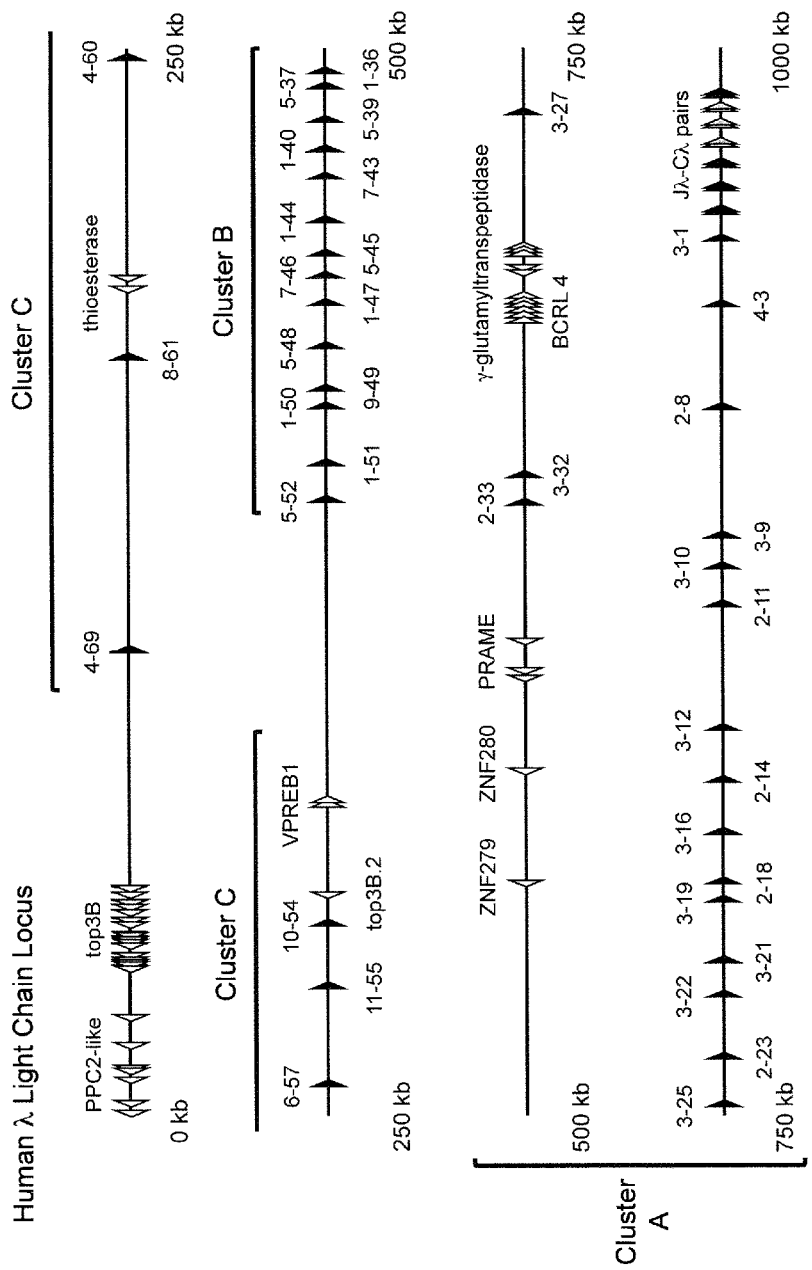
FIG. 1 shows a detailed illustration, not to scale, of the human λ light chain locus including the clusters of Vλ gene segments (A, B and C) and the Jλ and Cλ region pairs (J-C pairs)

Although specific features of various embodiments are discussed in detail, the descriptions of the specific aspects, embodiments, and examples do not limit the subject matter of the claims; it is the claims that describe the scope of the invention. All terms and phrases used in this disclosure include the meanings normally ascribed to them in the art.

The term "contiguous" includes reference to occurrence on the same nucleic acid molecule, e.g., two nucleic acid sequences are "contiguous" if they occur on the same nucleic molecule but are interrupted by another nucleic acid sequence. For example, a rearranged V(D)J sequence is "contiguous" with a constant region gene sequence, although the final codon of the V(D)J sequence is not followed immediately by the first codon of the constant region sequence. In another example, two V gene segment sequences are "contiguous" if they occur on the same genomic fragment, although they may be separated by sequence that does not encode a codon of the V region, e.g., they may be separated by a regulatory sequence, e.g., a promoter or other noncoding sequence. In one embodiment, a contiguous sequence includes a genomic fragment that contains genomic sequences arranged as found in a wild-type genome.

The phrase "derived from" when used concerning a variable region "derived from" a cited gene or gene segment includes the ability to trace the sequence back to a particular unrearranged gene segment or gene segments that were rearranged to form a gene that expresses the variable domain (accounting for, where applicable, splice differences and somatic mutations).

The phrase "functional" when used concerning a variable region gene segment or joining gene segment refers to usage in an expressed antibody repertoire; e.g., in humans Vλ gene segments 3-1, 4-3, 2-8, etc. are functional, whereas Vλ gene segments 3-2, 3-4, 2-5, etc. are nonfunctional.

A "heavy chain locus" includes a location on a chromosome, e.g., a mouse chromosome, wherein in a wild-type mouse heavy chain variable ($V_H$), heavy chain diversity ($D_H$), heavy chain joining ($J_H$), and heavy chain constant ($C_H$) region DNA sequences are found.

A "κ locus" includes a location on a chromosome, e.g., a mouse chromosome, wherein in a wild-type mouse κ variable (Vκ), κ joining (Jκ), and κ constant (Cκ) region DNA sequences are found.

A "λ locus" includes a location on a chromosome, e.g., a mouse chromosome, wherein in a wild-type mouse λ variable (Vλ), λ joining (Jκ), and λ constant (Cλ) region DNA sequences are found.

The term "unrearranged" includes the state of an immunoglobulin locus wherein V gene segments and J gene segments (for heavy chains, D gene segments as well) are maintained separately but are capable of being joined to form a rearranged V(D)J gene that comprises a single V,(D),J of the V(D)J repertoire.

Mice Expressing Human λ, Variable Domains

Mice that express antibodies that are fully human, or partly human and partly mouse, have previously been reported. VELOCIMMUNE® genetically engineered mice comprise a replacement of unrearranged V(D)J gene segments at endogenous mouse loci with human V(D)J gene segments. VELOCIMMUNE® mice express chimeric antibodies having human variable domains and mouse constant domains (see, e.g., U.S. Pat. No. 7,605,237). Most other reports concern mice that express fully human antibodies from fully human transgenes in mice that have disabled endogenous immunoglobulin loci.

Antibody light chains are encoded by one of two separate loci: kappa (κ) and lambda (2λ. Mouse antibody light chains are primarily of the κ type. Mice that make mouse antibodies, and modified mice that make fully human or chimeric human-mouse antibodies, display a bias in light chain usage. Humans also exhibit light chain bias, but not so pronounced as in mice; the ratio of κ light chains to λ light chains in mice is about 95:5, whereas in humans the ratio is about 60:40. The more pronounced bias in mice is not thought to severely affect antibody diversity, because in mice the λ variable locus is not so diverse in the first instance. This is not so in humans. The human λ light chain locus is richly diverse.

The human λ light chain locus extends over 1,000 kb and contains over 80 genes that encode variable (V) or joining (J) segments (FIG. 1). Within the human λ light chain locus, over half of all observed Vλ domains are encoded by the gene segments 1-40, 1-44, 2-8, 2-14, and 3-21. Overall, about 30 or so of the human Vλ gene segments are believed to be functional. There are seven Jλ gene segments, only four of which are regarded as generally functional Jλ gene segments Jλ1, Jλ2, Jλ3, and Jλ 7.

The λ light chain locus in humans is similar in structure to the | locus of both mice and humans in that the human λ light chain locus has several variable region gene segments that are capable of recombining to form a functional light chain protein. The human λ light chain locus contains approximately 70 V gene segments and 7 Jλ-Cλ gene segment pairs. Only four of these Jλ-Cλ gene segment pairs appear to be functional. In some alleles, a fifth Jλ-Cλ gene segment pair is reportedly a pseudo gene (Cλ6). The 70 Vλ gene segments appear to contain 38 functional gene segments. The 70 Vλ sequences are arranged in three clusters, all of which contain different members of distinct V gene family groups (clusters A, B and C; FIG. 1). This is a potentially rich source of relatively untapped diversity for generating antibodies with human V regions in non-human animals.

Figure 2:
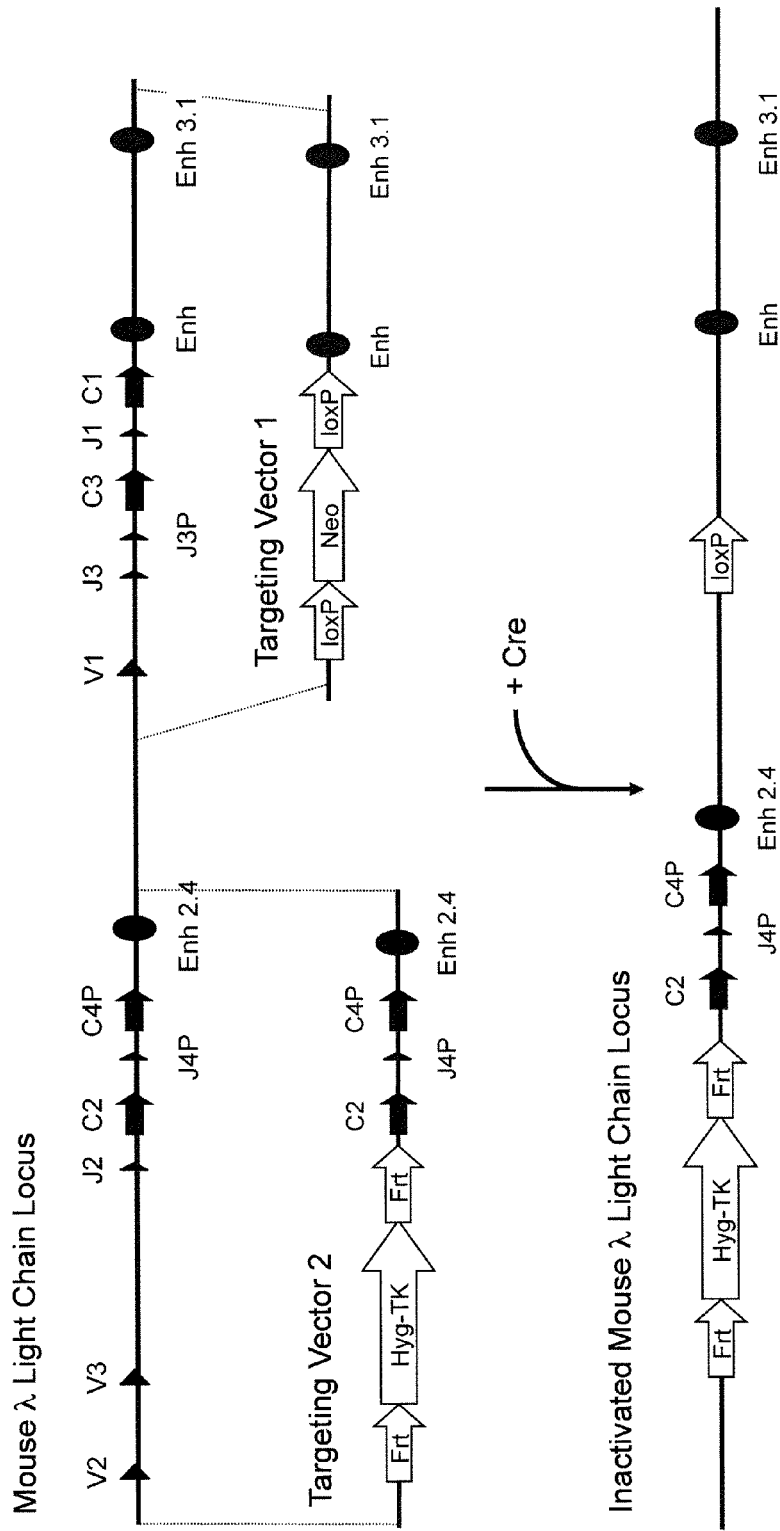
FIG. 2 shows a general illustration, not to scale, of a targeting strategy used to inactivate the endogenous mouse λ light chain locus.

In stark contrast, the mouse λ light chain locus contains only two or three (depending on the strain) mouse Vλ region gene segments (FIG. 2). At least for this reason, the severe κ bias in mice is not thought to be particularly detrimental to total antibody diversity.

According published maps of the mouse λ light chain locus, the locus consists essentially of two clusters of gene segments within a span of approximately 200 kb (FIG. 2). The two clusters contain two sets of V, J, and C genes that are capable of independent rearrangement: Vλ2-Jλ2-Cλ2-Jλ4-Cλ4 and Vλ1-Jλ3-Cλ3-Jλ1-Cλ1. Although Vλ2 has been found to recombine with all Jλ gene segments, Vλ1 appears to exclusively recombine with Cλ1. Cλ 4 is believed to be a pseudo gene with defective splice sites.

Figure 3:
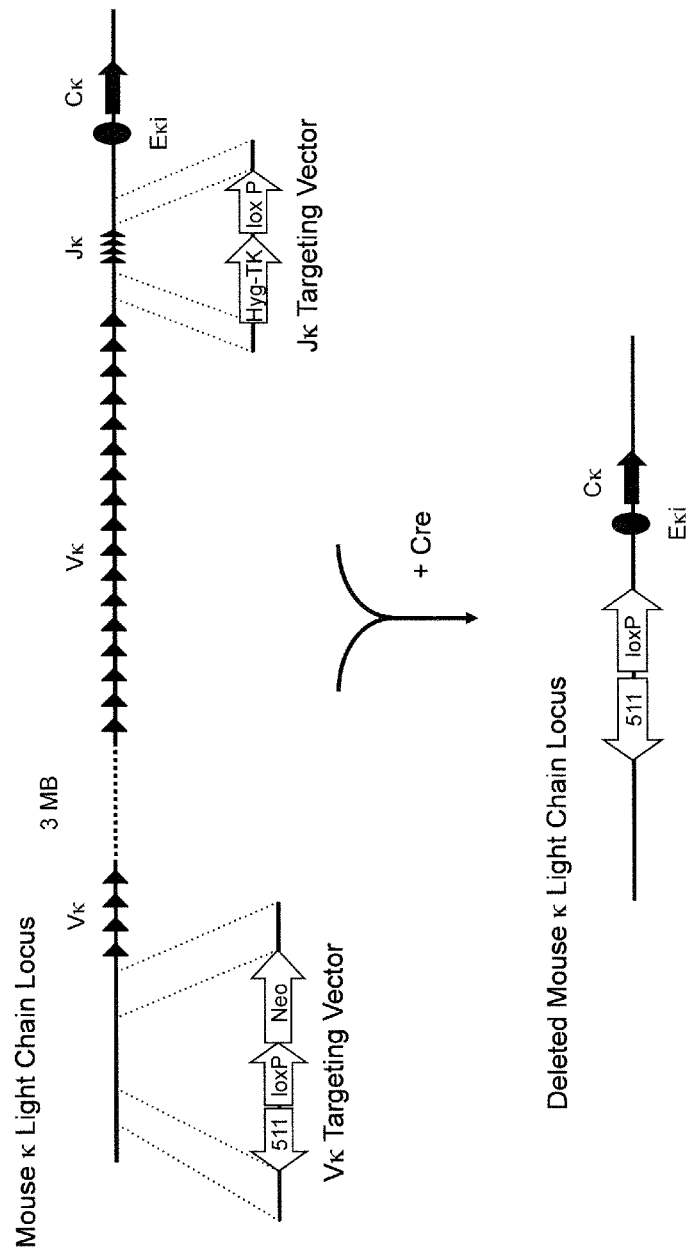
FIG. 3 shows a general illustration, not to scale, of a targeting strategy used to inactivate the endogenous mouse κ light chain locus.

The mouse κ light chain locus is strikingly different. The structure and number of gene segments that participate in the recombination events leading to a functional light chain protein from the mouse κ locus is much more complex (FIG. 3). Thus, mouse λ light chains do not greatly contribute to the diversity of an antibody population in a typical mouse.

Exploiting the rich diversity of the human λ light chain locus in mice would likely result in, among other things, a source for a more complete human repertoire of light chain V domains. Previous attempts to tap this diversity used human transgenes containing chunks of the human λ light chain locus randomly incorporated into the mouse genome (see, e.g., U.S. Pat. No. 6,998,514 and U.S. Pat. No. 7,435,871). Mice containing these randomly integrated transgenes reportedly express fully human λ light chains, however, in some cases, one or both endogenous light chain loci remain intact. This situation is not desirable as the human λ light chain sequences contend with the mouse light chain (κ or λ) in the expressed antibody repertoire of the mouse.

In contrast, the inventors describe genetically modified mice that are capable of expressing one or more λ light chain nucleic acid sequences directly from a mouse light chain locus, including by replacement at an endogenous mouse light chain locus. Genetically modified mice capable of expressing human λ light chain sequences from an endogenous locus may be further bred to mice that comprise a human heavy chain locus and thus be used to express antibodies comprising V regions (heavy and light) that are fully human. In various embodiments. The V regions express with mouse constant regions. In various embodiments, no endogenous mouse immunoglobulin gene segments are present and the V regions express with human constant regions. These antibodies would prove useful in numerous applications, both diagnostic as well as therapeutic.

Many advantages can be realized for various embodiments of expressing binding proteins derived from human Vλ and Jλ gene segments in mice. Advantages can be realized by placing human λ sequences at an endogenous light chain locus, for example, the mouse κ or λ locus. Antibodies made from such mice can have light chains that comprise human Vλ domains fused to a mouse $C_L$ region, specifically a mouse Cκ or Cλ region. The mice will also express human Vλ domains that are suitable for identification and cloning for use with human $C_L$ regions, specifically Cκ and/or Cλ regions. Because B cell development in such mice is otherwise normal, it is possible to generate compatible Vλ domains (including somatically mutated Vλ domains) in the context of either Cλ or Cκ regions.

Genetically modified mice are described that comprise an unrearranged Vλ gene segment at an immunoglobulin κ or λ light chain locus. Mice that express antibodies that comprise a light chain having a human Vλ domain fused to a Cκ and/or Cλ region are described.

Sterile Transcripts of the Immunoglobulin κ Light Chain Locus

Variations on the theme of expressing human immunoglobulin λ sequences in mice are reflected in various embodiments of genetically modified mice capable of such expression. Thus, in some embodiments, the genetically modified mice comprise certain non-coding sequence(s) from a human locus. In one embodiment, the genetically modified mouse comprises human Vλ and Jλ gene segments at an endogenous κ light chain locus, and further comprises a human κ light chain genomic fragment. In a specific embodiment, the human κ light chain genomic fragment is a non-coding sequence naturally found between a human Vκ gene segment and a human Jκ gene segment.

The human and mouse κ light chain loci contain sequences that encode sterile transcripts that lack either a start codon or an open reading frame, and that are regarded as elements that regulate transcription of the κ light chain loci. These sterile transcripts arise from an intergenic sequence located downstream or 3' of the most proximal Vκ gene segment and upstream or 5' of the κ light chain intronic enhancer (Ed) that is upstream of the κ light chain constant region gene (Cκ). The sterile transcripts arise from rearrangement of the intergenic sequence to form a VκJκ1 segment fused to a Cκ.

A replacement of the κ light chain locus upstream of the Cκ gene would remove the intergenic region encoding the sterile transcripts. Therefore, in various embodiments, a replacement of mouse κ light chain sequence upstream of the mouse Cκ gene with human λ light chain gene segments would result in a humanized mouse κ light chain locus that contains human Vλ and Jλ gene segments but not the κ light chain intergenic region that encodes the sterile transcripts.

As described herein, humanization of the endogenous mouse κ light chain locus with human λ light chain gene segments, wherein the humanization removes the intergenic region, results in a striking drop in usage of the κ light chain locus, coupled with a marked increase in λ light chain usage. Therefore, although a humanized mouse that lacks the intergenic region is useful in that it can make antibodies with human light chain variable domains (e.g., human λ or κ domains), usage from the locus decreases.

Also described is humanization of the endogenous mouse κ light chain locus with human Vλ and Jλ gene segments coupled with an insertion of a human κ intergenic region to create a Vλ locus that contains, with respect to transcription, between the final human Vλ gene segment and the first human Jλ gene segment, a κ intergenic region; which exhibits a B cell population with a higher expression than a locus that lacks the κ intergenic region. This observation is consistent with a hypothesis that the intergenic region—directly through a sterile transcript, or indirectly—suppresses usage from the endogenous λ light chain locus. Under such a hypothesis, including the intergenic region would result in a decrease in usage of the endogenous λ light chain locus, leaving the mouse a restricted choice but to employ the modified (λ into κ) locus to generate antibodies.

In various embodiments, a replacement of mouse κ light chain sequence upstream of the mouse Cκ gene with human λ light chain sequence further comprises a human κ light chain intergenic region disposed, with respect to transcription, between the 3' untranslated region of the 3' most Vλ gene segment and 5' to the first human Jλ gene segment. Alternatively, such an intergenic region may be omitted from a replaced endogenous κ light chain locus (upstream of the mouse Cκ gene) by making a deletion in the endogenous λ light chain locus. Likewise, under this embodiment, the mouse generates antibodies from an endogenous κ light chain locus containing human λ light chain sequences.

Approaches to Engineering Mice to Express Human Vλ, Domains

Various approaches to making genetically modified mice that make antibodies that contain a light chain that has a human Vλ domain fused to an endogenous $C_L$ (e.g. Cκ or Cλ) region are described. Genetic modifications are described that, in various embodiments, comprise a deletion of one or both endogenous light chain loci. For example, to eliminate mouse λ light chains from the endogenous antibody repertoire a deletion of a first Vλ-Jλ-Cλ gene cluster and replacement, in whole or in part, of the Vλ-Jλ gene segments of a second gene cluster with human Vλ-Jλ gene segments can be made. Genetically modified mouse embryos, cells, and targeting constructs for making the mice, mouse embryos, and cells are also provided.

The deletion of one endogenous Vλ-Jλ-Cλ gene cluster and replacement of the Vλ-Jλ gene segments of another endogenous Vλ-Jλ-Cλ gene cluster employs a relatively minimal disruption in natural antibody constant region association and function in the animal, in various embodiments, because endogenous Cλ genes are left intact and therefore retain normal functionality and capability to associate with the constant region of an endogenous heavy chain. Thus, in such embodiments the modification does not affect other endogenous heavy chain constant regions dependent upon functional light chain constant regions for assembly of a functional antibody molecule containing two heavy chains and two light chains. Further, in various embodiments the modification does not affect the assembly of a functional membrane-bound antibody molecule involving an endogenous heavy chain and a light chain, e.g., a hV[ domain linked to a mouse Cλ region. Because at least one functional Cλ gene is retained at the endogenous locus, animals containing a replacement of the Vλ-Jλ gene segments of an endogenous Vλ-Jλ-Cλ gene cluster with human Vλ-Jλ gene segments should be able to make normal λ light chains that are capable of binding antigen during an immune response through the human Vλ-Jλ gene segments present in the expressed antibody repertoire of the animal.

A schematic illustration (not to scale) of a deleted endogenous mouse Vλ-Jλ-Cλ gene cluster is provided in FIG. 2. As illustrated, the mouse λ light chain locus is organized into two gene clusters, both of which contain function gene segments capable of recombining to form a function mouse λ light chain. The endogenous mouse Vλ1-Jλ3-Cλ3-Jλ1-Cλ1 gene cluster is deleted by a targeting construct (Targeting Vector 1) with a neomycin cassette flanked by recombination sites. The other endogenous gene cluster (Vλ2-Vλ3-Jλ2-Cλ2-Jλ4-Cλ4) is deleted in part by a targeting construct (Targeting Vector 2) with a hygromycin-thymidine kinase cassette flanked by recombination sites. In this second targeting event, the Cλ2-Jλ4-Cλ 4 endogenous gene segments are retained. The second targeting construct (Targeting Vector 2) is constructed using recombination sites that are different than those in the first targeting construct (Targeting Vector 1) thereby allowing for the selective deletion of the selection cassette after a successful targeting has been achieved. The resulting double-targeted locus is functionally silenced in that no endogenous λ light chain can be produced. This modified locus can be used for the insertion of human Vλ and Jλ gene segments to create an endogenous mouse λ locus comprising human Vλ and Jλ gene segments, whereby, upon recombination at the modified locus, the animal produces λ light chains comprising rearranged human Vλ and Jλ gene segments linked to an endogenous mouse Cλ gene segment.

Genetically modifying a mouse to render endogenous λ gene segments nonfunctional, in various embodiments, results in a mouse that exhibits exclusively κ light chains in its antibody repertoire, making the mouse useful for evaluating the role of λ light chains in the immune response, and useful for making an antibody repertoire comprising Vκ domains but not Vλ domains.

A genetically modified mouse that expresses a hVλ linked to a mouse Cλ gene having been recombined at the endogenous mouse λ light chain locus can be made by any method known in the art. A schematic illustration (not to scale) of the replacement of the endogenous mouse Vλ2-Vλ3-Jλ2 gene segments with human Vλ and Jλ gene segments is provided in FIG. 4A. As illustrated, an endogenous mouse λ light chain locus that had been rendered nonfunctional is replaced by a targeting construct (12/1-λ. Targeting Vector) that includes a neomycin cassette flanked by recombination sites. The Vλ2-Vλ3-Jλ2 gene segments are replaced with a genomic fragment containing human λ sequence that includes 12 hVλ gene segments and a single hJλ gene segment.

Figure 4A:
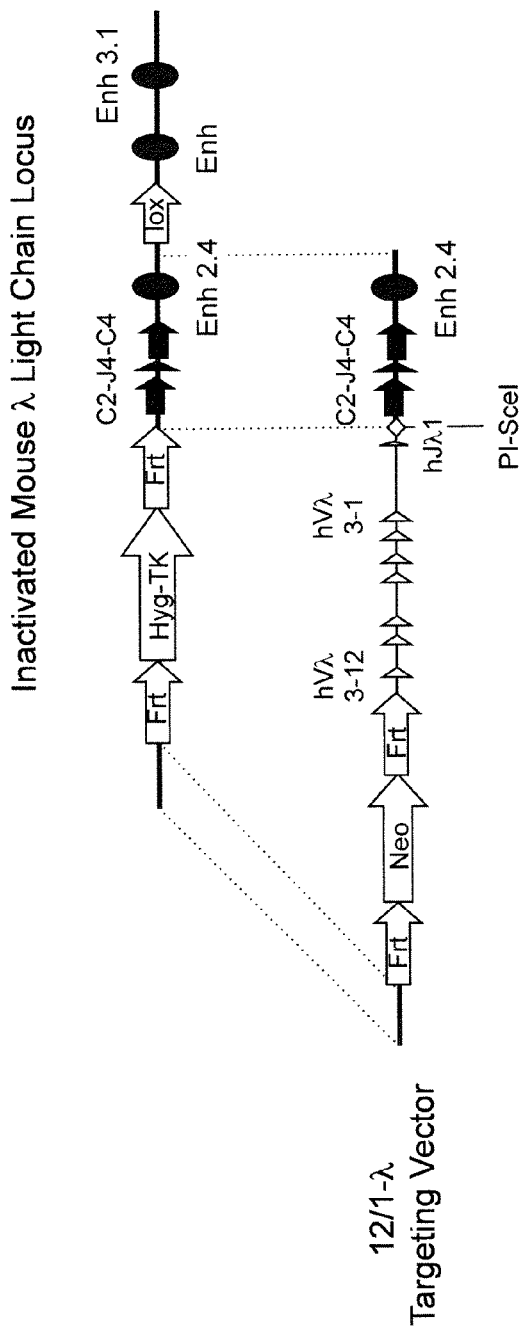
FIG. 4A shows a general illustration, not to scale of an initial targeting vector for targeting the endogenous mouse λ light chain locus with human λ light chain sequences including 12 hVλ gene segments and hJλ1 gene segment (12/1λ Targeting Vector).

Thus, this first approach positions one or more hVλ gene segments at the endogenous λ light chain locus contiguous with a single hJλ gene segment (FIG. 4A).

Further modifications to the modified endogenous λ light chain locus can be achieved with using similar techniques to insert more hVλ gene segments. For example, schematic illustrations of two additional targeting constructs (+16-λ and +12-λ. Targeting Vectors) used for progressive insertion of addition human hVλ gene segments are provided in FIG. 5A. As illustrated, additional genomic fragments containing specific human hVλ gene segments are inserted into the modified endogenous λ light chain locus in successive steps using homology provided by the previous insertion of human λ light chain sequences. Upon recombination with each targeting construct illustrated, in sequential fashion, 28 additional hVλ gene segments are inserted into the modified endogenous λ light chain locus. This creates a chimeric locus that produces a λ light chain protein that comprises human Vλ-Jλ gene segments linked to a mouse Cλ gene.

Figure 5A:
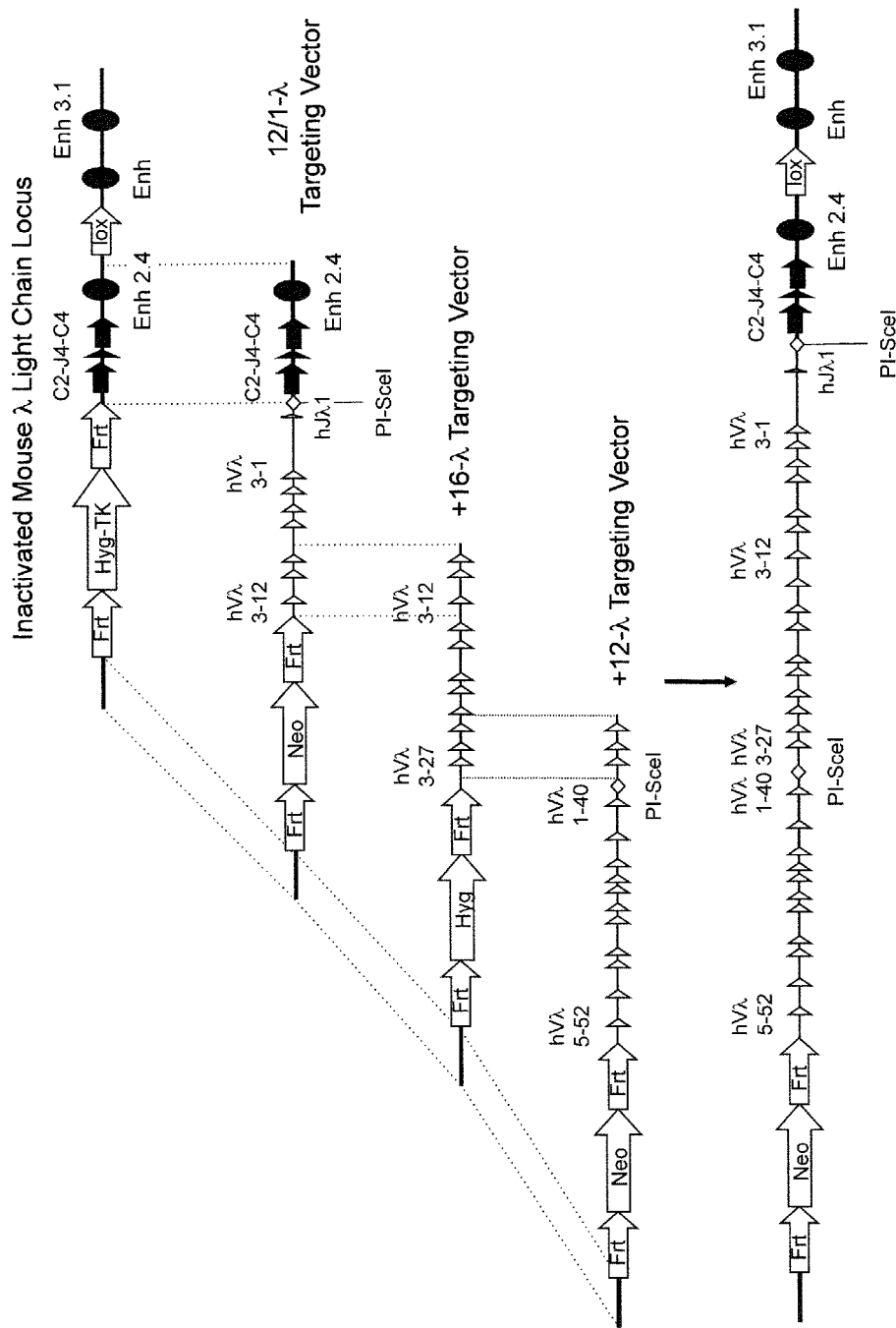
FIG. 5A shows a general illustration, not to scale, of a targeting strategy for progressive insertion of 40 hVλ gene segments and a single hJλ gene segment into the mouse λ light chain locus.
Figure 7A:
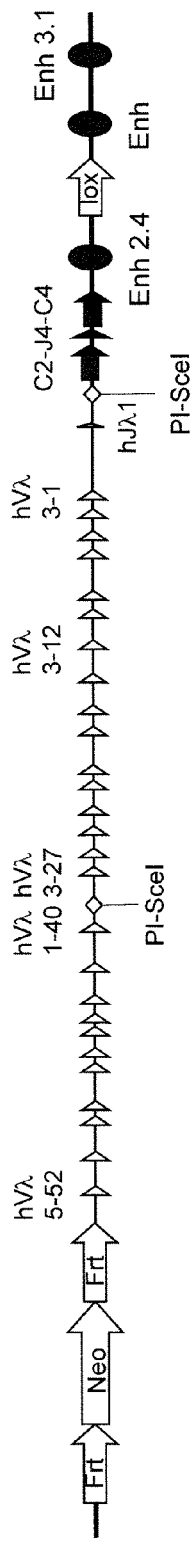
FIG. 7A shows a general illustration, not to scale, of the locus structure for a modified mouse λ light chain locus containing 40 hVλ gene segments and a single hJλ gene segment operably linked to the endogenous Cλ2 gene.

The above approaches to insert human λ light chain gene segments at the mouse λ locus, maintains the enhancers positioned downstream of the Cλ2-Jλ4-Cλ4 gene segments (designated Enh 2.4, Enh and Enh 3.1 FIG. 4A and FIG. 5A). This approach results in a single modified allele at the endogenous mouse λ light chain locus (FIG. 7A).

Compositions and methods for making a mouse that expresses a light chain comprising hVλ and Jλ gene segments operably linked to a mouse Cλ gene segment, are provided, including compositions and method for making a mouse that expresses such genes from an endogenous mouse λ light chain locus. The methods include selectively rendering one endogenous mouse Vλ-Jλ-Cλ gene cluster nonfunctional (e.g., by a targeted deletion), and employing a hVλ and Jλ gene segments at the endogenous mouse λ light chain locus to express a hVλ domain in a mouse.

Alternatively, in a second approach, human λ light chain gene segments may be positioned at the endogenous κ light chain locus. The genetic modification, in various embodiments, comprises a deletion of the endogenous κ light chain locus. For example, to eliminate mouse κ light chains from the endogenous antibody repertoire a deletion of the mouse Vκ and Jκ gene segments can be made. Genetically modified mouse embryos, cells, and targeting constructs for making the mice, mouse embryos, and cells are also provided.

For the reasons stated above, the deletion of the mouse Vκ and Jκ gene segments employs a relatively minimal disruption. A schematic illustration (not to scale) of deleted mouse Vκ and Jκ gene segments is provided in FIG. 3. The endogenous mouse Vκ and Jκ gene segments are deleted via recombinase-mediated deletion of mouse sequences position between two precisely positioned targeting vectors each employing site-specific recombination sites. A first targeting vector (Jκ Targeting Vector) is employed in a first targeting event to delete the mouse Jκ gene segments. A second targeting vector (Vκ Targeting Vector) is employed in a second, sequential targeting event to delete a sequence located 5' of the most distal mouse Vκ gene segment. Both targeting vectors contain site-specific recombination sites thereby allowing for the selective deletion of both selection cassettes and all intervening mouse κ light chain sequences after a successful targeting has been achieved. The resulting deleted locus is functionally silenced in that no endogenous κ light chain can be produced. This modified locus can be used for the insertion of hVλ and Jλ gene segments to create an endogenous mouse κ locus comprising hVλ and Jλ gene segments, whereby, upon recombination at the modified locus, the animal produces λ light chains comprising rearranged hVλ and Jλ gene segments operably linked to an endogenous mouse Cκ gene segment. Various targeting vectors comprising human λ light chain sequences can be used in conjunction with this deleted mouse κ locus to create a hybrid light chain locus containing human λ gene segments operably linked with a mouse Cκ region.

Figure 4B:
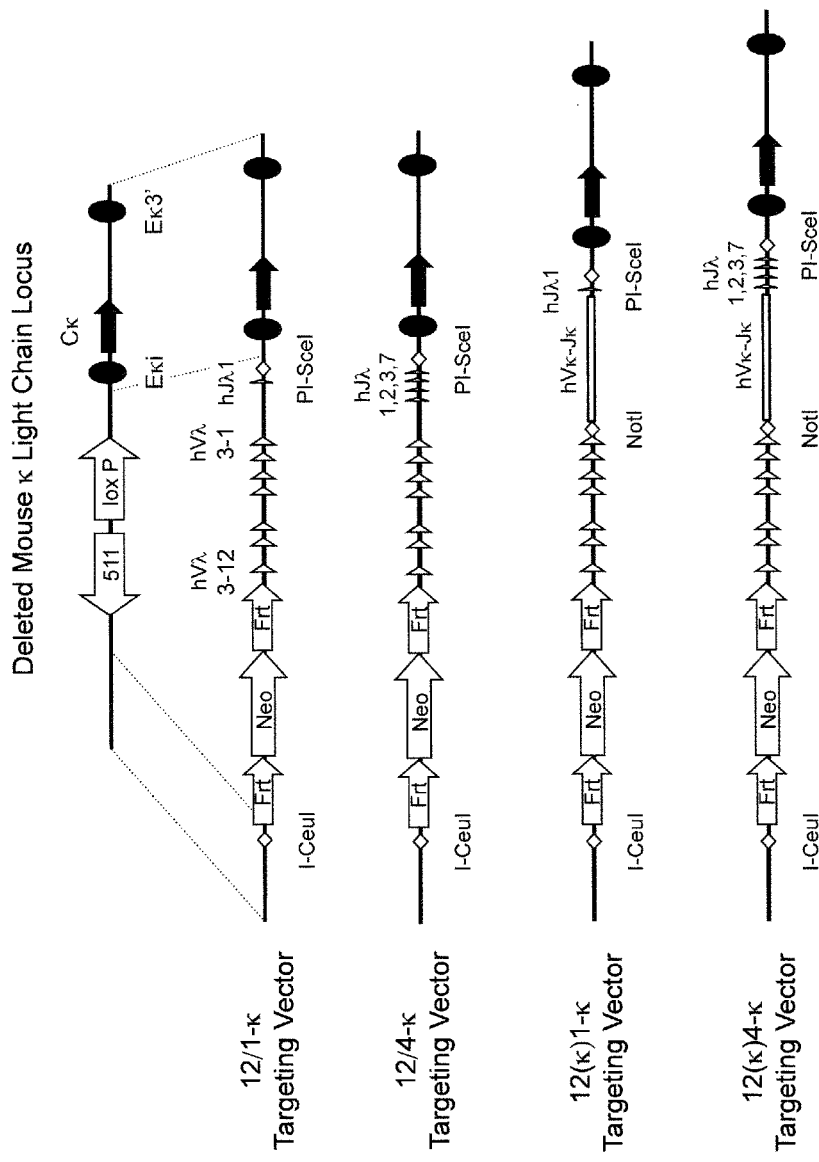
FIG. 4B shows a general illustration, not to scale, of four initial targeting vectors for targeting the endogenous mouse κ light chain locus with human λ light chain sequences including 12 hVλ gene segments and hJλ1 gene segment (12/1-κ Targeting Vector), 12 hVλ gene segments and hJλ1, 2, 3 and 7 gene segments (12/4-κ Targeting Vector), 12 hVλ gene segments, a human Vκ-Jκ genomic sequence and hJλ1 gene segment (12(κ)1-κ Targeting Vector) and 12 hVλ gene segments, a human Vκ-Jκ genomic sequence and hJλ1, 2, 3 and 7 gene segments (12(κ)4-κ Targeting Vector).

Thus, a second approach positions one or more human Vλ gene segments are positioned at the mouse κ light chain locus contiguous with a single human Jλ gene segment (12/1-κ Targeting Vector, FIG. 4B).

In various embodiments, modifications to this approach can be made to add gene segments and/or regulatory sequences to optimize the usage of the human λ light chain sequences from the mouse κ locus within the mouse antibody repertoire.

In a third approach, one or more hVλ gene segments are positioned at the mouse κ light chain locus contiguous with four hJλ gene sequences (12/4-κ Targeting Vector FIG. 4B).

In a third approach, one or more hVλ gene segments are positioned at the mouse κ light chain locus contiguous with a human κ intergenic sequence and a single hJλ gene sequence (12(κ)1-κ Targeting Vector, FIG. 4B).

In a fourth approach, one or more hVλ gene segments are positioned at the mouse κ light chain locus contiguous with a human κ intergenic sequence four hJλ gene sequences (12(κ) 4-κ Targeting Vector FIG. 4B).

Figure 5B:
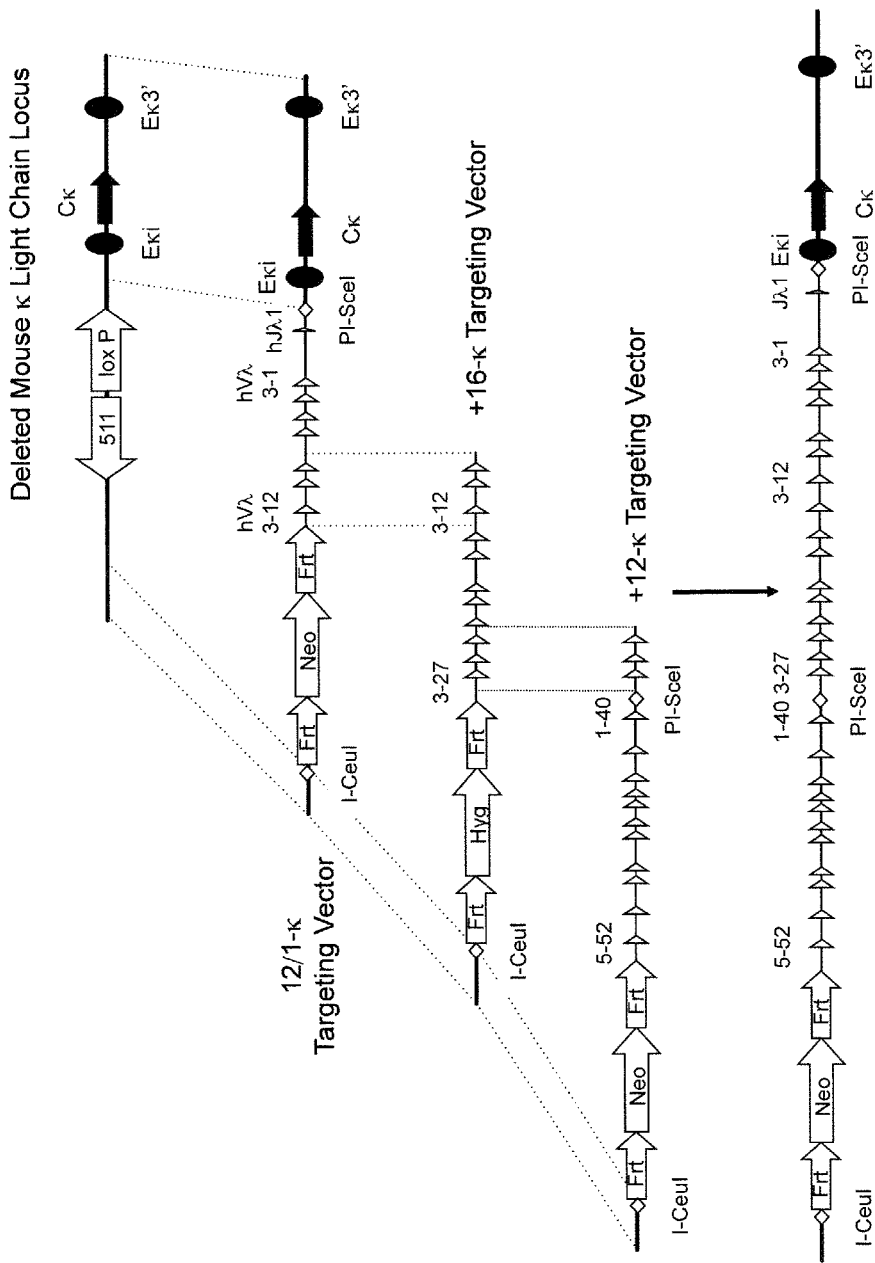
FIG. 5B shows a general illustration, not to scale, of a targeting strategy for progressive insertion of 40 hVλ gene segments and a single hJλ gene segment into the mouse κ locus.
Figure 7B:
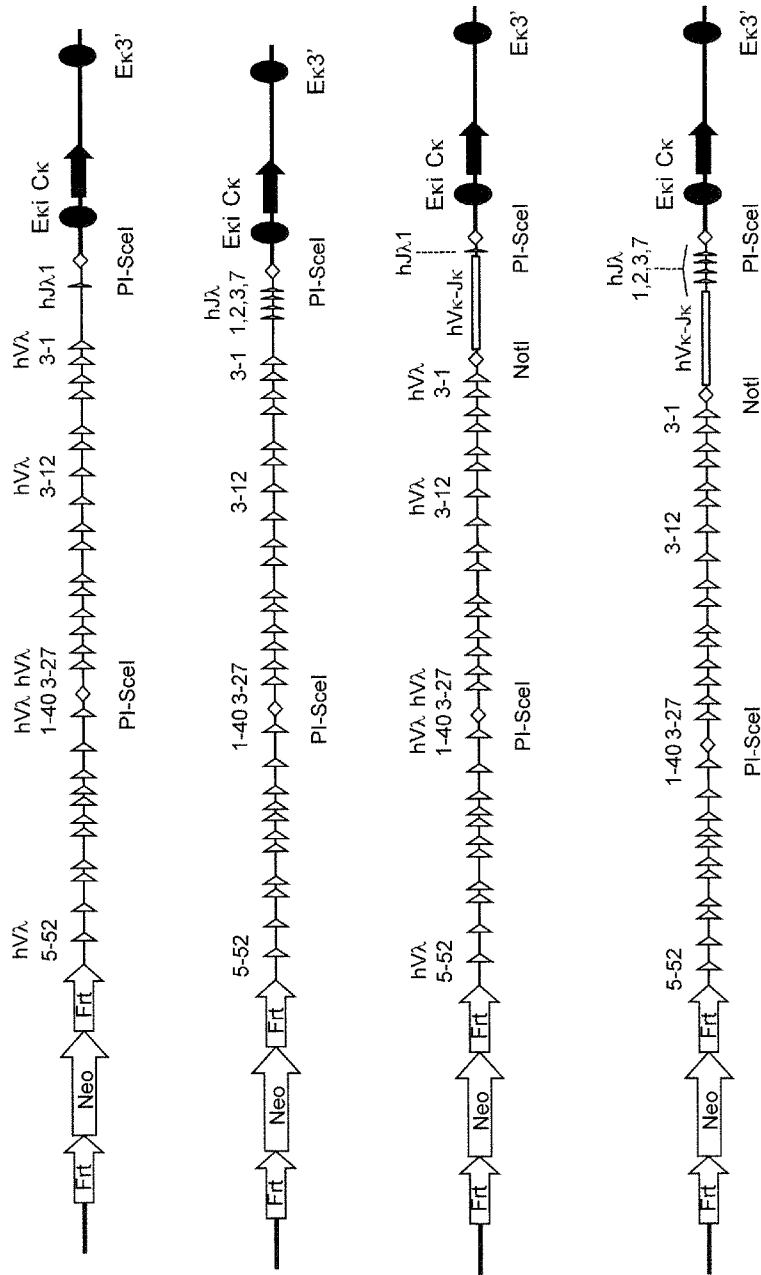
FIG. 7B shows a general illustration, not to scale, of the locus structure for four independent, modified mouse κ light chain loci containing 40 hVλ gene segments and either one or four hJλ gene segments with or without a contiguous human Vκ-Jκ genomic sequence operably linked to the endogenous Cκ gene.

All of the above approaches to insert human λ light chain gene segments at the mouse κ locus, maintain the κ intronic enhancer element upstream of the Cκ gene (designated Eκi, FIG. 4B and FIG. 5B) and the 3' κ enhancer downstream of the Cκ gene (designated Eκ3', FIG. 4B and FIG. 5B). The approaches result in four separate modified alleles at the endogenous mouse κ light chain locus (FIG. 7B).

In various embodiments, genetically modified mouse comprise a knockout of the endogenous mouse λ light chain locus. In one embodiment, the λ light chain locus is knocked out by a strategy that deletes the region spanning Vλ2 to Jλ2, and the region spanning Vλ1 to Cλ1 (FIG. 2). Any strategy that reduces or eliminates the ability of the endogenous λ light chain locus to express endogenous λ domains is suitable for use with embodiments in this disclosure.

Lambda Domain Antibodies from Genetically Modified Mice

Mice comprising human λ sequences at either the mouse κ or λ light chain locus will express a light chain that comprises a hVλ region fused to a mouse $C_L$ (Cκ or Cλ) region. These are advantageously bred to mice that (a) comprise a functionally silenced light chain locus (e.g., a knockout of the endogenous mouse κ or λ light chain locus); (b) comprise an endogenous mouse λ light chain locus that comprises hV and hJ gene segments operably linked to an endogenous mouse Cλ gene; (c) comprise an endogenous mouse κ light chain locus that comprises hVκ and hJκ gene segments operably linked to an endogenous mouse Cκ gene; and, (d) a mouse in which one κ allele comprises hVκs and hJκs; the other κ allele comprising hVλs and hJλs; one λ allele comprising hVλs and hJλs and one λ allele silenced or knocked out, or both λ alleles comprising hVλs and hJλs; and, two heavy chain alleles that each comprise $hV_Hs$, $hD_Hs$, and $hJ_Hs$.

The antibodies that comprise the hVλ domains expressed in the context of either Cκ or Cλ are used to make fully human antibodies by cloning the nucleic acids encoding the hVλ domains into expression constructs that bear genes encoding human Cλ. Resulting expression constructs are transfected into suitable host cells for expressing antibodies that display a fully hVλ domain fused to hCλ.

EXAMPLES

The following examples are provided so as to describe how to make and use methods and compositions of the invention, and are not intended to limit the scope of what the inventors regard as their invention. Unless indicated otherwise, temperature is indicated in Celsius, and pressure is at or near atmospheric.

Example I

Deletion of the Mouse Immunoglobulin Light Chain Loci

Various targeting constructs were made using VELOCIGENE® technology (see, e.g., U.S. Pat. No. 6,586,251 and Valenzuela et al. (2003) High-throughput engineering of the mouse genome coupled with high-resolution expression analysis, *Nature Biotech.* 21(6):652-659) to modify mouse genomic Bacterial Artificial Chromosome (BAC) libraries to inactivate the mouse κ and λ light chain loci.

Deletion of the Mouse λ Light Chain Locus.

DNA from mouse BAC clone RP23-135k15 (Invitrogen) was modified by homologous recombination to inactivate the endogenous mouse λ light chain locus through targeted deletion of the Vλ-Jλ-Cλ gene clusters (FIG. 2).

Briefly, the entire proximal cluster comprising Vλ1-Jλ3-Cλ3-Jλ1-Cλ1 gene segments was deleted in a single targeting event using a targeting vector comprising a neomycin cassette flanked by loxP sites with a 5' mouse homology arm containing sequence 5' of the Vλ1 gene segment and a 3' mouse homology arm containing sequence 3' of the Cλ1 gene segment (FIG. 2, Targeting Vector 1).

A second targeting construct was prepared to precisely delete the distal endogenous mouse λ gene cluster containing Vλ2-Jλ2-Cλ2-Jλ4-Cλ4 except that the targeting construct contained a 5' mouse homology arm that contained sequence 5' of the Vλ2 gene segment and a 3' mouse homology arm that contained sequence 5' to the endogenous Cλ2 gene segment (FIG. 2, Targeting Vector 2). Thus, the second targeting construct precisely deleted Vλ2-Jλ2, while leaving Cλ2-Jλ4-Cλ4 intact at the endogenous mouse λ locus. ES cells containing an inactivated endogenous λ locus (as described above) were confirmed by karyotyping and screening methods (e.g., TAQ-MAN®) known in the art. DNA was then isolated from the modified ES cells and subjected to treatment with CRE recombinase thereby mediating the deletion of the proximal targeting cassette containing the neomycin marker gene, leaving only a single loxP site at the deletion point (FIG. 2, bottom).

Deletion of the Mouse κ Light Chain Locus.

Several targeting constructs were made using similar methods described above to modify DNA from mouse BAC clones RP23-302g12 and RP23-254m04 (Invitrogen) by homologous recombination to inactivate the mouse κ light chain locus in a two-step process (FIG. 3).

Briefly, the Jκ gene segments (1-5) of the endogenous mouse κ light chain locus were deleted in a single targeting event using a targeting vector comprising a hygromycin-thymidine kinase (hyg-TK) cassette containing a single loxP site 3' to the hyg-TK cassette (FIG. 3, Jκ Targeting Vector). The homology arms used to make this targeting vector contained mouse genomic sequence 5' and 3' of the endogenous mouse Jκ gene segments. In a second targeting event, a second targeting vector was prepared to delete a portion of mouse genomic sequence upstream (5') to the most distal endogenous mouse Vκ gene segment (FIG. 3, Vκ Targeting Vector). This targeting vector contained an inverted lox511 site, a loxP site and a neomycin cassette. The homology arms used to make this targeting vector contained mouse genomic sequence upstream of the most distal mouse Vκ gene segment. The targeting vectors were used in a sequential fashion (i.e., Jκ then Vκ) to target DNA in ES cells. ES bearing a double-targeted chromosome (i.e., a single endogenous mouse κ locus targeted with both targeting vectors) were confirmed by karyotyping and screening methods (e.g., Taqman™) known in the art. DNA was then isolated from the modified ES cells and subjected to treatment with Cre recombinase thereby mediating the deletion of endogenous mouse Vκ gene segments and both selection cassettes, while leaving two juxtaposed lox sites in opposite orientation relative to one another (FIG. 3, bottom; SEQ ID NO:1).

Thus, two modified endogenous light chain loci (κ and λ) containing intact enhancer and constant regions were created for progressively inserting unrearranged human λ germline gene segments in a precise manner using targeting vectors described below.

Example II

Replacement of Mouse Light Chain Loci with a Human λ, Light Chain Mini-Locus

Multiple targeting vectors were engineered for progressive insertion of human λ gene segments into the endogenous mouse κ and λ light chain loci using similar methods as described above. Multiple independent initial modifications were made to the endogenous light chain loci each producing a chimeric light chain locus containing hVλ and Jλ gene segments operably linked to mouse light chain constant genes and enhancers.

A Human λ, Mini-Locus Containing 12 Human Vλ, and One Human Jλ, Gene Segment.

A series of initial targeting vectors were engineered to contain the first 12 consecutive human Vλ gene segments from cluster A and a hJλ1 gene segment or four hJλ gene segments using a human BAC clone named RP11-729g4 (Invitrogen). FIGS. 4A and 4B show the targeting vectors that were constructed for making an initial insertion of human λ light chain gene segments at the mouse λ and κ light chain loci, respectively.

For a first set of initial targeting vectors, a 124,125 bp DNA fragment from the 729g4 BAC clone containing 12 hVλ gene segments and a hJλ1 gene segment was engineered to contain a PI-SceI site 996 bp downstream (3') of the hJλ1 gene segment for ligation of a 3' mouse homology arm. Two different sets of homology arms were used for ligation to this human fragment; one set of homology arms contained endogenous mouse λ sequences from the 135k15 BAC clone (FIG. 4A) and another set contained endogenous κ sequence 5' and 3' of the mouse Vκ and Jκ gene segments from mouse BAC clones RP23-302g12 and RP23-254m04, respectively (FIG. 4B).

For the 12/1-λ. Targeting Vector (FIG. 4A), a PI-SceI site was engineered at the 5' end of a 27,847 bp DNA fragment containing the mouse Cλ2-Jλ4-Cλ4 and enhancer 2.4 of the modified mouse λ locus described in Example 1. The ~28 kb mouse fragment was used as a 3' homology arm by ligation to the ~124 kb human λ fragment, which created a 3' junction containing, from 5' to 3', a hJλ1 gene segment, 996 bp of human λ sequence 3' of the hJλ1 gene segment, 1229 bp of mouse λ sequence 5' to the mouse Cλ2 gene, the mouse Cλ2 gene and the remaining portion of the ~28 kb mouse fragment. Upstream (5') from the human Vλ3-12 gene segment was an additional 1456 bp of human λ sequence before the start of the 5' mouse homology arm, which contained 23,792 bp of mouse genomic DNA corresponding to sequence 5' of the endogenous mouse λ locus. Between the 5' homology arm and the beginning of the human λ sequence was a neomycin cassette flanked by Frt sites.

Thus, the 12/1-λ. Targeting Vector included, from 5' to 3', a 5' homology arm containing ~24 kb of mouse λ genomic sequence 5' of the endogenous λ locus, a 5' Frt site, a neomycin cassette, a 3' Frt site, ~123 kb of human genomic λ sequence containing the first 12 consecutive hVλ gene segments and a hJλ1 gene segment, a PI-SceI site, and a 3' homology arm containing ~28 kb of mouse genomic sequence including the endogenous Cλ2-Jλ4-Cλ4 gene segments, the mouse enhancer 2.4 sequence and additional mouse genomic sequence downstream (3') of the enhancer 2.4 (FIG. 4A).

In a similar fashion, the 12/1-κ Targeting Vector (FIG. 4B) employed the same ~124 human λ fragment with the exception that mouse homology arms containing mouse κ sequence were used such that targeting to the endogenous κ locus could be achieved by homologous recombination. Thus, the 12/1-κ Targeting Vector included, from 5' to 3', a 5' homology arm containing ~23 kb of mouse genomic sequence 5' of the endogenous κ locus, an I-CeuI site, a 5' Frt site, a neomycin cassette, a 3' Frt site, 124 kb of human genomic λ sequence containing the first 12 consecutive hVλ gene segments and a hJλ1 gene segment, a PI-SceI site, and a 3' homology arm containing ~28 kb of mouse genomic sequence including the endogenous the mouse Cκ gene, Eκi and Eκ3' and additional mouse genomic sequence downstream (3') of Eκ3' (FIG. 4B, 12/1-κ Targeting Vector).

Homologous recombination with either of these two initial targeting vectors created a modified mouse light chain locus (κ or λ) containing 12 hVλ gene segments and a hJλ1 gene segment operably linked to the endogenous mouse light chain constant gene and enhancers (Cκ or Cλ2 and Eκi/Eκ3' or Enh 2.4/Enh 3.1) gene which, upon recombination, leads to the formation of a chimeric λ light chain.

A Human λ, Mini-Locus with 12 Human Vλ, and Four Human Jλ, Gene Segments.

In another approach to add diversity to a chimeric λ light chain locus, a third initial targeting vector was engineered to insert the first 12 consecutive human Vλ gene segments from cluster A and hJλ1, 2, 3 and 7 gene segments into the mouse κ light chain locus (FIG. 4B, 12/4-κ Targeting Vector). A DNA segment containing hJλ1, Jλ2, Jλ 3 and Jλ 7 gene segments was made by de novo DNA synthesis (Integrated DNA Technologies) including each Jλ gene segment and human genomic sequence of ~100 bp from both the immediate 5' and 3' regions of each Jλ gene segment. A PI-SceI site was engineered into the 3' end of this ~1 kb DNA fragment and ligated to a chloroamphenicol cassette. Homology arms were PCR amplified from human λ sequence at 5' and 3' positions relative to the hJλ1 gene segment of the human BAC clone 729g4. Homologous recombination with this intermediate targeting vector was performed on a modified 729g4 BAC clone that had been previously targeted upstream (5') of the human Vλ3-12 gene segment with a neomycin cassette flanked by Frt sites, which also contained an I-CeuI site 5' to the 5' Frt site. The double-targeted 729g4 BAC clone included from 5' to 3' an I-CeuI site, a 5' Frt site, a neomycin cassette, a 3' Frt site, a ~123 kb fragment containing the first 12 hVλ gene segments, a ~1 kb fragment containing human Jλ1, 2, 3 and 7 gene segments, a PI-SceI site, and a chloroamphenicol cassette. This intermediate targeting vector was digested together with I-CeuI and PI-SceI and subsequently ligated into the modified mouse BAC clone (described above) to create the third targeting vector.

This ligation resulted in a third targeting vector for insertion of human λ sequences into the endogenous κ light chain locus, which included, from 5' to 3', a 5' mouse homology arm containing ~23 kb of genomic sequence 5' of the endogenous mouse κ locus, an I-CeuI site, a 5' Frt site, a neomycin cassette, a 3' Frt site, a ~123 kb fragment containing the first 12 hVλ gene segments, a ~1 kb fragment containing hJλ1, 2, 3 and 7 gene segments, a PI-SceI site and a 3' homology arm containing ~28 kb of mouse genomic sequence including the endogenous the mouse Cκ gene, Eκi and Eκ3' and additional mouse genomic sequence downstream (3') of Eκ3' (FIG. 4B, 12/4-κ Targeting Vector). Homologous recombination with this third targeting vector created a modified mouse κ light chain locus containing 12 hVλ gene segments and four hJλ gene segments operably linked to the endogenous mouse Cκ gene which, upon recombination, leads to the formation of a chimeric human λ/mouse κ light chain.

A Human λ, Mini-Locus with an Integrated Human κ Light Chain Sequence.

In a similar fashion, two additional targeting vectors similar to those engineered to make an initial insertion of human λ gene segments into the endogenous κ light chain locus (FIG. 4B, 12/1-κ and 12/4-κ Targeting Vectors) were engineered to progressively insert human λ light chain gene segments using uniquely constructed targeting vectors containing contiguous human λ and κ genomic sequences. These targeting vectors were constructed to include a ~23 kb human κ genomic sequence naturally located between human Vκ4-1 and Jκ1 gene segments. This human κ genomic sequence was specifically positioned in these two additional targeting vectors between human Vλ and human Jλ gene segments (FIG. 4B, 12(κ)1-κ and 12(κ)4-κ Targeting Vectors).

Figure 6:
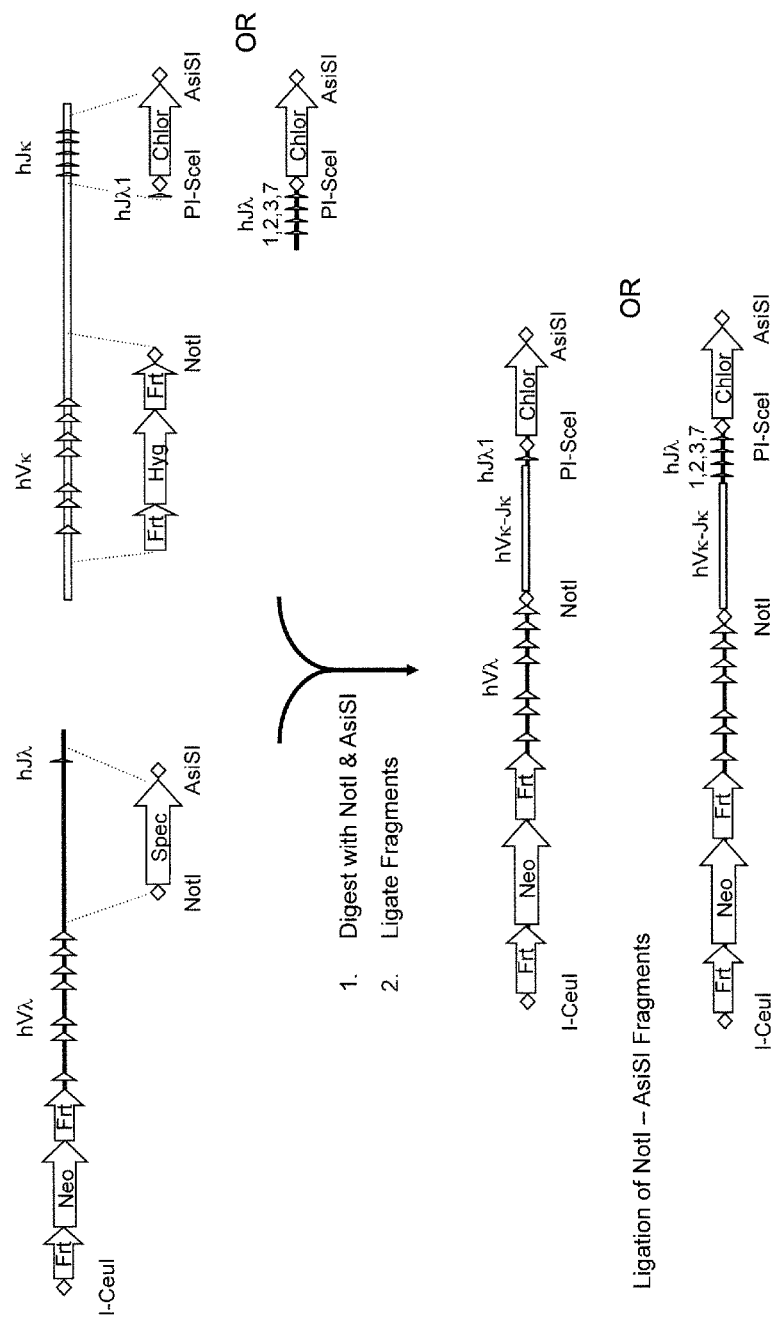
FIG. 6 show a general illustration, not to scale, of the targeting and molecular engineering steps employed to make unique human λ-κ hybrid targeting vectors for construction of a hybrid light chain locus containing a human κ intergenic sequence, multiple hJλ gene segments or both.

Both targeting vectors containing the human κ genomic sequence were made using the modified RP11-729g4 BAC clone described above (FIG. 6). This modified BAC clone was targeted with a spectinomycin selection cassette flanked by NotI and AsiSI restriction sites (FIG. 6, top left). Homologous recombination with the spectinomycin cassette resulted in a double-targeted 729g4 BAC clone which included, from 5' to 3', an I-CeuI site, a 5' Frt site, a neomycin cassette, a 3' Frt site, a ~123 kb fragment containing the first 12 hVλ gene segments, a NotI site about 200 bp downstream (3') to the nonamer sequence of the hVλ3-1 gene segment, a spectinomycin cassette and an AsiSI site. A separate human BAC clone containing human κ sequence (CTD-2366j12) was targeted two independent times to engineer restriction sites at locations between hVκ4-1 and hJκ1 gene segments to allow for subsequent cloning of a ~23 kb fragment for ligation with the hVλ gene segments contained in the double targeted modified 729g4 BAC clone (FIG. 6, top right).

Briefly, the 2366j12 BAC clone is about 132 kb in size and contains hVκ gene segments 1-6, 1-5, 2-4, 7-3, 5-2, 4-1, human κ genomic sequence down stream of the Vκ gene segments, hJκ gene segments 1-5, the hCκ and about 20 kb of additional genomic sequence of the human κ locus. This clone was first targeted with a targeting vector containing a hygromycin cassette flanked by Frt sites and a NotI site downstream (3') of the 3' Frt site. The homology arms for this targeting vector contained human genomic sequence 5' and 3' of the Vκ gene segments within the BAC clone such that upon homologous recombination with this targeting vector, the Vκ gene segments were deleted and a NotI site was engineered ~133 bp downstream of the hVκ4-1 gene segment (FIG. 6, top right). This modified 2366j12 BAC clone was targeted independently with two targeting vectors at the 3' end to delete the hJκ gene segments with a chloroamphenicol cassette that also contained either a hJλ1 gene segment, a PI-SceI site and an AsiSI site or a human λ genomic fragment containing four hJλ gene segments (supra), a PI-SceI site and an AsiSI site (FIG. 6, top right). The homology arms for these two similar targeting vectors contained sequence 5' and 3' of the hJκ gene segments. Homologous recombination with these second targeting vectors and the modified 2366j12 BAC clone yielded a double-targeted 2366j12 clone which included, from 5' to 3', a 5' Frt site, a hygromycin cassette, a 3' Frt site, a NotI site, a 22,800 bp genomic fragment of the human κ locus containing the intergenic region between the Vκ4-1 and Jκ1 gene segments, either a hJλ1 gene segment or a human λ genomic fragment containing hJλ1, Jλ2, Jλ 3 and Jλ7, a PI-SceI site and a chloroamphenicol cassette (FIG. 6, top right). Two final targeting vectors to make the two additional modifications were achieved by two ligation steps using the double-targeted 729g4 and 2366j12 clones.

Double targeted 729g4 and 2366j12 clones were digested with NotI and AsiSI yielding one fragment containing the neomycin cassette and hVλ gene segments and another fragment containing the ~23 kb genomic fragment of the human κ locus containing the intergenic region between the Vκ4-1 and Jκ1 gene segments, either a hJλ1 gene segment or a genomic fragment containing hJλ1, Jλ2, Jλ 3 and Jλ 7 gene segments, the PI-SceI site and the chloroamphenicol cassette, respectively. Ligation of these fragments generated two unique BAC clones containing from 5' to 3' the hVλ gene segments, the human κ genomic sequence between the Vκ4-1 and Jκ1 gene segments, either a hJλ1 gene segment or a genomic fragment containing hJλ1, Jλ2, Jλ 3 and Jλ 7 gene segments, a PI-SceI site and a chloroamphenicol cassette (FIG. 6, bottom). These new BAC clones were then digested with I-CeuI and PI-SceI to release the unique fragments containing the upstream neomycin cassette and the contiguous human λ and κ sequences and ligated into a modified mouse BAC clone 302g12 which contained from 5' to 3' mouse genomic sequence 5' of the endogenous κ locus, an I-CeuI site, a 5' Frt site, a neomycin cassette, a 3' Frt site, hVλ gene segments (3-12 to 3-1), a NotI site 200 bp downstream of Vλ3-1, 23 kb of human κ sequence naturally found between the human Vκ4-1 and Jκ1 gene segments, either a hJλ1 gene segment or a genomic fragment containing hJλ1, Jλ2, Jλ 3 and Jλ 7 gene segments, the mouse Eκi, the mouse Cκ gene and Eκ3' (FIG. 4, 12hVλ-VκJκ-hJλ1 and 12hVλ-VκJκ-4hJλ Targeting Vectors). Homologous recombination with both of these targeting vectors created two separate modified mouse κ light chain loci containing 12 hVλ gene segments, human κ genomic sequence, and either one or four hJλ gene segments operably linked to the endogenous mouse Cκ gene which, upon recombination, leads to the formation of a chimeric human λ/mouse κ light chain.

Example III

Engineering Additional Human Vλ, Genes Segments into a Human λ, Light Chain Mini-Locus Additional hVλ gene segments were added independently to each of the initial modifications described in Example λ using similar targeting vectors and methods (FIG. 5A, +16-λ. Targeting Vector and FIG. 5B, +16-κ Targeting Vector).

Introduction of 16 Additional Human Vλ Gene Segments.

Upstream (5') homology arms used in constructing targeting vectors for adding 16 additional hVλ gene segments to the modified light chain loci described in Example λ contained mouse genomic sequence 5' of either the endogenous κ or λ light chain loci. The 3' homology arms were the same for all targeting vectors and contained human genomic sequence overlapping with the 5' end of the human λ sequence of the modifications as described in Example 2.

Briefly, two targeting vectors were engineered for introduction of 16 additional hVλ gene segments to the modified mouse light chain loci described in Example λ (FIGS. 5A and 5B, +16-λ or +16-κ Targeting Vector). A ~172 kb DNA fragment from human BAC clone RP11-761I13 (Invitrogen) containing 21 consecutive hVλ gene segments from cluster A was engineered with a 5' homology arm containing mouse genomic sequence 5' to either the endogenous κ or λ light chain loci and a 3' homology arm containing human genomic λ sequence. The 5' mouse κ or λ homology arms used in these targeting constructs were the same 5' homology arms described in Example λ (FIGS. 5A and 5B). The 3' homology arm included a 53,057 bp overlap of human genomic λ sequence corresponding to the equivalent 5' end of the ~123 kb fragment of human genomic λ sequence described in Example 2. These two targeting vectors included, from 5' to 3', a 5' mouse homology arm containing either ~23 kb of genomic sequence 5' of the endogenous mouse κ light chain locus or ~24 kb of mouse genomic sequence 5' of the endogenous λ light chain locus, a 5' Frt site, a hygromycin cassette, a 3' Frt site and 171,457 bp of human genomic 2 sequence containing 21 consecutive hVλ gene segments, ~53 kb of which overlaps with the 5' end of the human λ sequence described in Example 3 and serves as the 3' homology arm for this targeting construct (FIGS. 5A and 5B, +16-λ or +16-κ Targeting Vectors). Homologous recombination with these targeting vectors created independently modified mouse κ and λ light chain loci each containing 28 hVλ gene segments and a hJλ1 gene segment operably linked to endogenous mouse constant genes (Cκ or Cλ2) which, upon recombination, leads to the formation of a chimeric light chain.

In a similar fashion, the +16-κ Targeting Vector was also used to introduce the 16 additional hVλ gene segments to the other initial modifications described in Example λ that incorporated multiple hJλ gene segments with and without an integrated human κ sequence (FIG. 4B). Homologous recombination with this targeting vector at the endogenous mouse κ locus containing the other initial modifications created mouse κ light chain loci containing 28 hVλ gene segments and hJλ1, 2, 3 and 7 gene segments with and without a human Vκ-Jκ genomic sequence operably linked to the endogenous mouse Cκ gene which, upon recombination, leads to the formation of a chimeric λ-κ light chain.

Introduction of 12 Additional Human Vλ Gene Segments.

Additional hVλ gene segments were added independently to each of the modifications described above using similar targeting vectors and methods. The final locus structure resulting from homologous recombination with targeting vectors containing additional hVλ gene segments are shown in FIGS. 7A and 7B.

Briefly, a targeting vector was engineered for introduction of 12 additional hVλ gene segments to the modified mouse κ and λ light chain loci described above (FIGS. 5A and 5B, +12-λ or 12-κ Targeting Vectors). A 93,674 bp DNA fragment from human BAC clone RP11-22I18 (Invitrogen) containing 12 consecutive hVλ gene segments from cluster B was engineered with a 5' homology arm containing mouse genomic sequence 5' to either the endogenous mouse κ or λ light chain loci and a 3' homology arm containing human genomic [ sequence. The 5' homology arms used in this targeting construct were the same 5' homology arms used for the addition of 16 hVλ gene segments described above (FIGS. 5A and 5B). The 3' homology arm was made by engineering a PI-SceI site ~3431 bp 5' to the human Vλ3-29P gene segment contained in a 27,468 bp genomic fragment of human λ sequence from BAC clone RP11-761I13. This PI-SceI site served as a ligation point to join the ~94 kb fragment of additional human λ sequence to the ~27 kb fragment of human λ sequence that overlaps with the 5' end of the human λ sequence in the previous modification using the +16-λ or +16-κ Targeting Vectors (FIGS. 5A and 5B). These two targeting vectors included, from 5' to 3', a 5' homology arm containing either ~23 kb of mouse genomic sequence 5' of the endogenous κ light chain locus or 24 kb of mouse genomic sequence 5' of the endogenous λ light chain locus, a 5' Frt site, a neomycin cassette, a 3' Frt site and 121,188 bp of human genomic λ sequence containing 16 hVλ gene segments and a PI-SceI site, ~27 kb of which overlaps with the 5' end of the human λ sequence from the insertion of 16 addition hVλ gene segments and serves as the 3' homology arm for this targeting construct (FIGS. 5A and 5B, +12-λ or 12-κ Targeting Vectors). Homologous recombination with these targeting vectors independently created modified mouse κ and λ light chain loci containing 40 hVλ gene segments and human Jλ1 operably linked to the endogenous mouse constant genes (Cκ or Cλ2) which, upon recombination, leads to the formation of a chimeric light chain (bottom of FIGS. 5A and 5B).

In a similar fashion, the +12-κ Targeting Vector was also used to introduce the 12 additional hVλ gene segments to the other initial modifications that incorporated multiple hJλ gene segments with and without an integrated human κ sequence (FIG. 4B). Homologous recombination with this targeting vector at the endogenous mouse κ locus containing the other modifications created a mouse κ light chain locus containing 40 hVλ gene segments and hJλ1, 2, 3 and 7 gene segments with and without a human Vκ-Jκ genomic sequence operably linked to the endogenous mouse Cκ gene which, upon recombination, leads to the formation of a chimeric λ-κ light chain.

Example IV

Identification of Targeted ES Cells Bearing Human λ Light Chain Gene Segments

Targeted BAC DNA made according to the foregoing Examples was used to electroporate mouse ES cells to create modified ES cells for generating chimeric mice that express human λ light chain gene segments. ES cells containing an insertion of unrearranged human λ light chain gene segments were identified by a quantitative TAQMAN® assay. Specific primers sets and probes were design for insertion of human λ sequences and associated selection cassettes (gain of allele, GOA), loss of endogenous mouse sequences and any selection cassettes (loss of allele, LOA) and retention of flanking mouse sequences (allele retention, AR). For each additional insertion of human λ sequences, additional primer sets and probes were used to confirm the presence of the additional human λ sequences as well as the previous primer sets and probes used to confirm retention of the previously targeted human sequences. Table 1 sets forth the primers and associated probes used in the quantitative PCR assays. Table λ sets forth the combinations used for confirming the insertion of each section of human [ light chain gene segments in ES cell clones.

ES cells bearing the human λ light chain gene segments are optionally transfected with a construct that expresses FLP in order to remove the Frt'ed neomycin cassette introduced by the insertion of the targeting construct containing human Vλ5-52 Vλ1-40 gene segments (FIGS. 5A and 5B). The neomycin cassette may optionally be removed by breeding to mice that express FLP recombinase (e.g., U.S. Pat. No. 6,774,279). Optionally, the neomycin cassette is retained in the mice.

TABLE 1

| Primer | SEQ ID NO: | Probe | SEQ ID NO: |
| --- | --- | --- | --- |
| hL2F | 2 | hL2P | 24 |
| hL2R | 3 | | |
| hL3F | 4 | hL3P | 25 |
| hL3R | 5 | | |
| NeoF | 6 | NeoP | 26 |
| NeoR | 7 | | |
| 61hJ1F | 8 | 61hJ1P | 27 |
| 61hJ1R | 9 | | |
| 67hT1F | 10 | 67hT1P | 28 |
| 67hT1R | 11 | | |
| 67hT3F | 12 | 67hT3P | 29 |
| 67hT3R | 13 | | |
| HygF | 14 | HygP | 30 |
| HygR | 15 | | |
| MKD2F | 16 | MKD2P | 31 |
| MKD2R | 17 | | |
| MKP8F | 18 | MKP8P | 32 |
| MKP8R | 19 | | |
| MKP15F | 20 | MKP15P | 33 |
| MKP15R | 21 | | |
| MK20F | 22 | — | — |
| MKP4R | 23 | | |
| 68h2F | 34 | 68h2P | 38 |
| 68h2R | 35 | | |
| 68h5F | 36 | 68h5P | 39 |
| 68h5R | 37 | | |
| mL1F | 75 | mL1P | 83 |
| mL1R | 76 | | |
| mL2F | 77 | mL2P | 84 |
| mL2R | 78 | | |
| mL11F | 79 | mL11P | 85 |
| mL11R | 80 | | |
| mL12F | 81 | mL12P | 86 |
| mL12R | 82 | | |

TABLE 2

| Modification | Assay | Forward/Reverse Primer Set | Probe | Sequence Location |
|---|---|---|---|---|
| Insertion of 12 hVλ & hJλ1 | GOA | hL2F/hL2R<br>hL3F/hL3R | hL2P<br>hL3P | hVλ3-12-hVλ3-1 |
| | | 61hJ1F/61hJ1R | 61hJ1P | hJλ sequence |
| | | NeoF/NeoR | NeoP | Neomycin cassette |
| | LOA | MK20F/MKP4R | — | lox511/loxP sequence of inactivated κ locus |
| | | HygF/HygR | HygP | Hygromycin cassette from inactivated λ locus |
| | | mL1F/mL1R | mL1P | Mouse Vλ1-Cλ1 |
| | | mL2F/mL2R | mL2P | Cluster |
| | | mL11F/mL11R | mL11P | Mouse Vλ2-Cλ2 |
| | | mL12F/mL12R | mL12P | Cluster |
| | AR/LOA | MKD2F/MKD2R | MKD2P | Mouse sequence in 5' Vκ locus |
| | | MKP15F/MKP15R | MKP15P | Mouse sequence in 3' Vκ locus |
| Insertion of 16 hVλ | GOA | 67hT1F/67hT1R<br>67hT3F/67hT3R | 67hT1P<br>67hT3P | hVλ3-27-hVλ3-12 |
| | | HygF/HygR | HygP | Hygromycin cassette |
| | LOA | NeoF/NeoR | NeoP | Neomycin cassette |
| | | mL1F/mL1R | mL1P | Mouse Vλ1-Cλ1 |
| | | mL2F/mL2R | mL2P | Cluster |
| | | mL11F/mL11R | mL11P | Mouse Vλ2-Cλ2 |
| | | mL12F/mL12R | mL12P | Cluster |
| | AR | hL2F/hL2R<br>hL3F/hL3R | hL2P<br>hL3P | hVλ3-12-hVλ3-1 |
| | AR/LOA | MKD2F/MKD2R | MKD2P | Mouse sequence in 5' Vκ locus |
| | | MKP15F/MKP15R | MKP15P | Mouse sequence in 3' Vκ locus |
| Insertion of 12 hVλ | GOA | 68h2F/68h2R<br>68h5F/68h5R | 68h2P<br>68h5P | hVλ5-52-hVλ1-40 |
| | | NeoF/NeoR | NeoP | Neomycin cassette |
| | LOA | HygF/HygR | HygP | Hygromycin cassette |
| | | mL1F/mL1R | mL1P | Mouse Vλ1-Cλ1 |
| | | mL2F/mL2R | mL2P | Cluster |
| | | mL11F/mL11R | mL11P | Mouse Vλ2-Cλ2 |
| | | mL12F/mL12R | mL12P | Cluster |
| | AR | hL2F/hL2R<br>hL3F/hL3R | hL2P<br>hL3P | hVλ3-12-hVλ3-1 |
| | | 67hT1F/67hT1R<br>67hT3F/67hT3R | 67hT1P<br>67hT3P | hVλ3-27-hVλ3-12 |
| | AR/LOA | MKD2F/MKD2R | MKD2P | Mouse sequence in 5' Vκ locus |
| | | MKP15F/MKP15R | MKP15P | Mouse sequence in 3' Vκ locus |

Example V

Generation of Mice Expressing Human λ, Light Chains from an Endogenous Light Chain Locus Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99. VELOCIMICE® (F0 mice fully derived from the donor ES cell) independently bearing human 2 gene segments were identified by genotyping using a modification of allele assay (Valenzuela et al., supra) that detected the presence of the unique human λ gene segments (supra).

κ:λ Light Chain Usage of Mice Bearing Human λ, Light Chain Gene Segments.

Mice homozygous for each of three successive insertions of hVλ gene segments with a single hJλ gene segment (FIG. 5B) and mice homozygous for a first insertion of hVλ gene segments with either a single hJλ gene segment or four human Jλ gene segments including a human Vκ-Jκ genomic sequence (FIG. 4B) were analyzed for κ and λ light chain expression in splenocytes using flow cytometry.

Briefly, spleens were harvested from groups of mice (ranging from three to seven animals per group) and grinded using glass slides. Following lysis of red blood cells (RBCS) with ACK lysis buffer (Lonza Walkersville), splenocytes were stained with fluorescent dye conjugated antibodies specific for mouse CD19 (Clone 1 D3; BD Biosciences), mouse CD3 (17A2; Biolegend), mouse Igκ (187.1; BD Biosciences) and mouse Igλ (RML-42; Biolegend). Data was acquired using a BD™ LSR II flow cytometer (BD Biosciences) and analyzed using FLOWJO™ software (Tree Star, Inc.). Table 3 sets forth the average percent values for B cells (CD19$^+$), κ light chain (CD19$^+$Igκ$^+$Igλ$^-$), and λ light chain (CD19$^+$Igκ$^-$Igλ$^+$) expression observed in splenocytes from groups of animals bearing each genetic modification.

Figure 8A:
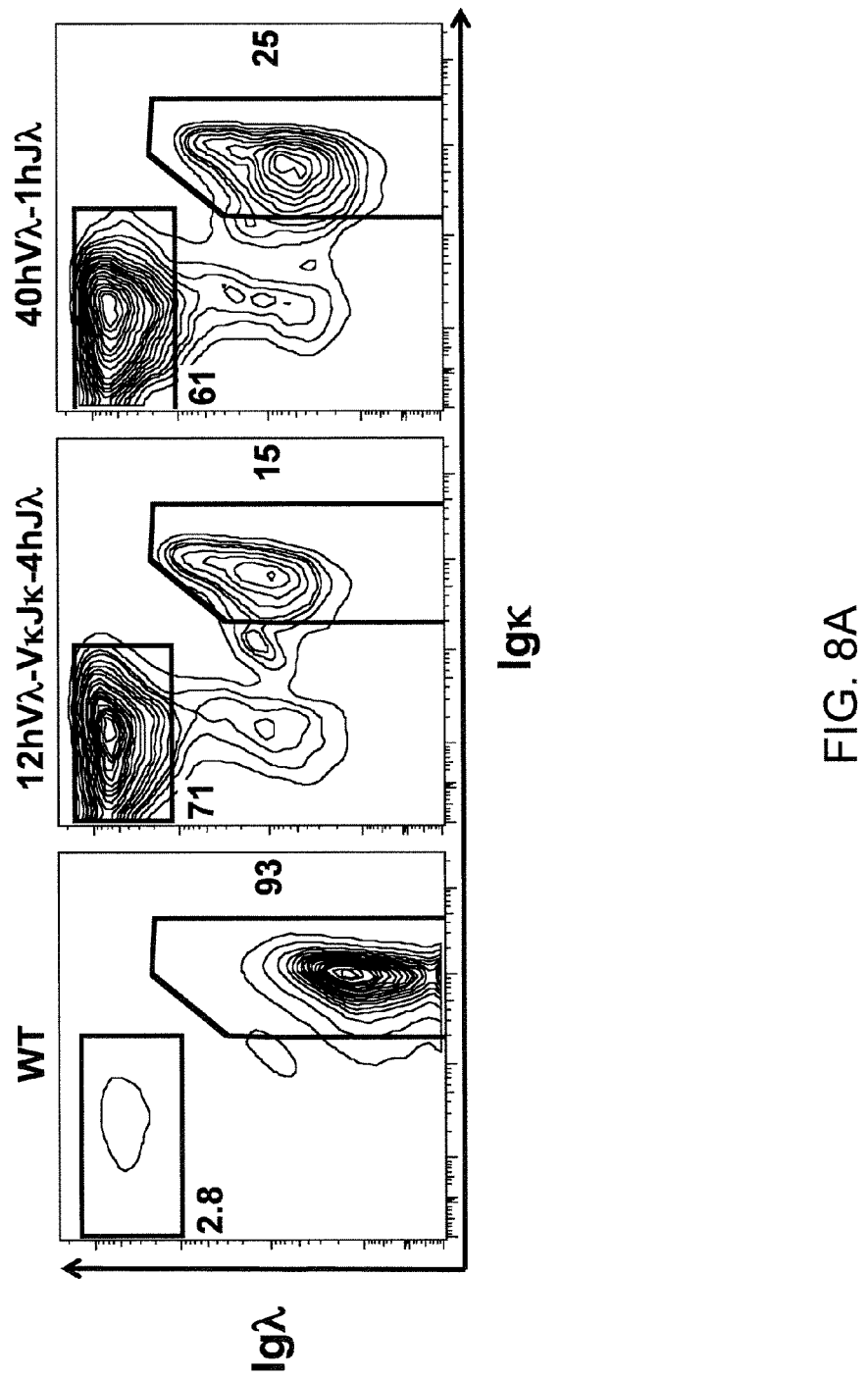
FIG. 8A shows contour plots of Igλ$^+$ and Igκ$^+$ splenocytes gated on CD19$^+$ from a wild type mouse (WT), a mouse homozygous for 12 hVλ and four hJλ gene segments including a human Vκ-Jκ genomic sequence (12hVλ-VκJκ-4hJλ) and a mouse homozygous for 40 hVλ and one hJλ gene segment (40hVλ-1hJλ).
Figure 8B:
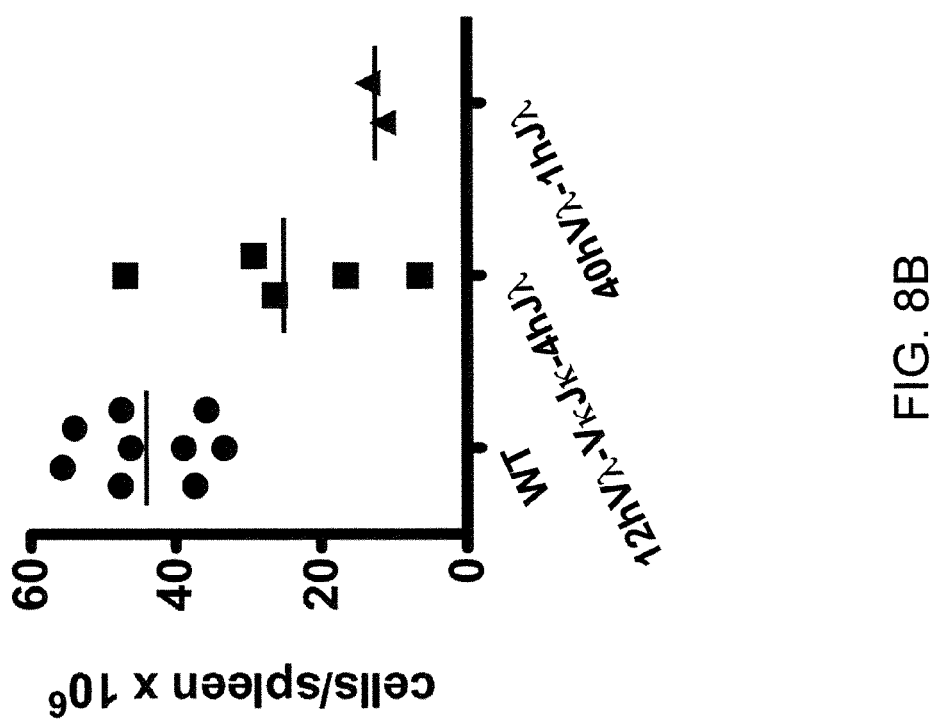
FIG. 8B shows the total number of CD19$^+$ B cells in harvested spleens from wild type (WT), mice homozygous for 12 hVλ and four hJλ gene segments including a human Vκ-Jκ genomic sequence (12hVλ-VκJκ-4hJλ) and mice homozygous for 40 hVλ and one hJλ gene segment (40hVλ-1hJλ).

In a similar experiment, B cell contents of the splenic compartment from mice homozygous for a first insertion of 12 hVλ and four hJλ gene segments including a human Vκ-Jκ genomic sequence operably linked to the mouse Cκ gene (bottom of FIG. 4B) and mice homozygous for 40 hVλ and one hJλ gene segment (bottom of FIG. 5B or top of FIG. 7B) were analyzed for Igκ and Igλ expression using flow cytometry (as described above). FIG. 8A shows the Igλ and Igκ expression in CD19+ B cells for a representative mouse from each group. The number of CD19+ B cells per spleen was also recorded for each mouse (FIG. 8B).

In another experiment, B cell contents of the spleen and bone marrow compartments from mice homozygous for 40 hVλ and four hJλ gene segments including a human Vκ-Jκ genomic sequence operably linked to the mouse Cκ gene (bottom of FIG. 7B) were analyzed for progression through B cell development using flow cytometry of various cell surface markers.

Briefly, two groups (N=3 each, 9-12 weeks old, male and female) of wild type and mice homozygous for 40 hVλ and four hJλ gene segments including a human Vκ-Jκ genomic sequence operably linked to the mouse Cκ gene were sacrificed and spleens and bone marrow were harvested. Bone marrow was collected from femurs by flushing with complete RPMI medium (RPMI medium supplemented with fetal calf serum, sodium pyruvate, Hepes, 2-mercaptoethanol, non-essential amino acids, and gentamycin). RBCs from spleen and bone marrow preparations were lysed with ACK lysis buffer (Lonza Walkersville), followed by washing with complete RPMI medium. $1 \times 10^6$ cells were incubated with anti-mouse CD16/CD32 (2.4G2, BD Biosciences) on ice for 10 minutes, followed by labeling with a selected antibody panel for 30 min on ice.

Bone marrow panel: anti-mouse FITC-CD43 (1B11, BioLegend), PE-ckit (2B8, BioLegend), PeCy7-IgM (11/41, eBioscience), PerCP-Cy5.5-IgD (11-26c.2a, BioLegend), APC-B220 (RA3-6B2, eBioscience), APC-H7-CD19 (ID3, BD) and Pacific Blue-CD3 (17A2, BioLegend).

Bone marrow and spleen panel: anti-mouse FITC-Igκ (187.1, BD), PE-Igλ (RML-42, BioLegend), PeCy7-IgM (11/41, ebioscience), PerCP-Cy5.5-IgD (11-26c.2a, BioLegend), Pacific Blue-CD3 (17A2, BioLegend), APC-B220 (RA3-6B2, eBioscience), APC-H7-CD19 (ID3, BD).

Following staining, cells were washed and fixed in 2% formaldehyde. Data acquisition was performed on a FACS-CANTOII™ flow cytometer (BD Biosciences) and analyzed with FLOWJO™ software (Tree Star, Inc.). FIGS. 9A-9D show the results for the splenic compartment of one representative mouse from each group. FIGS. 10A-10E show the results for the bone marrow compartment of one representative mouse from each group. Table 4 sets forth the average percent values for B cells (CD19+), κ light chain (CD19+Igκ+Igλ−), and λ light chain (CD19+Igκ−Igλ+) expression observed in splenocytes from groups of animals bearing various genetic modifications. Table 5 sets forth the average percent values for B cells (CD19+), mature B cells (B220$^{hi}$IgM+), immature B cells (B220$^{int}$IgM+), immature B cells expressing κ light chain (B220$^{int}$IgM+Igκ+) and immature B cells expressing λ light chain (B220$^{int}$IgM+Igλ+) observed in bone marrow of wild type and mice homozygous for 40 hVλ and four hJλ gene segments including a human Vκ-Jκ genomic sequence operably linked to the mouse Cκ gene. This experiment was repeated with additional groups of the mice described above and demonstrated similar results (data not shown).

TABLE 3

| Genotype | % B cells | % Igκ+ | % Igλ+ |
|---|---|---|---|
| Wild Type | 46.2 | 91.0 | 3.6 |
| 12 hVλ + hJλ1 | 28.3 | 10.4 | 62.5 |

TABLE 3-continued

| Genotype | % B cells | % Igκ+ | % Igλ+ |
|---|---|---|---|
| 12 hVλ − VκJκ − hJλ1 | 12.0 | 11.0 | 67.5 |
| 12 hVλ − VκJκ − 4hJλ | 41.8 | 17.2 | 68.4 |
| 28 hVλ + hJλ1 | 22.0 | 13.3 | 51.1 |
| 40 hVλ + hJλ1 | 28.2 | 24.3 | 53.0 |

TABLE 4

| Genotype | % B cells | % Igκ+ | % Igλ+ |
|---|---|---|---|
| Wild Type | 49.8 | 91.2 | 3.5 |
| 40 hVλ − VκJκ − 4hJλ | 33.3 | 41.6 | 43.1 |

TABLE 5

| Genotype | % B cells | % Mature B cells | % Immature B cells | % Immature Igκ+ B cells | % Immature Igλ+ B cells |
|---|---|---|---|---|---|
| Wild Type | 62.2 | 9.2 | 12.0 | 79.0 | 8.84 |
| 40hVλ − VκJκ − 4hJλ | 60.43 | 2.59 | 7.69 | 38.29 | 43.29 |

Human Vλ Gene Usage in Mice Bearing Human λ, Light Chain Gene Segments.

Mice heterozygous for a first insertion of human λ sequences (hVλ3-12-hVλ3-1 and hJλ1, FIG. 5B) and homozygous for a third insertion of human λ sequences (hVλ5-52-hVλ3-1 and hJλ1, FIG. 5B) were analyzed for human λ light chain gene usage by reverse-transcriptase polymerase chain reaction (RT-PCR) using RNA isolated from splenocytes.

Briefly, spleens were harvested and perfused with 10 mL RPMI-1640 (Sigma) with 5% HI-FBS in sterile disposable bags. Each bag containing a single spleen was then placed into a STOMACHER™ (Seward) and homogenized at a medium setting for 30 seconds. Homogenized spleens were filtered using a 0.7 μm cell strainer and then pelleted with a centrifuge (1000 rpm for 10 minutes) and RBCs were lysed in BD PHARM LYSE™ (BD Biosciences) for three minutes. Splenocytes were diluted with RPMI-1640 and centrifuged again, followed by resuspension in 1 mL of PBS (Irvine Scientific). RNA was isolated from pelleted splenocytes using standard techniques known in the art.

RT-PCR was performed on splenocyte RNA using primers specific for human hVλ gene segments and the mouse Cκ gene (Table 6). PCR products were gel-purified and cloned into pCR2.1-TOPO TA vector (Invitrogen) and sequenced with primers M13 Forward (GTAAAACGAC GGCCAG; SEQ ID NO:55) and M13 Reverse (CAGGAAACAG CTAT-GAC; SEQ ID NO:56) located within the vector at locations flanking the cloning site. Eighty-four total clones derived from the first and third insertions of human λ sequences were sequenced to determine hVλ gene usage (Table 7). The nucleotide sequence of the hVλ-hJλ1-mCκ junction for selected RT-PCR clones is shown in FIG. 11.

In a similar fashion, mice homozygous for a third insertion of human λ light chain gene sequences (i.e. 40 hVλ gene segments and four hJλ gene segments including a human Vκ-Jκ genomic sequence, bottom of FIG. 7B) operably linked to the endogenous mouse Cκ gene were analyzed for human λ light chain gene usage by RT-PCR using RNA isolated from splenocytes (as described above). The human λ light chain gene segment usage for 26 selected RT-PCR clones are shown in Table 8. The nucleotide sequence of the hVλ-hJλ-mCκ junction for selected RT-PCR clones is shown in FIG. 12.

In a similar fashion, mice homozygous for a first insertion of human λ light chain gene segments (12 hVλ gene segments and hJλ1, FIG. 4A & FIG. 5A) operably linked to the endogenous mouse Cλ2 gene were analyzed for human λ light chain gene usage by RT-PCR using RNA isolated from splenocytes (as described above). The primers specific for hVλ gene segments (Table 6) were paired with one of two primers specific for the mouse Cλ2 gene; Cλ2-1 (SEQ ID NO:104) or Cλ2-2 (SEQ ID NO:105).

Multiple hVλ gene segments rearranged to hλ1 were observed from the RT-PCR clones from mice bearing human λ light chain gene segments at the endogenous mouse λ light chain locus. The nucleotide sequence of the hVλ-hJλ-mCλ2 junction for selected RT-PCR clones is shown in FIG. 13.

TABLE 6

|  | Sequence (5'-3') | SEQ ID NO: |
|---|---|---|
| 5' hVγ Primer |  |  |
| VLL-1 | CCTCTCCTCC TCACCCTCCT | 40 |
| VLL-1n | ATGRCCDGST YYYCTCTCCT | 41 |
| VLL-2 | CTCCTCACTC AGGGCACA | 42 |
| VLL-2n | ATGGCCTGGG CTCTGCTSCT | 43 |
| VLL-3 | ATGGCCTGGA YCSCTCTCC | 44 |
| VLL-4 | TCACCATGGC YTGGRYCYCM YTC | 45 |
| VLL-4.3 | TCACCATGGC CTGGGTCTCC TT | 46 |
| VLL-5 | TCACCATGGC CTGGAMTCYT CT | 47 |
| VLL-6 | TCACCATGGC CTGGGCTCCA CTACTT | 48 |
| VLL-7 | TCACCATGGC CTGGACTCCT | 49 |
| VLL-8 | TCACCATGGC CTGGATGATG CTT | 50 |
| VLL-9 | TAAATATGGC CTGGGCTCCT CT | 51 |
| VLL-10 | TCACCATGCC CTGGGCTCTG CT | 52 |
| VLL-11 | TCACCATGGC CCTGACTCCT CT | 53 |
| 3' Mouse Cκ Primer |  |  |
| mIgKC3'-1 | CCCAAGCTTA CTGGATGGTG GGAAGATGGA | 54 |

TABLE 7

| hVλ | Observed No. of Clones |
|---|---|
| 3-1 | 2 |
| 4-3 | 3 |
| 2-8 | 7 |

TABLE 7-continued

| hVλ | Observed No. of Clones |
|---|---|
| 3-9 | 4 |
| 3-10 | 3 |
| 2-14 | 1 |
| 3-19 | 1 |
| 2-23 | 7 |
| 3-25 | 1 |
| 1-40 | 9 |
| 7-43 | 2 |
| 1-44 | 2 |
| 5-45 | 8 |
| 7-46 | 3 |
| 9-49 | 6 |
| 1-51 | 3 |

TABLE 8

| Clone | hVλ | hJλ |
|---|---|---|
| 1-3 | 1-44 | 7 |
| 1-5 | 1-51 | 3 |
| 2-3 | 9-49 | 7 |
| 2-5 | 1-40 | 1 |
| 2-6 | 1-40 | 7 |
| 3b-5 | 3-1 | 7 |
| 4a-1 | 4-3 | 7 |
| 4a-5 | 4-3 | 7 |
| 4b-1 | 1-47 | 3 |
| 5-1 | 3-10 | 3 |
| 5-2 | 1-40 | 7 |
| 5-3 | 1-40 | 7 |
| 5-4 | 7-46 | 2 |
| 5-6 | 1-40 | 7 |
| 5-7 | 7-43 | 3 |
| 6-1 | 1-40 | 1 |
| 6-2 | 1-40 | 2 |
| 6-7 | 1-40 | 3 |
| 7a-1 | 3-10 | 7 |
| 7a-2 | 9-49 | 2 |
| 7a-7 | 3-10 | 7 |
| 7b-2 | 7-43 | 3 |
| 7b-7 | 7-46 | 7 |
| 7b-8 | 7-43 | 3 |
| 11a-1 | 5-45 | 2 |
| 11a-2 | 5-45 | 7 |

FIG. 11 shows the sequence of the hVλ-hJλ1-mCκ junction for RT-PCR clones from mice bearing a first and third insertion of hVλ gene segments with a single hJλ gene segment. The sequences shown in FIG. 11 illustrate unique rearrangements involving different hVλ gene segments with hJλ1 recombined to the mouse Cκ gene. Heterozygous mice bearing a single modified endogenous κ locus containing 12 hVλ gene segments and hJλ1 and homozygous mice bearing two modified endogenous κ loci containing 40 hVλ gene segments and hJλ1 were both able to produce human λ gene segments operably linked to the mouse Cκ gene and produce B cells that expressed human λ light chains. These rearrangements demonstrate that the chimeric loci were able to independently rearrange human λ gene segments in multiple, independent B cells in these mice. Further, these modifications to the endogenous κ light chain locus did not render any of the hVλ gene segments inoperable or prevent the chimeric locus from recombining multiple hVλ and a hJλ (Jλ1) gene segment during B cell development as evidenced by 16 different hVλ gene segments that were observed to rearrange with hJλ1 (Table 7). Further, these mice made functional antibodies containing rearranged human Vλ-Jλ gene segments operably linked to mouse Cκ genes as part of the endogenous immunoglobulin light chain repertoire.

FIG. 12 shows the sequence of the hVλ-hJλ-mCκ junction for selected RT-PCR clones from mice homozygous for 40 hVλ and four hJλ gene segments including a human Vκ-Jκ genomic sequence. The sequences shown in FIG. 12 illustrate additional unique rearrangements involving multiple different hVλ gene segments, spanning the entire chimeric locus, with multiple different hJλ gene segments rearranged and operably linked to the mouse Cκ gene. Homozygous mice bearing modified endogenous κ loci containing 40 hVλ and four hJλ gene segments were also able to produce human λ gene segments operably linked to the mouse Cκ gene and produce B cells that expressed human λ light chains. These rearrangements further demonstrate that the all stages of chimeric loci were able to independently rearrange human λ gene segments in multiple, independent B cells in these mice. Further, these additional modifications to the endogenous κ light chain locus demonstrates that each insertion of human λ gene segments did not render any of the hVλ and/or Jλ gene segments inoperable or prevent the chimeric locus from recombining the hVλ and Jλ gene segments during B cell development as evidenced by 12 different hVλ gene segments that were observed to rearrange with all four hJλ gene segments (Table 8) from the 26 selected RT-PCR clone. Further, these mice as well made functional antibodies containing human Vλ-Jλ gene segments operably linked to mouse Cκ regions as part of the endogenous immunoglobulin light chain repertoire.

FIG. 13 shows the sequence of the hVλ-hJλ-mCλ2 junction for three individual RT-PCR clones from mice homozygous for 12 hVλ gene segments and hJλ1. The sequences shown in FIG. 13 illustrate additional unique rearrangements involving different hVλ gene segments, spanning the length of the first insertion, with hJλ1 rearranged and operably linked to the mouse Cλ2 gene (2D1=Vλ2-8Jλ1; 2D9=Vλ3-10Jλ1; 3E15=Vλ3-1Jλ1). One clone demonstrated a nonproductive rearrangement due to N additions at the hVλ-hJλ junction (2D1, FIG. 13). This is not uncommon in V(D)J recombination, as the joining of gene segments during recombination has been shown to be imprecise. Although this clone represents an unproductive recombinant present in the light chain repertoire of these mice, this demonstrates that the genetic mechanism that contributes to junctional diversity among antibody genes is operating normally in these mice and leading to an antibody repertoire containing light chains with greater diversity.

Homozygous mice bearing modified endogenous λ loci containing 12 hVλ gene segments and hJλ1 were also able to produce human λ gene segments operably linked to an endogenous mouse Cλ gene and produce B cells that expressed reverse chimeric λ light chains containing hVλ regions linked to mouse Cλ regions. These rearrangements further demonstrate that human λ light chain gene segments placed at the other light chain locus (i.e., the λ locus) were able to independently rearrange human λ gene segments in multiple, independent B cells in these mice. Further, the modifications to the endogenous λ light chain locus demonstrate that the insertion of human λ gene segments did not render any of the hVλ and/or hJλ1 gene segments inoperable or prevent the chimeric locus from recombining the hVλ and hJλ1 gene segments during B cell development. Further, these mice also made functional antibodies containing human Vλ-Jλ gene segments operably linked to a mouse Cλ region as part of the endogenous immunoglobulin light chain repertoire.

Figure 9A:
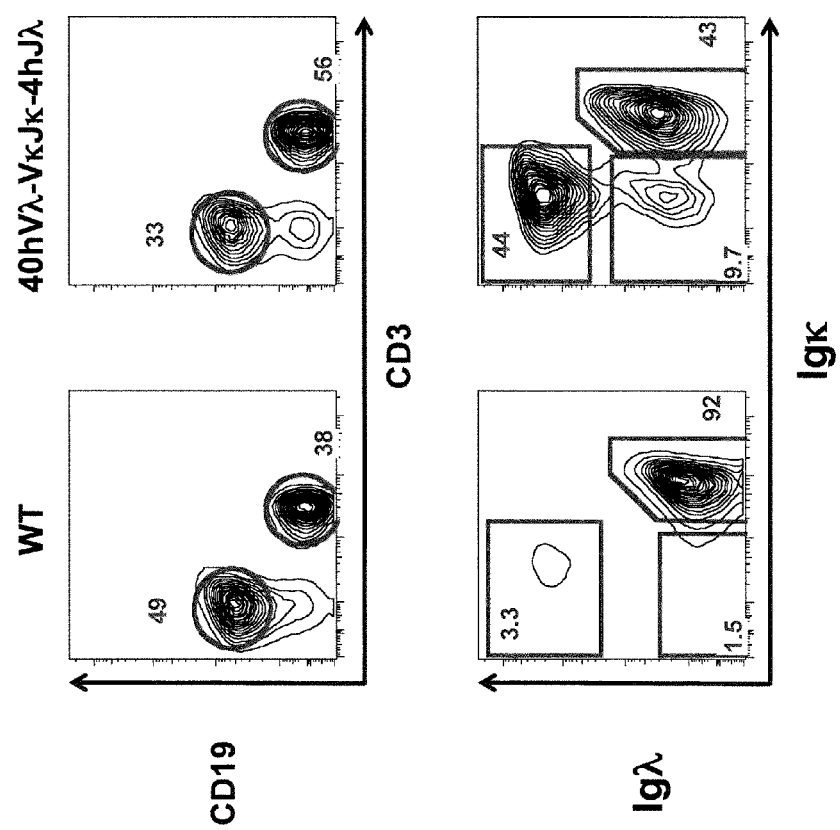
FIG. 9A, in the top panel, shows contour plots of splenocytes gated on singlets and stained for B and T cells (CD19$^+$ and CD3$^+$, respectively) from a wild type mouse (WT) and a mouse homozygous for 40 hVλ and four Jλ gene segments including a human Vκ-Jκ genomic sequence (40hVλ-VκR-4hJλ). The bottom panel shows contour plots of splenocytes gated on CD19$^+$ and stained for Igλ$^+$ and Igκ$^+$ expression from a wild type mouse (WT) and a mouse homozygous for 40 hVλ and four Jλ gene segments including a human Vκ-Jκ genomic sequence (40hVλ-VκJκ-4hJλ).
Figure 9B:
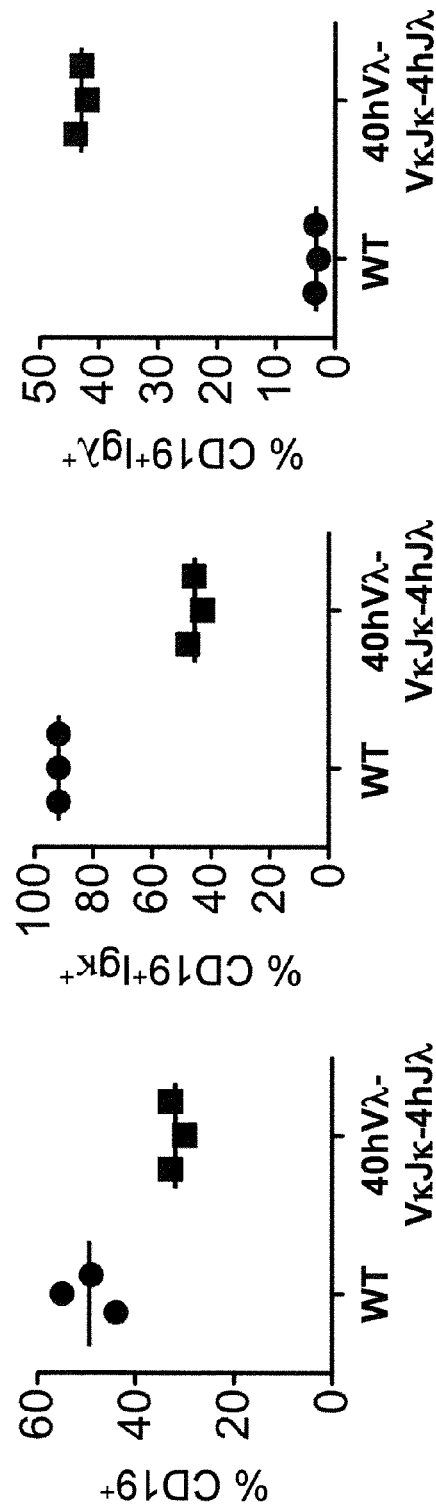
FIG. 9B shows the total number of CD19$^+$, CD19$^+$Igκ$^+$ and CD19$^+$Igλ$^+$ B cells in harvested spleens from wild type mice (WT) and mice homozygous for 40 hVλ and four Jλ gene segments including a human Vκ-Jκ genomic sequence (40hVλ-VκJκ-4hJλ).
Figure 9C:
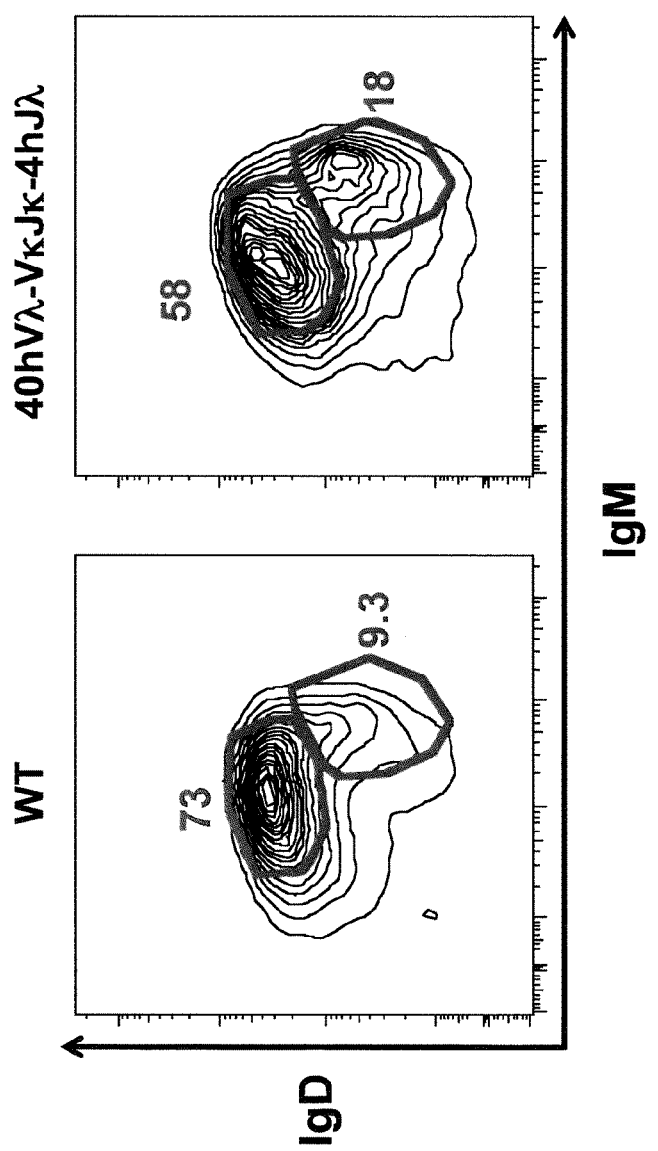
FIG. 9C shows contour plots of splenocytes gated on CD19+ and stained for immunoglobulin D (IgD) and immunoglobulin M (IgM) from a wild type mouse (WT) and a mouse homozygous for 40 hVλ and four Jλ gene segments including a human Vκ-Jκ genomic sequence (40hVλ-VκJκ-4hJλ). Mature (72 for WT, 51 for 40hVλ-VκJκ-4hJλ) and transitional (13 for WT, 22 for 40hVλ-VκJκ-4hJλ) B cells are noted on each of the contour plots.
Figure 9D:
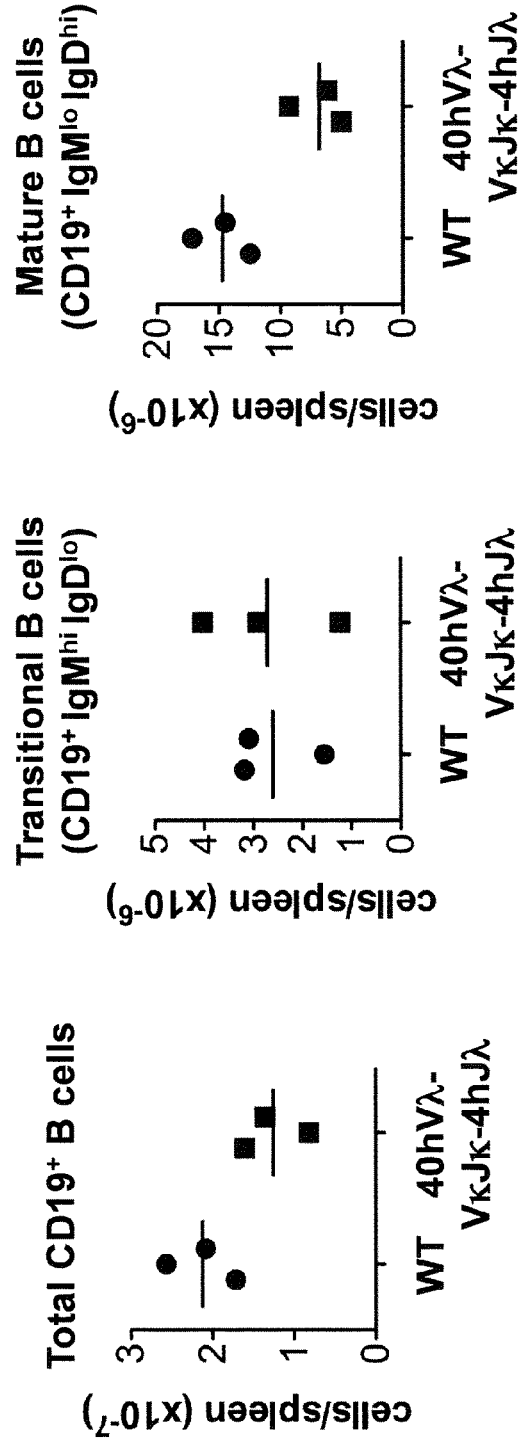
FIG. 9D shows the total number of CD19+ B cells, transitional B cells (CD19+IgM$^{hi}$IgD$^{lo}$) and mature B cells (CD19+IgM$^{lo}$IgD$^{hi}$) in harvested spleens from wild type mice (WT) and mice homozygous for 40 hVλ and four Jλ gene segments including a human Vκ-Jκ genomic sequence (40hVλ-VκJκ-4hJλ).
Figure 10A:
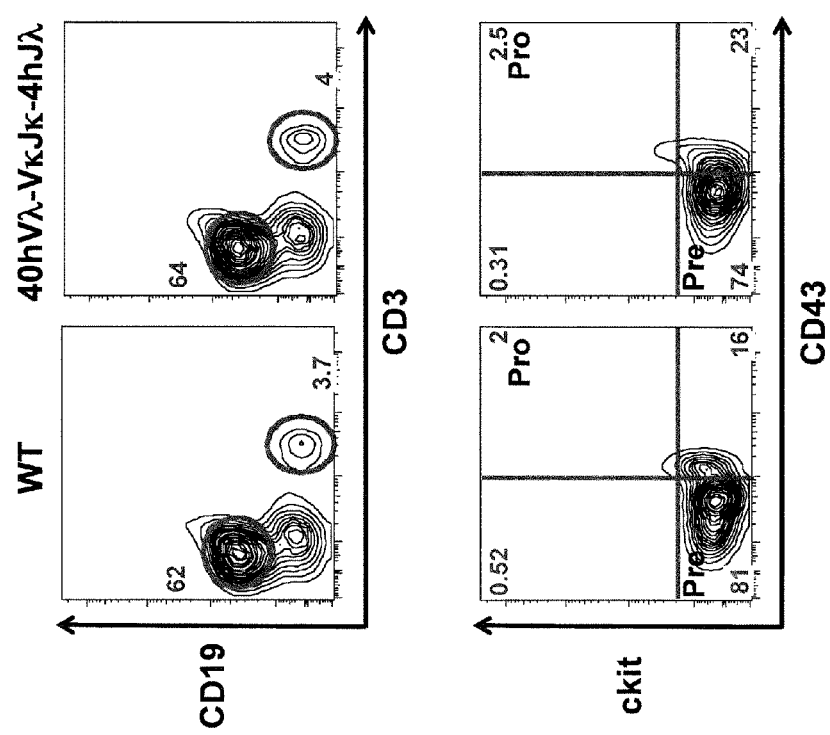
FIG. 10A, in the top panel, shows contour plots of bone marrow stained for B and T cells (CD19+ and CD3+, respectively) from a wild type mouse (WT) and a mouse homozygous for 40 hVλ and four Jλ gene segments including a human Vκ-Jκ genomic sequence (40hVλ-VκJκ-4hJλ). The bottom panel shows contour plots of bone marrow gated on CD19+ and stained for ckit+ and CD43+ from a wild type mouse (WT) and a mouse homozygous for 40 hVλ and four Jλ gene segments including a human Vκ-Jκ genomic sequence (40hVλ-VκJκ-4hJλ). Pro and Pre B cells are noted on the contour plots of the bottom panel.
Figure 10B:
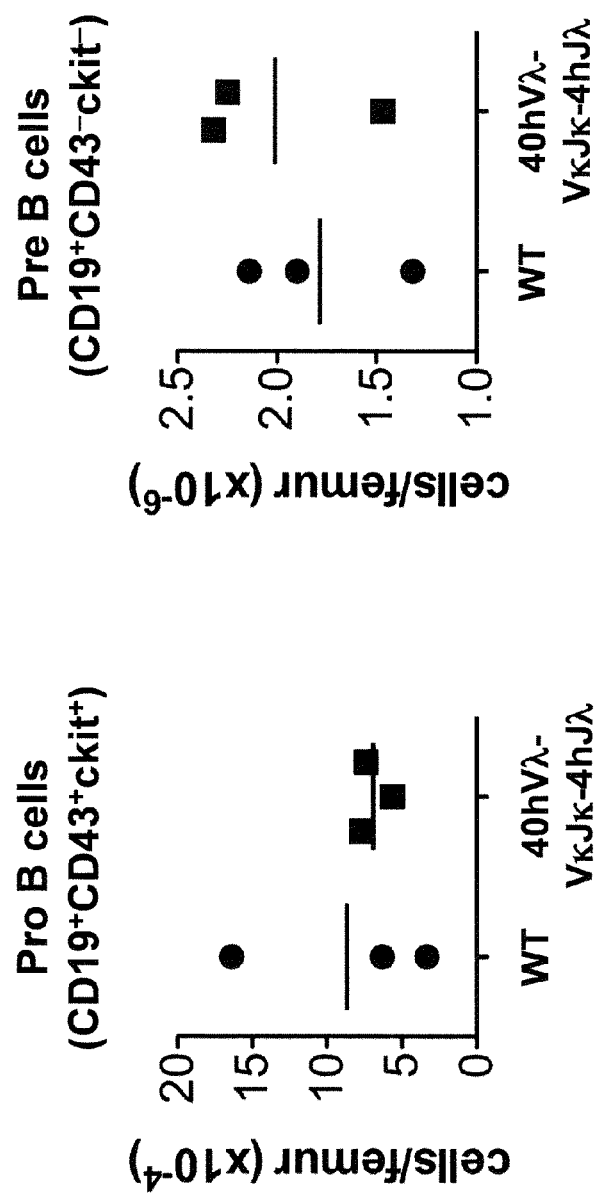
FIG. 10B shows the number of Pro (CD19+CD43+ckit+) and Pre (CD19+CD43−ckit−) B cells in bone marrow harvested from the femurs of wild type mice (WT) and mice homozygous for 40 hVλ and four Jλ gene segments including a human Vκ-Jκ genomic sequence (40hVλ-VκJκ-4hJλ).
Figure 10C:
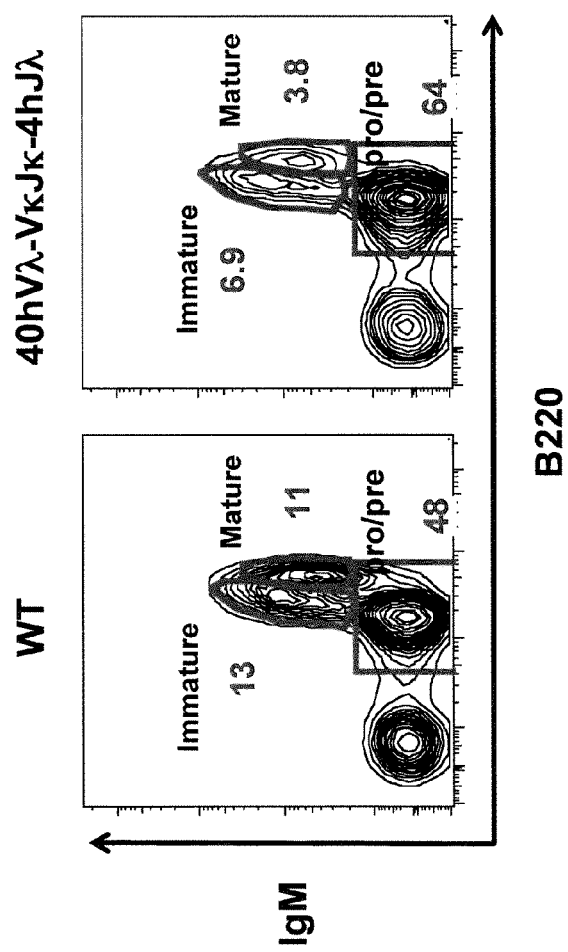
FIG. 10C shows contour plots of bone marrow gated on singlets stained for immunoglobulin M (IgM) and B220 from a wild type mouse (WT) and a mouse homozygous for 40 hVλ and four Jλ gene segments including a human Vκ-Jκ genomic sequence (40hVλ-VκJκ-4hJλ). Immature, mature and pro/pre B cells are noted on each of the contour plots.
Figure 10D:
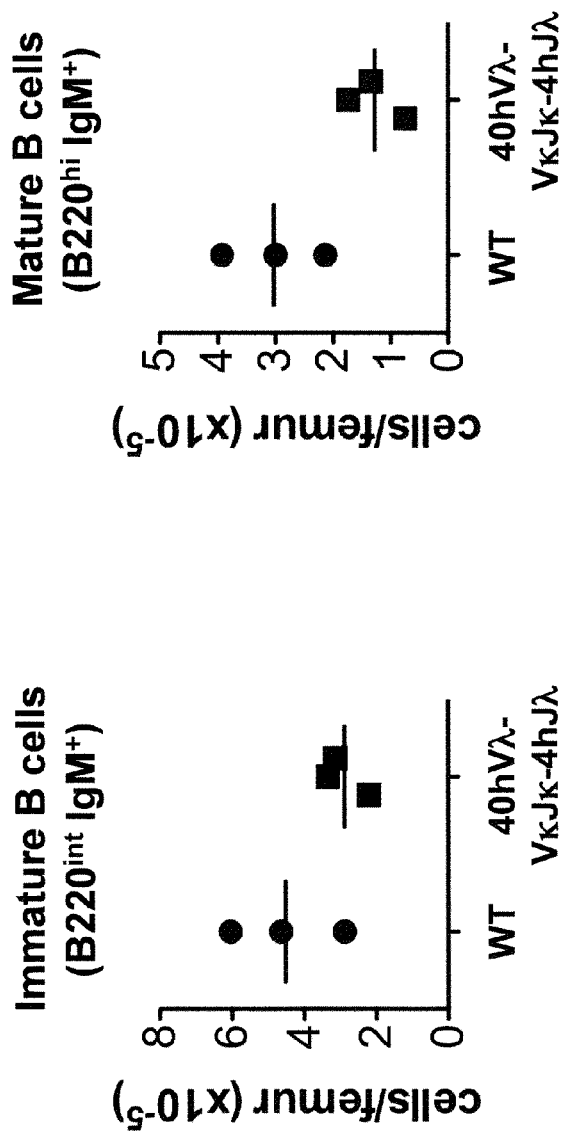
FIG. 10D shows the total number of immature (B220$^{int}$IgM+) and mature (B220$^{hi}$IgM+) B cells in bone marrow isolated from the femurs of wild type mice (WT) and mice homozygous for 40 hVλ and four Jλ gene segments including a human Vκ-Jκ genomic sequence (40hVλ-VκJκ-4hJλ).
Figure 10E:
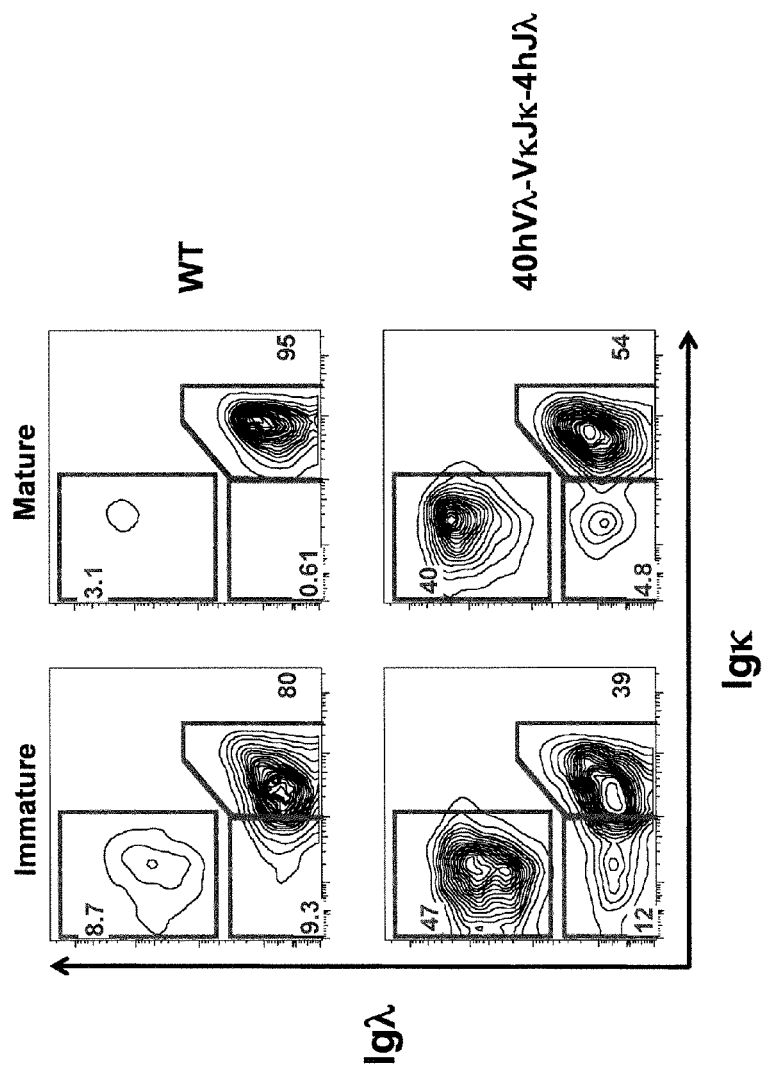
FIG. 10E shows contour plots of bone marrow gated on immature (B220$^{int}$IgM+) and mature (B220$^{hi}$IgM+) B cells stained for Igλ and Igκ expression isolated from the femurs of a wild type mouse (WT) and a mouse homozygous for 40 hVλ and four Jλ gene segments including a human Vκ-Jκ genomic sequence (40hVλ-VκJκ-4hJλ).

As shown in this Example, mice bearing human λ light chain gene segments at the endogenous κ and λ light chain loci are capable of rearranging human λ light chain gene segments and expressing them in the context of a mouse Cκ and/or Cλ region as part of the normal antibody repertoire of the mouse because a functional light chain is required at various checkpoints in B cell development in both the spleen and bone marrow. Further, early subsets of B cells (e.g., pre-, pro- and transitional B cells) demonstrate a normal phenotype in these mice as compared to wild type littermates (FIGS. 9D, 10A and 10B). A small deficit in bone marrow and peripheral B cell populations was observed, which may be attributed to a deletion of a subset of auto-reactive immature B cells and/or a suboptimal association of human λ light chain with mouse heavy chain. However, the Igκ/Igλ usage observed in these mice demonstrates a situation that is more like human light chain expression than that observed in mice.

Example VI

Breeding of Mice Expressing Human λ Light Chains from an Endogenous Light Chain Locus To optimize the usage of the human λ gene segments at an endogenous mouse light chain locus, mice bearing the unrearranged human λ gene segments are bred to another mouse containing a deletion in the opposing endogenous light chain locus (either κ or λ). For example, human λ gene segments positioned at the endogenous κ locus would be the only functional light chain gene segments present in a mouse that also carried a deletion in the endogenous λ light chain locus. In this manner, the progeny obtained would express only human λ light chains as described in the foregoing examples. Breeding is performed by standard techniques recognized in the art and, alternatively, by commercial companies, e.g., The Jackson Laboratory. Mouse strains bearing human λ light chain gene segments at the endogenous κ locus and a deletion of the endogenous λ light chain locus are screened for presence of the unique reverse-chimeric (human-mouse) λ light chains and absence of endogenous mouse λ light chains.

Mice bearing an unrearranged human λ light chain locus are also bred with mice that contain a replacement of the endogenous mouse heavy chain variable gene locus with the human heavy chain variable gene locus (see U.S. Pat. No. 6,596,541, Regeneron Pharmaceuticals, the VELOCIMMUNE® genetically engineered mouse). The VELOCIMMUNE® mouse includes, in part, having a genome comprising human heavy chain variable regions operably linked to endogenous mouse constant region loci such that the mouse produces antibodies comprising a human heavy chain variable region and a mouse heavy chain constant region in response to antigenic stimulation. The DNA encoding the variable regions of the heavy chains of the antibodies can be isolated and operably linked to DNA encoding the human heavy chain constant regions. The DNA can then be expressed in a cell capable of expressing the fully human heavy chain of the antibody. Upon a suitable breeding schedule, mice bearing a replacement of the endogenous mouse heavy chain locus with the human heavy chain locus and an unrearranged human λ light chain locus at the endogenous κ light chain locus is obtained. Antibodies containing somatically mutated human heavy chain variable regions and human λ light chain variable regions can be isolated upon immunization with an antigen of interest.

Example VII

Generation of Antibodies from Mice Expressing Human Heavy Chains and Human λ Light Chains After breeding mice that contain the unrearranged human λ light chain locus to various desired strains containing modifications and deletions of other endogenous Ig loci (as described above), selected mice are immunized with an antigen of interest.

Generally, a VELOCIMMUNE® mouse containing one of the single rearranged human germline light chain regions is challenged with an antigen, and lymphatic cells (such as B-cells) are recovered from serum of the animals. The lymphatic cells may be fused with a myeloma cell line to prepare immortal hybridoma cell lines, and such hybridoma cell lines are screened and selected to identify hybridoma cell lines that produce antibodies containing human heavy chain and human λ light chain that are specific to the antigen used for immunization. DNA encoding the variable regions of the heavy chains and the λ light chains may be isolated and linked to desirable isotypic constant regions of the heavy chain and light chain. Due to the presence of the additional hVλ gene segments as compared to the endogenous mouse λ locus, the diversity of the light chain repertoire is dramatically increased and confers higher diversity on the antigen-specific repertoire upon immunization. The resulting cloned antibody sequences may be subsequently produced in a cell, such as a CHO cell. Alternatively, DNA encoding the antigen-specific chimeric antibodies or the variable domains of the light and heavy chains may be isolated directly from antigen-specific lymphocytes (e.g., B cells).

Initially, high affinity chimeric antibodies are isolated having a human variable region and a mouse constant region. As described above, the antibodies are characterized and selected for desirable characteristics, including affinity, selectivity, epitope, etc. The mouse constant regions are replaced with a desired human constant region to generate the fully human antibody containing a somatically mutated human heavy chain and a human λ light chain derived from an unrearranged human λ light chain locus of the invention. Suitable human constant regions include, for example wild type or modified IgG1, IgG2, IgG3, or IgG4.

We claim:

1. A mouse whose genome comprises an immunoglobulin locus comprising human Vλ and Jλ gene segments operably linked to a mouse Cκ gene such that the mouse expresses an immunoglobulin light chain that comprises derived from the Vλ and Jλ gene segments fused with a mouse κ constant domain.

2. The mouse of claim 1, wherein the human Vλ and Jλ gene segments comprise at least 12 human Vλ gene segments.

3. The mouse of claim 1, wherein the human Vλ and Jλ gene segments comprise at least 28 human Vλ gene segments.

4. The mouse of claim 1, wherein the human Vλ and Jλ gene segments comprise at least 40 human Vλ gene segments.

5. The mouse of claim 1, wherein the human Vλ and Jλ gene segments comprise a human Jλ1 gene segment.

6. The mouse of claim 1, wherein the mouse further comprises a human Vκ-Jκ intergenic region sequence located between the human Vλ gene segments and the human Jλ gene segments, wherein the Vκ-Jκ intergenic region is the region located about 130 bp downstream of the 3' untranslated region of a human Vκ4-1 gene segment to about 600 bp upstream of a human Jκ1 gene segment as found in a human genome.

7. The mouse of claim 6, wherein the human Vκ-Jκ intergenic region sequence comprises SEQ ID NO: 100.

* * * * *